United States Patent
Bosch Tubert et al.

(10) Patent No.: US 10,617,771 B2
(45) Date of Patent: Apr. 14, 2020

(54) ADENOASSOCIATED VIRUS VECTORS FOR THE TREATMENT OF MUCOPOLYSACCHARIDOSES

(71) Applicants: UNIVERSITAT AUTÓNOMA DE BARCELONA, Cerdanyola del Valles (ES); ESTEVE PHARMACEUTICALS, S.A., Barcelona (ES)

(72) Inventors: Maria Fàtima Bosch Tubert, Cerdanyola del Valles (ES); Virginia Areba Haurigot, Barcelona (ES); Sandra Motas Mallol, Foixá (ES)

(73) Assignees: UNIVERSITAT AUTÓNOMA DE BARCELONA, Cerdanyola del Valles (ES); ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 15/578,366

(22) PCT Filed: Jun. 3, 2016

(86) PCT No.: PCT/EP2016/062655
§ 371 (c)(1),
(2) Date: Nov. 30, 2017

(87) PCT Pub. No.: WO2016/193431
PCT Pub. Date: Dec. 8, 2016

(65) Prior Publication Data
US 2018/0169272 A1 Jun. 21, 2018

(30) Foreign Application Priority Data
Jun. 5, 2015 (EP) .................................... 15382297

(51) Int. Cl.
*C12N 9/16* (2006.01)
*A61K 48/00* (2006.01)
*A61P 43/00* (2006.01)
*A61K 9/00* (2006.01)
*C12N 15/79* (2006.01)

(52) U.S. Cl.
CPC ........ *A61K 48/0066* (2013.01); *A61K 9/0019* (2013.01); *A61K 48/00* (2013.01); *A61K 48/0016* (2013.01); *A61K 48/0075* (2013.01); *A61P 43/00* (2018.01); *C12N 9/16* (2013.01); *C12N 15/79* (2013.01); *C12Y 301/06013* (2013.01); *C12N 2750/14143* (2013.01); *C12N 2800/22* (2013.01)

(58) Field of Classification Search
None
See application file for complete search history.

(56) References Cited

U.S. PATENT DOCUMENTS

2013/0236442 A1 9/2013 Lee
2014/0004593 A1 1/2014 Boldog et al.

FOREIGN PATENT DOCUMENTS

KR 20040084881 10/2004
WO WO2011108451 9/2011
WO WO2013151666 10/2013

OTHER PUBLICATIONS

Laoharawee et al, (Molecular Therapy, vol. 23, Supplement 1, May 2015, abstract, 369) (Year: 2015).*
Akiyama et al., "Enzyme augmentation therapy enhances the therapeutic efficacy of bone marrow transplantation in mucopolysaccharidosis type II mice", Mol Genet Metab., 111, 2014, pp. 139-146.
Bainbridge et al., "Effect of gene therapy on visual function in Leber's congenital amaurosis", N Engl J Med., 358:21, 2008, pp. 2231-2239.
Buchlis et al., Factor IX expression in skeletal muscle of a server hemophilia B patient 10 years after AAV-mediated gene transfer, Blood, vol. 119, No. 13, 2012, pp. 3038-3041.
Burton et al., Incidence and timing of infusion-related reactions in patients with mucopolysaccharidosis type II (Hunter syndrome) on idursulfase therapy in the real-world setting: A perspective from the Hunter outcome survey (HOS), Mol Genet Metab., 103, 2011, pp. 113-120.
Enns et al., "Central nervous system therapy for lysosomal storage disorders", Neurosurg Focus, 24 (3&4):E11, 2008, pp. 1-12.
European Search Report for EP15382297.8 dated Mar. 5, 2016.
Garcia et al., Preclinical dose ranging studies for enzyme replacement therapy with idursulfase in a knock-out mouse model of MPS II, Mol Genet Metab, 91, 2007, pp. 183-190.
Giugliani et al., Mucopolysaccharidosis I, II, and VI: brief review and guidelines for treatment, Genet Mol Biol., 33, 4, 2010, pp. 589-604.
Guillen-Navarro et al., "Clinical manifestations in femal carriers of mucopolysaccharidosis type II: a spanish cross-sectional study", Orphanet J Rare Dis, 8:92, 2013, pp. 1-7.
Hauswirth et al., "Treatment of Leber Congenital Amaurosis due to RPE65 mutations by ocular subretinal injection of adeno-associated virus gene vector: short-term results of a phase I trial", Hum Gene Ther., 19, 2008, pp. 979-990.
Higuchi, et al., "Enzyme replacement therapy (ERT) procedure for mucopolysaccharidosis type II (MPS II) by intraventricular administration (IVA) in murine MPS II", Molecular Genetics and Metabolism, 107, 2012, pp. 122-128.
Hunter, et al., "A rare disease in two brothers", Proc R Soc Med., 1917, pp. 104-116.

(Continued)

*Primary Examiner* — Anoop K Singh
*Assistant Examiner* — Magdalene K Sgagias
(74) *Attorney, Agent, or Firm* — Hueschen and Sage

(57) ABSTRACT

The present invention provides new Adeno-associated virus-derived vectors and pharmaceutical compositions containing the same for the treatment of lysosomal storage disorders and specially, for the treatment of mucopolysaccharidoses Type II.

7 Claims, 21 Drawing Sheets
Specification includes a Sequence Listing.

(56) References Cited

OTHER PUBLICATIONS

International Search Report for PCT/EP2016/062655 dated Aug. 17, 2016.
Krivit et al., "Microglia: the effector cell for reconstitution of the central nervous system following bone marrow transplantation for lysosomal and peroxisomal storage diseases", Cell Transplantation, vol. 4, No. 4, 1995, pp. 385-392.
Maguire et al., "Safety and efficacy of gene transfer for Leber's Congenital Amaurosis", N Engl J Med., 385(21), 2008, pp. 2240-2248.
Meikle P, et al., "Prevalence of lysosomal storage disorders", JAMA, vol. 281, No. 3, 1999, pp. 249-254.
Mossman et al., "Hunters disease in a girl: association with X:5 chromosomal translocation disrupting the Hunter gene", Archives of Disease in Childhood, 58, 1983, pp. 911-915.
Muenzer et al., "A phase I/II clinical trial of enzyme replacement therapy in mucopolysaccharidosis II (Hunter syndrome)", Molecular Genetics and Metabolism, 90, 2007, pp. 329-337.
Muenzer et al., "A phase I/II study of intrathecal idursulfase-IT in children with severe mucopolysaccharidosis II", Genetics in Medicine, vol. 18, No. 1, 2015. pp. 73-81.
Muenzer et al., "A phase I/II clinical study of enzyme replacement therapy with idursulfase in mucopolysaccharidosis II (Hunter syndrome)", Genetics in Medicine, 8(8), 2006, pp. 465-473.
Muenzer et al., "Long-term, open-labeled extension study of idursulfase in the treatment of Hunter syndrome", Genetics in Medicine, vol. 13, No. 2, 2011, pp. 95-101.
Nathwani et al., "Adenovirus-associated virus vector-mediated gene transfer in hemophilia B". N Engl J Med., 365(25), 2011, pp. 2357-2365.
Neufeld and Muenzer, "The mucopolysaccharidoses, Downloaded from the Online Metabolic & Molecular Bases of Inherited Disease" (www.ommbid.com), Chapter 136, 2001, pp. 3421-3452.
Niemeyer et al., "Long-term correction of inhibitor-prone hemophilia B dogs treated with liver-directed AAV2-mediated factor IX gene therapy", Blood, vol. 113, No. 4, 2009, pp. 797-806.
Peters and Steward, "Hematopoietic cell transplantation for inherited metabolic diseases: an overview of outcomes and practice guidelines", Bone Marrow Transplantation, 31, 2003, pp. 229-239.
Peters et al., "Outcome of unrelated donor bone marrow transplantation in 40 children with Hurler Syndrome", Blood, vol. 87, No. 11, 1996, pp. 4894-4902.
Podetz-Pedersen et al., "Prevention of neurocognitive deficit by ex vivo lentiviral transduction of hematopoietic stem cells in a murine model of mucopolysaccharidosis type II", Molecular Therapy, vol. 21, 2013, pp. S191.
Polito et al., "Correction of CNS defects in the MPSII mouse model via systemic enzyme replacement therapy", Human Molecular Genetics. vol. 19, No. 24, 2010, pp. 4871-4885.
Rivera et al., Long-term pharmacologically regulated expression of erythropoietin in primates following AAV—mediated gene transfer, Blood, vol. 105, No. 4, 2005, pp. 1424-1430.
Schwartz et al., "A clinical study of 77 patients with mucopolysaccharidosis type II", Acta Paediatrica, 96, 2007, pp. 63-70.
Seto et al., "Brain effect of bone magnetic resonance imaging marrow transplantation", Ann Neurol, 50, 2001, pp. 79-82.
Sohn et al., Phase I/II clinical trial of enzyme replacement therapy with idursulfase beta in patients with mucopolysaccharidosis II (Hunter Syndrome), Orphanet Journal of Rare Diseases, 8:42, 2013, pp. 1-8.
Valayannopoulos, et al., Therapy for the mucopolysaccharidoses, Rheumatology, 50, 2011, pp. v49-v59.
Valstar et al., Sanfilippo syndrome: a mini-review, J. Inherit. Metab. Dis., 31, 2008, pp. 240-252.
Vellodi et al., "Long-term follow-up following bone marrow transplantation for Hunter disease", J Inherit Metab Dis., 22, 1999, pp. 638-648.
Wraith et al., "Mucopolysaccharidosis type II (Hunter syndrome): a clinical review and recommendations for treatment in the era of enzyme replacement therapy" Eur J Pediatr, 167, 2008, pp. 267-277.
Wyatt et al., "The effectiveness and cost of enzyme replacement and substrate reduction therapies: a longitudinal cohort study of people with lysosomal storage disorders", Health Technology Assessment, vol. 16, No. 39, 2012, pp. 1-289.
Yamada, et al., "Treatment of MPS VII (Sly disease) by allogeneic BMT in a female with homozygous A619V mutation", Bone Marrow Transplantation, 21, 1998, pp. 629-634.
Aronovich, Elena, L., et al., "Lysosomal storage disease: gene therapy on both sides of the blood-brain barrier", Molecular Genetics and Metabolism, 114, 2015, pp. 83-93.
Cardone, Monica, et al., "Correction of Hunter syndrome in the MPSII mouse model by AAV2/8-mediated gene delivery", Human Molecular Genetics, No. 7, Jan. 1, 2006, pp. 1225-1236.
Frisco, A., et al., "Gene therapy of Hunter syndrome: evaluation of the efficiency of muscle electro gene transfer for the production and release of recombinant iduronate-2-sulfatase (IDS)", Biochimica et Biophysica Acta, 1782, 2008, pp. 574-580.
Jung, Sung-Chul, et al., "Characterization of a novel mucopolysaccharidosis type II mouse model and recombinant AAV2/8 vector-mediated gene therapy", Molecules and Cells, vol. 30, No. 1, Jul. 31, 2010, pp. 13-18.
Muenzer, Joseph, et al., "Improved brain expression of iduronate sulfatase in the MPS II mouse after intravenous delivery of a self-complimentary adeno-associated viral (AAV) vector", Molecular Genetics and Metabolism, vol. 108, No. 2, Feb. 1, 2013, pp. S163.
Polito, Vinicia Assunta, et al., "IDS crossing of the blood-brain barrier corrects CNS defects in MPSII mice", The American Journal of Human Genetics, 85, Aug. 14, 2009, pp. 269-301.

* cited by examiner

Optimized human IDS-version1

A

B

Optimized human IDS-version2

A

B

Optimized murine IDS

A

B

Hydrodynamic injection of pAAV-CAG-hIDS, pAAV-CAG-ohIDS-version1 and pAAV-CAG-ohIDS-version2 plasmids in healthy mice Intravenous injection of AAV9-CAG-hIDS, AAV9-CAG-ohIDS-version1 and AAV9-CAG-ohIDS-version2 vectors in MPSII mice Intra-CSF injection of AAV9-CAG-hIDS, AAV9-CAG-ohIDS-version1 and AAV9-CAG-ohIDS-version2 vectors in MPSII mice Intra-CSF injection of AAV9-CAG-hIDS, AAV9-CAG-ohIDS-version1 and AAV9-CAG-ohIDS-version2 vectors in MPSII mice

Intra-CSF - optimized murine IDS Dose-Response

SEQUENCE LISTING

<160> NUMBER OF SEQ ID NOS: 20

<210> SEQ ID NO 1
<211> LENGTH: 550
<212> TYPE: PRT
<213> ORGANISM: Homo sapiens

<400> SEQUENCE: 1

```
Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415
```

```
Gln Val Pro Pro Arg Cys Pro Val Pro Ser Phe His Val Glu Leu Cys
                420                 425                 430

Arg Glu Gly Lys Asn Leu Leu Lys His Phe Arg Phe Arg Asp Leu Glu
            435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
                515                 520                 525

Pro Leu Gln Asp His Asn Met Tyr Asn Asp Ser Gln Gly Gly Asp Leu
    530                 535                 540

Phe Gln Leu Leu Met Pro
545                 550

<210> SEQ ID NO 2
<211> LENGTH: 1653
<212> TYPE: DNA
<213> ORGANISM: Homo sapiens

<400> SEQUENCE: 2
atgccgccac cccggaccgg ccgaggcctt ctctggctgg gtctggttct gagctccgtc     60
tgcgtcgccc tcggatccga aacgcaggcc aactcgacca cagatgctct gaacgttctt    120
ctcatcatcg tggatgacct cgcccctcc ctgggctgtt atggggataa gctggtgagg    180
tccccaaata ttgaccaact ggcatcccac agcctcctct tccagaatgc ctttgcgcag    240
caagcagtgt gcgccccgag ccgcgtttct ttcctcactg caggagacc tgacaccacc    300 cgcctgtacg acttcaactc ctactggagg gtgcacgctg gaaacttctc caccatcccc    360
cagtacttca ggagaatggg ctatgtgacc atgtcggtgg aaaagtctt tcaccctggg    420 atatcttcta accataccga tgattctccg tatagctggc tttttccacc ttatcatcct    480
tcctctgaga gtatgaaaaa cactaagaca tgtcgagggc agatggagaa actccatgcc    540
aacctgcttt gccctgtgga tgtgctggat gttcccgagg gcaccttgcc tgacaaacag    600
agcactgagc aagccataca gttgttggaa aagatgaaaa cgtcagccag tcctttcttc    660
ctggccgttg gtatcataa gccacacatc cccttcagat accccaagga atttcagaag    720
ttgtatccct ggagaacat caccctggcc ccgatcccg aggtccctga tggcctaccc    780
cctgtggcct acaaccctg gatggacatc aggcaacggg aagacgtcca agccttaaac    840
atcagtgtgc cgtatggtcc aattcctgtg gactttcagc ggaaaatccg ccagagctac    900
tttgcctctg tgtcatattt ggatacacag gtcggccgcc tcttgagtgc tttggacgat    960
cttcagctgg ccaacagcac catcattgca tttacctcgg atcatgggtg ggctctaggt   1020
gaacatggag aatgggccaa atacagcaat tttgatgttg ctacccatgt tcccctgata   1080
ttctatgttc ctggaaggac ggcttcactt ccggaggcag gcgagaagct tttcccttac   1140
ctcgaccctt ttgattccgc ctcacagttg atggagccag gcaggcaatc catggacctt   1200
gtggaacttg tgtctctttt tcccacgctg gctggacttg caggactgca ggttccacct   1260
cgctgccccg ttccttcatt tcacgttgag ctgtgcagag aaggcaagaa ccttctgaag   1320
```

```
cattttcgat tccgtgactt ggaagaggat ccgtacctcc ctggtaatcc ccgtgaactg      1380
attgcctata gccagtatcc ccggccttca gacatccctc agtggaattc tgacaagccg      1440
agtttaaaag atataaagat catgggctat tccatacgca ccatagacta taggtatact      1500
gtgtgggttg gcttcaatcc tgatgaattt ctagctaact tttctgacat ccatgcaggg      1560
gaactgtatt ttgtggattc tgacccattg caggatcaca atatgtataa tgattcccaa      1620
ggtggagatc ttttccagtt gttgatgcct tga                                   1653

<210> SEQ ID NO 3
<211> LENGTH: 7900
<212> TYPE: DNA
<213> ORGANISM: Artificial Sequence
<220> FEATURE:
<223> OTHER INFORMATION: pAAV-CAG-hIDS

<400> SEQUENCE: 3
aaatacgcgt atgccgccac cccggaccgg ccgaggcctt ctctggctgg gtctggttct        60
gagctccgtc tgcgtcgccc tcggatccga aacgcaggcc aactcgacca cagatgctct       120
gaacgttctt ctcatcatcg tggatgacct gcgcccctcc ctgggctgtt atggggataa       180
gctggtgagg tccccaaata ttgaccaact ggcatcccac agcctcctct tccagaatgc       240 cttttgcgcag caagcagtgt gcgccccgag ccgcgtttct ttcctcactg gcaggagacc      300
tgacaccacc cgcctgtacg acttcaactc ctactggagg gtgcacgctg aaacttctc       360 caccatcccc cagtacttca aggagaatgg ctatgtgacc atgtcggtgg aaaagtctt       420 tcaccctggg atatcttcta accataccga tgattctccg tatagctggt cttttccacc       480
ttatcatcct tcctctgaga gtatgaaaaa cactaagaca tgtcgagggc cagatggaga       540
actccatgcc aacctgcttt gccctgtgga tgtgctggat gttcccgagg caccttgcc       600 tgacaaacag agcactgagc aagccataca gttgttggaa aagatgaaaa cgtcagccag       660
tccttttctc ctggccgttg ggtatcataa gccacacatc cccttcagat accccaagga       720
atttcagaag ttgtatccct tggagaacat caccctggcc cccgatcccg aggtccctga       780
tggcctaccc cctgtggcct acaaccctg gatggacatc aggcaacggg aagacgtcca       840
agccttaaac atcagtgtgc cgtatggtcc aattcctgtg gactttcagc ggaaaatccg       900
ccagagctac tttgcctctg tgtcatattt ggatacacag gtcggccgcc tcttgagtgc       960 tttgacgat cttcagctgg ccaacagcac catcattgca tttacctcgg atcatgggtg      1020
ggctctaggt gaacatggag aatgggccaa atacagcaat tttgatgttg ctacccatgt      1080 tccctgata ttctatgttc ctggaaggac ggcttcactt ccggaggcag gcgagaagct      1140
tttcccttac ctcgaccctt ttgattccgc ctcacagttg atggagccag gcaggcaatc      1200 catggaccttt gtgaacttg tgtctctttt tcccacgctg gctggacttg caggactgca      1260
ggttccacct cgctgccccg ttccttcatt tcacgttgag ctgtgcagag aaggcaagaa      1320
ccttctgaag cattttcgat tccgtgactt ggaagaggat ccgtacctcc ctggtaatcc      1380
ccgtgaactg attgcctata gccagtatcc ccggccttca gacatccctc agtggaattc      1440
tgacaagccg agtttaaaag atataaagat catgggctat tccatacgca ccatagacta      1500
taggtatact gtgtgggttg gcttcaatcc tgatgaattt ctagctaact tttctgacat      1560
ccatgcaggg gaactgtatt ttgtggattc tgacccattg caggatcaca atatgtataa      1620
tgattcccaa ggtggagatc ttttccagtt gttgatgcct tgagaattca tttaattcga      1680
gctcggtacc cgggaatcaa ttcactcctc aggtgcaggc tgcctatcag aaggtggtgg      1740
```

-continued

```
ctggtgtggc caatgccctg gctcacaaat accactgaga tcttttttccc tctgccaaaa    1800
attatgggga catcatgaag cccccttgagc atctgacttc tggctaataa aggaaattta    1860
ttttcattgc aatagtgtgt tggaattttt tgtgtctctc actcggaagg acatatggga    1920
gggcaaatca tttaaaacat cagaatgagt atttggttta gagtttggca acatatgccc    1980
atatgctggc tgccatgaac aaaggttggc tataaagagg tcatcagtat atgaaacagc    2040
cccctgctgt ccattcctta ttccatagaa aagccttgac ttgaggttag atttttttta    2100
tattttgttt tgtgttattt ttttcttttaa catccctaaa attttcctta catgttttac    2160
tagccagatt tttcctcctc tcctgactac tcccagtcat agctgtccct cttctcttat    2220
ggagatccct cgacctgcag cccaagctgt agataagtag catggcgggt taatcattaa    2280
ctacaaggaa cccctagtga tggagttggc cactccctct ctgcgcgctc gctcgctcac    2340
tgaggccgcc cgggctttgc ccgggcggcc tcagtgagcg agcgagcgcg cagctgcatt    2400
aatgaatcgg ccaacgcgcg gggagaggcg gtttgcgtat tgggcgctct tccgcttcct    2460
cgctcactga ctcgctgcgc tcggtcgttc ggctgcggcg agcggtatca gctcactcaa    2520
aggcggtaat acggttatcc acagaatcag gggataacgc aggaaagaac atgtgagcaa    2580
aaggccagca aaaggccagg aaccgtaaaa aggccgcgtt gctggcgttt ttccataggc    2640
tccgcccccc tgacgagcat cacaaaaatc gacgctcaag tcagaggtgg cgaaacccga    2700
caggactata aagataccag gcgtttcccc ctggaagctc cctcgtgcgc tctcctgttc    2760
cgaccctgcc gcttaccgga tacctgtccg cctttctccc ttcgggaagc gtggcgcttt    2820
ctcatagctc acgctgtagg tatctcagtt cggtgtaggt cgttcgctcc aagctgggct    2880
gtgtgcacga accccccgtt cagcccgacc gctgcgcctt atccggtaac tatcgtcttg    2940
agtccaaccc ggtaagacac gacttatcgc cactggcagc agccactggt aacaggatta    3000
gcagagcgag gtatgtaggc ggtgctacag agttcttgaa gtggtggcct aactacggct    3060
acactagaag aacagtattt ggtatctgcg ctctgctgaa gccagttacc ttcggaaaaa    3120
gagttggtag ctcttgatcc ggcaaacaaa ccaccgctgg tagcggtggt ttttttgttt    3180
gcaagcagca gattacgcgc agaaaaaaag gatctcaaga agatcctttg atcttttcta    3240
cggggtctga cgctcagtgg aacgaaaact cacgttaagg attttggtc atgagattat    3300
caaaaaggat cttcacctag atcctttaa attaaaaatg aagttttaaa tcaatctaaa    3360
gtatatatga gtaaacttgg tctgacagtt accaatgctt aatcagtgag gcacctatct    3420
cagcgatctg tctatttcgt tcatccatag ttgcctgact ccccgtcgtg tagataacta    3480
cgatacggga gggcttacca tctggcccca gtgctgcaat gataccgcga gacccacgct    3540
caccggctcc agatttatca gcaataaacc agccagccgg aagggccgag cgcagaagtg    3600
gtcctgcaac tttatccgcc tccatccagt ctattaattg ttgccgggaa gctagagtaa    3660
gtagttcgcc agttaatagt ttgcgcaacg ttgttgccat tgctacaggc atcgtggtgt    3720
cacgctcgtc gtttggtatg gcttcattca gctccggttc ccaacgatca aggcgagtta    3780
catgatcccc catgttgtgc aaaaaagcgg ttagctcctt cggtcctccg atcgttgtca    3840
gaagtaagtt ggccgcagtg ttatcactca tggttatggc agcactgcat aattctctta    3900
ctgtcatgcc atccgtaaga tgcttttctg tgactggtga gtactcaacc aagtcattct    3960
gagaatagtg tatgcggcga ccgagttgct cttgcccggc gtcaatacgg ataataccg    4020
cgccacatag cagaacttta aaagtgctca tcattggaaa acgttcttcg gggcgaaaac    4080
tctcaaggat cttaccgctg ttgagatcca gttcgatgta acccactcgt gcacccaact    4140
```

```
gatcttcagc atctttttact ttcaccagcg tttctgggtg agcaaaaaca ggaaggcaaa    4200
atgccgcaaa aaagggaata agggcgacac ggaaatgttg aatactcata ctcttccttt    4260
ttcaatatta ttgaagcatt tatcagggtt attgtctcat gagcggatac atatttgaat    4320
gtatttagaa aaataaacaa ataggggttc cgcgcacatt tccccgaaaa gtgccacctg    4380
acgtctaaga aaccattatt atcatgacat taacctataa aaataggcgt atcacgaggc    4440
cctttcgtct cgcgcgtttc ggtgatgacg gtgaaaacct ctgacacatg cagctcccgg    4500
agacggtcac agcttgtctg taagcggatg ccggagcag acaagcccgt cagggcgcgt     4560
cagcgggtgt tggcgggtgt cggggctggc ttaactatgc ggcatcagag cagattgtac    4620
tgagagtgca ccatatgcgg tgtgaaatac cgcacagatg cgtaaggaga aataccgca     4680
tcaggcgatt ccaacatcca ataaatcata caggcaaggc aaagaattag caaaattaag    4740
caataaagcc tcagagcata aagctaaatc ggttgtacca aaacattat gaccctgtaa     4800
tacttttgcg ggagaagcct ttatttcaac gcaaggataa aaattttag aaccctcata     4860
tattttaaat gcaatgcctg agtaatgtgt aggtaaagat tcaaacgggt gagaaaggcc    4920
ggagacagtc aaatcaccat caatatgata ttcaaccgtt ctagctgata aattcatgcc    4980
ggagagggta gctattttg agaggtctct acaaaggcta tcaggtcatt gcctgagagt     5040
ctggagcaaa caagagaatc gatgaacggt aatcgtaaaa ctagcatgtc aatcatatgt    5100
accccggttg ataatcagaa aagccccaaa aacaggaaga ttgtataagc aaatatttaa    5160
attgtaagcg ttaatatttt gttaaaattc gcgttaaatt tttgttaaat cagctcattt    5220
tttaaccaat aggccgaaat cggcaaaatc ccttataaat caaagaata gaccgagata     5280
gggttgagtg ttgttccagt ttggaacaag agtccactat taagaacgt ggactccaac     5340
gtcaaagggc gaaaaaccgt ctatcagggc gatggcccac tacgtgaacc atcaccctaa    5400
tcaagttttt tggggtcgag gtgccgtaaa gcactaaatc ggaaccctaa agggagcccc    5460
cgatttagag cttgacgggg aaagccggcg aacgtggcga aaaggaagg gaagaaagcg    5520
aaaggagcgg cgctagggc gctggcaagt gtagcggtca cgctgcgcgt aaccaccaca    5580
cccgccgcgc ttaatgcgcc gctacagggc gcgtactatg gttgctttga cgagcacgta    5640
taacgtgctt tcctcgttag aatcagagcg ggagctaaac aggaggccga ttaagggat     5700
tttagacagg aacggtacgc cagaatcctg agaagtgttt ttataatcag tgaggccacc    5760
gagtaaaaga gtctgtccat cacgcaaatt aaccgttgtc gcaatacttc tttgattagt    5820
aataacatca cttgcctgag tagaagaact caaactatcg gccttgctgg taatatccag    5880
aacaatatta ccgccagcca ttgcaacgga atcgccattc gccattcagg ctgcgcaact    5940
gttgggaagg gcgatcggtg cgggcctctt cgctattacg ccagctgcgc gctcgctcgc    6000
tcactgaggc cgcccgggca aagcccgggc gtcgggcgac ctttggtcgc ccggcctcag    6060
tgagcgagcg agcgcgcaga gagggagtgg ccaactccat cactaggggt tccttgtagt    6120
taatgattaa cccgccatgc tacttatcta ctcgacattg attattgact agttattaat    6180
agtaatcaat tacggggtca ttagttcata gcccatatat ggagttccgc gttacataac    6240
ttacggtaaa tggcccgcct ggctgaccgc ccaacgaccc ccgcccattg acgtcaataa    6300
tgacgtatgt tcccatagta acgccaatag ggactttcca ttgacgtcaa tgggtggagt    6360
atttacggta aactgcccac ttggcagtac atcaagtgta tcatatgcca agtacgcccc    6420
ctattgacgt caatgacggt aaatggcccg cctggcatta tgcccagtac atgaccttat    6480
gggactttcc tacttggcag tacatctacg tattagtcat cgctattacc atggtcgagg    6540
```

| | |
|---|---:|
| tgagccccac gttctgcttc actctcccca tctcccccc ctccccaccc ccaattttgt | 6600 |
| atttatttat tttttaatta ttttgtgcag cgatggggc gggggggggg ggggggcgcg | 6660 |
| cgccaggcgg ggcggggcgg ggcgagggc ggggcggggc gaggcggaga ggtgcggcgg | 6720 |
| cagccaatca gagcggcgcg ctccgaaagt ttccttttat ggcgaggcgg cggcggcggc | 6780 |
| ggccctataa aaagcgaagc gcgcggcggg cgggagtcgc tgcgttgcct tcgccccgtg | 6840 |
| ccccgctccg ccgccgcctc gcgccgcccg ccccggctct gactgaccgc gttactccca | 6900 |
| caggtgagcg ggcgggacgg cccttctcct ccgggctgta attagcgctt ggtttaatga | 6960 |
| cggcttgttt cttttctgtg gctgcgtgaa agccttgagg ggctccggga gggccctttg | 7020 |
| tgcgggggga gcggctcggg gggtgcgtgc gtgtgtgtgt gcgtggggag cgccgcgtgc | 7080 |
| ggctccgcgc tgcccggcgg ctgtgagcgc tgcgggcgcg gcgcggggct ttgtgcgctc | 7140 |
| cgcagtgtgc gcgaggggag cgcggccggg ggcggtgccc cgcggtgcgg gggggctgc | 7200 |
| gaggggaaca aaggctgcgt gcgggtgtg tgcgtggggg ggtgagcagg gggtgtgggc | 7260 |
| gcgtcggtcg ggctgcaacc cccctgcac cccctcccc gagttgctga gcacggcccg | 7320 |
| gcttcgggtg cggggctccg tacggggcgt ggcgcggggc tcgccgtgcc gggcgggggg | 7380 |
| tggcggcagg tggggtgcc gggcggggcg gggccgcctc gggccgggga gggctcgggg | 7440 |
| gaggggcgcg gcggccccg gagcgccggc ggctgtcgag gcgcggcgag ccgcagccat | 7500 |
| tgccttttat ggtaatcgtg cgagagggcg cagggacttc ctttgtccca aatctgtgcg | 7560 |
| gagccgaaat ctgggaggcg ccgccgcacc ccctctagcg ggcgcggggc gaagcggtgc | 7620 |
| ggcgccggca ggaaggaaat gggcgggag ggccttcgtg cgtcgccgcg ccgccgtccc | 7680 |
| cttctcccte tccagcctcg gggctgtccg cgggggacg gctgccttcg gggggacgg | 7740 |
| ggcagggcgg ggttcggctt ctggcgtgtg accggcggct ctagagcctc tgctaaccat | 7800 |
| gttcatgcct tcttcttttt cctacagctc ctgggcaacg tgctggttat tgtgctgtct | 7860 |
| catcattttg gcaaagaatt gattaattcg agcgaacgcg | 7900 |

<210> SEQ ID NO 4
<211> LENGTH: 4319
<212> TYPE: DNA
<213> ORGANISM: Artificial Sequence
<220> FEATURE:
<223> OTHER INFORMATION: AAV9-CAG-hIDS

<400> SEQUENCE: 4

| | |
|---|---:|
| attacgccag ctgcgcgctc gctcgctcac tgaggccgcc cgggcaaagc ccggcgtcg | 60 |
| ggcgaccttt ggtcgcccgg cctcagtgag cgagcgagcg cgcagagagg gagtggccaa | 120 |
| ctccatcact aggggttcct tgtagttaat gattaacccg ccatgctact tatctactcg | 180 |
| acattgatta ttgactagtt attaatagta atcaattacg gggtcattag ttcatagccc | 240 |
| atatatggag ttccgcgtta cataacttac ggtaaatggc ccgcctggct gaccgcccaa | 300 |
| cgacccccgc ccattgacgt caataatgac gtatgttccc atagtaacgc caatagggac | 360 |
| tttccattga cgtcaatggg tggagtattt acggtaaact gcccacttgg cagtacatca | 420 |
| agtgtatcat atgccaagta cgccccctat tgacgtcaat gacggtaaat ggcccgcctg | 480 |
| gcattatgcc cagtacatga ccttatggga ctttcctact tggcagtaca tctacgtatt | 540 |
| agtcatcgct attaccatgg tcgaggtgag ccccacgttc tgcttcactc tccccatctc | 600 |
| cccccctcc ccaccccaa ttttgtattt atttattttt taattatttt gtgcagcgat | 660 |
| ggggcgggg ggggggggg ggcgcgcgcc aggcgggcg gggcggggcg aggggcgggg | 720 |

```
cggggcgagg cggagaggtg cggcggcagc caatcagagc ggcgcgctcc gaaagtttcc    780
ttttatggcg aggcggcggc ggcggcggcc ctataaaaag cgaagcgcgc ggcgggcggg    840
agtcgctgcg ttgccttcgc cccgtgcccc gctccgccgc cgcctcgcgc cgcccgcccc    900
ggctctgact gaccgcgtta ctcccacagg tgagcgggcg ggacggccct tctcctccgg    960
gctgtaatta gcgcttggtt taatgacggc ttgtttcttt tctgtggctg cgtgaaagcc   1020
ttgaggggct ccgggagggc cctttgtgcg ggggagcgg ctcggggggt gcgtgcgtgt   1080
gtgtgtgcgt ggggagcgcc gcgtgcggct ccgcgctgcc cggcggctgt gagcgctgcg   1140
ggcgcggcgc ggggctttgt gcgctccgca gtgtgcgcga gggagcgcg gccggggcg    1200
gtgccccgcg gtgcggggg ggctgcgagg ggaacaaagg ctgcgtgcgg ggtgtgtgcg   1260
tgggggggtg agcagggggt gtgggcgcgt cggtcgggct gcaaccccc ctgcaccccc    1320
ctccccgagt tgctgagcac ggcccggctt cgggtgcggg gctccgtacg gggcgtggcg   1380
cggggctcgc cgtgccgggc ggggggtggc ggcaggtggg ggtgccgggc ggggcggggc   1440
cgcctcgggc cggggagggc tcggggagg ggcgcggcgg cccccggagc gccggcggct   1500
gtcgaggcgc ggcgagccgc agccattgcc ttttatggta atcgtgcgag agggcgcagg   1560
gacttccttt gtcccaaatc tgtgcggagc cgaaatctgg gaggcgccgc cgcaccccct   1620
ctagcgggcg cggggcgaag cggtgcggcg ccggcaggaa ggaaatgggc ggggagggcc   1680
ttcgtgcgtc gccgcgccgc cgtccccttc tccctctcca gcctcgggc tgtccgcggg   1740
gggacggctg ccttcggggg ggacggggca gggcggggtt cggcttctgg cgtgtgaccg   1800
gcggctctag agcctctgct aaccatgttc atgccttctt cttttcccta cagctcctgg   1860
gcaacgtgct ggttattgtg ctgtctcatc attttggcaa agaattgatt aattcgagcg   1920
aacgcgaaat acgcgtatgc cgccaccccg gaccggccga ggccttctct ggctgggtct   1980
ggttctgagc tccgtctgcg tcgccctcgg atccgaaacg caggccaact cgaccacaga   2040
tgctctgaac gttcttctca tcatcgtgga tgacctgcgc ccctccctgg gctgttatgg   2100
ggataagctg gtgaggtccc caaatattga ccaactggca tcccacagcc tcctcttcca   2160
gaatgccttt gcgcagcaag cagtgtgcgc cccgagccgc gtttctttcc tcactggcag   2220
gagacctgac accacccgcc tgtacgactt caactcctac tggagggtgc acgctggaaa   2280
cttctccacc atccccagt acttcaagga gaatggctat gtgaccatgt cggtgggaaa   2340
agtctttcac cctgggatat cttctaacca taccgatgat tctccgtata gctggtcttt   2400
tccaccttat catccttcct ctgagaagta tgaaaacact aagacatgtc gagggccaga   2460
tggagaactc catgccaacc tgctttgccc tgtggatgtg ctggatgttc ccgagggcac   2520
cttgcctgac aaacagagca ctgagcaagc catacagttg ttggaaaaga tgaaaacgtc   2580
agccagtcct ttcttcctgg ccgttgggta tcataagcca cacatcccct tcagataccc   2640
caaggaattt cagaagttgt atccttgga gaacatcacc ctggccccg atccgaggt    2700
ccctgatggc ctaccccctg tggcctacaa ccctgatg acatcaggc aacgggaaga   2760
cgtccaagcc ttaaacatca gtgtgccgta tggtccaatt cctgtggact tcagcggaa   2820
aatccgccag agctactttg cctctgtgtc atatttggat acacaggtcg gccgcctctt   2880
gagtgctttg gacgatcttc agctggccaa cagcaccatc attgcattta cctcggatca   2940
tgggtgggct ctaggtgaac atggagaatg ggccaaatac agcaattttg atgttgctac   3000
ccatgttccc ctgatattct atgttcctgg aaggacggc tcacttccgg aggcaggcga   3060
gaagcttttc ccttaccctcg accctttga ttccgcctca cagttgatgg agccaggcag   3120
```

```
gcaatccatg gaccttgtgg aacttgtgtc tcttttttccc acgctggctg gacttgcagg    3180
actgcaggtt ccacctcgct gccccgttcc ttcatttcac gttgagctgt cagagaagg    3240 caagaacctt ctgaagcatt ttcgattccg tgacttggaa gaggatccgt acctccctgg    3300
taatccccgt gaactgattg cctatagcca gtatccccgg ccttcagaca tccctcagtg    3360
gaattctgac aagccgagtt taaaagatat aaagatcatg ggctattcca tacgcaccat    3420
agactatagg tatactgtgt gggttggctt caatcctgat gaatttctag ctaacttttc    3480
tgacatccat gcaggggaac tgtattttgt ggattctgac ccattgcagg atcacaatat    3540
gtataatgat tcccaaggtg gagatctttt ccagttgttg atgccttgag aattcattta    3600
attcgagctc ggtacccggg aatcaattca ctcctcaggt gcaggctgcc tatcagaagg    3660
tggtggctgg tgtggccaat gccctggctc acaaatacca ctgagatctt tttccctctg    3720
ccaaaaatta tggggacatc atgaagcccc ttgagcatct gacttctggc taataaagga    3780
aattattttt cattgcaata gtgtgttgga attttttgtg tctctcactc ggaaggacat    3840
atgggagggc aaatcattta aaacatcaga atgagtattt ggtttagagt ttggcaacat    3900
atgcccatat gctggctgcc atgaacaaag gttggctata agaggtcat cagtatatga    3960 aacagccccc tgctgtccat tccttattcc atagaaaagc cttgacttga ggttagattt    4020
tttttatatt ttgttttgtg ttattttttt ctttaacatc cctaaaattt tccttacatg    4080
ttttactagc cagatttttc ctcctctcct gactactccc agtcatagct gtccctcttc    4140
tcttatggag atccctcgac ctgcagccca agctgtagat aagtagcatg cgggttaat    4200 cattaactac aaggaacccc tagtgatgga gttggccact ccctctctgc gcgctcgctc    4260
gctcactgag gccgcccggg ctttgcccgg gcggcctcag tgagcgagcg agcgcgcag    4319
```

<210> SEQ ID NO 5
<211> LENGTH: 1653
<212> TYPE: DNA
<213> ORGANISM: Artificial Sequence
<220> FEATURE:
<223> OTHER INFORMATION: ohIDS-version1

<400> SEQUENCE: 5

```
atgccccac ctagaaccgg aagaggattg ctctggctcg acttgtgct gtccagcgtg     60 tgtgtggccc tgggctcgga aacccaggcc aacagcacca ccgacgccct gaatgtgctg    120
ctgattatcg tggacgatct ccggccttcg ctgggctgct acggggataa gctggtccgc    180
tccccgaata tcgaccaact ggcttcacat agcctgcttt ccaaaacgc attcgcccaa    240 caagccgtgt gcgccccgag ccgcgtgtct ttcctcaccg gccggcgccc tgatactacc    300
cggctctacg acttcaacag ctactggaga gtgcacgcag gaaacttctc caccattcct    360
cagtacttta aggagaacgg ttacgtcacc atgagcgtgg ggaaggtgtt ccaccctgga    420
atttcctcca ccacaccga cgactcgcca tactcctggt cctttccccc ttaccaccca    480
tcatccgaga agtacgagaa caccaagacg tgcaggggcc cagacgggga actgcacgcg    540
aacctcctct gcccggtcga tgtgctggat gtgcccgaag gcaccctccc tgacaaacag    600
agcaccgaac aggccatcca gctcctcgag aagatgaaaa cttcagcctc cccgttcttt    660
ctggccgtgg gataccacaa gccgcatatc cccttccggt acccaaagga gttccagaag    720
ctgtaccccg tggagaacat tacccctggc cctgatcccg aagtgccgga cggcctgccg    780
cccgtggcat acaacccttg gatggacatc cgccagaggg aggatgtgca agccctgaac    840
atctccgtgc catacggtcc gatcccggtc gacttccagc ggaagattag gcagtcatat    900
```

| | |
|---|---:|
| ttcgcgtccg tgtcctactt ggacactcag gtcggacgcc tcctctccgc tctcgacgat | 960 |
| ctgcagctgg ccaactcgac cattatcgcg ttcacctcgg accatggttg ggctctgggc | 1020 |
| gaacacggag aatgggccaa gtacagcaat tcgatgtcg cgactcacgt gcccctgatc | 1080 |
| ttctacgtgc ccggacgcac agccagcttg cctgaagcgg gggaaaagct gttcccttac | 1140 |
| ctggatccct tcgactccgc ctctcaactt atggagccag gcagacagtc gatggacctg | 1200 |
| gtggaactcg tgtcactgtt ccctaccctc gccggtctgg ccggacttca ggtcccgcct | 1260 |
| cggtgcccgg tgccgtcctt ccacgtggag ctgtgtcgcg agggaaagaa cctcctgaaa | 1320 |
| cacttccggt tccgcgacct ggaggaagat ccctacttgc cgggcaaccc gagagaactt | 1380 |
| atcgcatact cccagtaccc tcgcccctcc gacatcccgc agtggaactc gacaagccg | 1440 |
| agcctgaagg acattaagat catggggtac tccatccgga ctattgacta tcggtacact | 1500 |
| gtgtgggtcg ggttcaaccc agatgagttt ctggccaact tctccgatat ccatgccgga | 1560 |
| gagctgtact tcgtggactc ggacccgctg caggaccaca acatgtacaa cgactcacag | 1620 |
| ggcggcgacc tgttccagtt gctgatgccc tga | 1653 |

<210> SEQ ID NO 6
<211> LENGTH: 7888
<212> TYPE: DNA
<213> ORGANISM: Artificial Sequence
<220> FEATURE:
<223> OTHER INFORMATION: pAAV-CAG-ohIDS-version1

<400> SEQUENCE: 6

| | |
|---|---:|
| cgcgtgccac catgccccca cctagaaccg gaagaggatt gctctggctc ggacttgtgc | 60 |
| tgtccagcgt gtgtgtggcc ctgggctcgg aaacccaggc caacagcacc accgacgccc | 120 |
| tgaatgtgct gctgattatc gtggacgatc tccggcctc gctgggctgc tacggggata | 180 |
| agctggtccg ctccccgaat atcgaccaac tggcttcaca tagcctgctt ttccaaaacg | 240 |
| cattcgccca caagccgtg tgcgcccga gccgcgtgtc tttcctcacc ggccggcgcc | 300 |
| ctgatactac ccggctctac gacttcaaca gctactggag agtgcacgca ggaaacttct | 360 |
| ccaccattcc tcagtacttt aaggagaacg gttacgtcac catgagcgtg gggaaggtgt | 420 |
| tccaccctgg aatttcctcc aaccacaccg acgactcgcc atactcctgg tccttttccc | 480 |
| cttaccaccc atcatccgag aagtacgaga caccaagac gtgcaggggc ccagacgggg | 540 |
| aactgcacgc gaacctcctc tgcccggtcg atgtgctgga tgtgcccgaa ggcaccctcc | 600 |
| ctgacaaaca gagcaccgaa caggccatcc agctcctcga aagatgaaa acttcagcct | 660 |
| ccccgttctt tctggccgtg ggataccaca agccgcatat ccccttccgg tacccaaagg | 720 |
| agttccagaa gctgtacccg ctggagaaca ttaccctggc tcctgatccc gaagtgccgg | 780 |
| acggcctgcc gccgtggca tacaaccctt ggatggacat ccgccagagg gaggatgtgc | 840 |
| aagccctgaa catctccgtg ccatacggtc cgatcccggt cgacttccag cggaagatta | 900 |
| ggcagtcata tttcgcgtcc gtgtcctact ggacactca ggtcggacgc ctcctctccg | 960 |
| ctctcgacga tctgcagctg gccaactcga ccattatcgc gttcacctcg gaccatggtt | 1020 |
| gggctctggg cgaacacgga gaatgggcca agtacagcaa tttcgatgtc gcgactcacg | 1080 |
| tgccctgat cttctacgtg cccggacgca cagccagctt gcctgaagcg ggggaaaagc | 1140 |
| tgttcccctta cctggatccc ttcgactccg cctctcaact tatggagcca ggcagacagt | 1200 |
| cgatggacct ggtggaactc gtgtcactgt tccctaccct cgccggtctg gccggacttc | 1260 |
| aggtcccgcc tcggtgcccg gtgccgtcct tccacgtgga gctgtgtcgc gagggaaaga | 1320 |

```
acctcctgaa acacttccgg ttccgcgacc tggaggaaga tccctacttg ccgggcaacc    1380
cgagagaact tatcgcatac tcccagtacc ctcgcccctc cgacatcccg cagtggaact    1440
ccgacaagcc gagcctgaag gacattaaga tcatgggtta ctccatccgg actattgact    1500
atcggtacac tgtgtgggtc gggttcaacc cagatgagtt tctggccaac ttctccgata    1560
tccatgccgg agagctgtac ttcgtggact cggacccgct gcaggaccac aacatgtaca    1620
acgactcaca gggcggcgac ctgttccagt tgctgatgcc ctgagaattc gagctcggta    1680
cccgggaatc aattcactcc tcaggtgcag gctgcctatc agaaggtggt ggctggtgtg    1740
gccaatgccc tggctcacaa ataccactga gatctttttc cctctgccaa aaattatggg    1800
gacatcatga agccccttga gcatctgact tctggctaat aaaggaaatt tattttcatt    1860
gcaatagtgt gttggaattt tttgtgtctc tcactcggaa ggacatatgg gagggcaaat    1920
catttaaaac atcagaatga gtatttggtt tagagtttgg aacatatgc ccatatgctg     1980
gctgccatga acaaaggttg gctataaaga ggtcatcagt atatgaaaca gcccctgct     2040
gtccattcct tattccatag aaaagccttg acttgaggtt agatttttt tatattttgt     2100
tttgtgttat ttttttcttt aacatcccta aaattttcct tacatgtttt actagccaga    2160
ttttcctcc tctcctgact actcccagtc atagctgtcc ctcttctctt atggagatcc     2220
ctcgacctgc agcccaagct gtagataagt agcatggcgg gttaatcatt aactacaagg    2280
aaccccctagt gatggagttg ccactccct ctctgcgcgc tcgctcgctc actgaggccg     2340
cccgggcttt gcccgggcgg cctcagtgag cgagcgagcg cgcagctgca ttaatgaatc    2400
ggccaacgcg cggggagagg cggtttgcgt attgggcgct cttccgcttc ctcgctcact    2460
gactcgctgc gctcggtcgt tcggctgcgg cgagcggtat cagctcactc aaaggcggta    2520
atacggttat ccacagaatc aggggataac gcaggaaaga acatgtgagc aaaaggccag    2580
caaaaggcca ggaaccgtaa aaaggccgcg ttgctggcgt ttttccatag gctccgcccc    2640
cctgacgagc atcacaaaaa tcgacgctca agtcagaggt ggcgaaaccc gacaggacta    2700
taaagatacc aggcgtttcc ccctggaagc tccctcgtgc gctctcctgt tccgaccctg    2760
ccgcttaccg gatacctgtc cgcctttctc ccttcgggaa gcgtggcgct ttctcatagc    2820
tcacgctgta ggtatctcag ttcggtgtag tcgttcgct ccaagctggg ctgtgtgcac     2880
gaaccccccg ttcagcccga ccgctgcgcc ttatccggta actatcgtct tgagtccaac    2940
ccggtaagac acgacttatc gccactggca gcagccactg gtaacaggat tagcagagcg    3000
aggtatgtag gcggtgctac agagttcttg aagtggtggc ctaactacgg ctacactaga    3060
agaacagtat ttggtatctg cgctctgctg aagccagtta ccttcggaaa aagagttggt    3120
agctcttgat ccggcaaaca aaccaccgct ggtagcggtg gtttttttgt ttgcaagcag    3180
cagattacgc gcagaaaaaa aggatctcaa gaagatcctt tgatcttttc tacggggtct    3240
gacgctcagt ggaacgaaaa ctcacgttaa gggattttgg tcatgagatt atcaaaaagg    3300
atcttcacct agatcctttt aaattaaaaa tgaagtttta aatcaatcta agtatatat     3360
gagtaaactt ggtctgacag ttaccaatgc ttaatcagtg aggcacctat ctcagcgatc    3420
tgtctatttc gttcatccat agttgcctga ctccccgtcg tgtagataac tacgatacgg    3480
gagggcttac catctggccc cagtgctgca atgataccgc gagacccacg ctcaccggct    3540
ccagatttat cagcaataaa ccagccagcc ggaagggccg agcgcagaag tggtcctgca    3600
actttatccg cctccatcca gtctattaat tgttgccggg aagctagagt aagtagttcg    3660
ccagttaata gtttgcgcaa cgttgttgcc attgctacag gcatcgtggt gtcacgctcg    3720
```

```
tcgtttggta tggcttcatt cagctccggt tcccaacgat caaggcgagt tacatgatcc    3780
cccatgttgt gcaaaaaagc ggttagctcc ttcggtcctc cgatcgttgt cagaagtaag    3840
ttggccgcag tgttatcact catggttatg gcagcactgc ataattctct tactgtcatg    3900
ccatccgtaa gatgcttttc tgtgactggt gagtactcaa ccaagtcatt ctgagaatag    3960
tgtatgcggc gaccgagttg ctcttgcccg gcgtcaatac gggataatac cgcgccacat    4020
agcagaactt taaaagtgct catcattgga aaacgttctt cggggcgaaa actctcaagg    4080
atcttaccgc tgttgagatc cagttcgatg taacccactc gtgcacccaa ctgatcttca    4140
gcatctttta ctttcaccag cgtttctggg tgagcaaaaa caggaaggca aaatgccgca    4200
aaaaagggaa taagggcgac acggaaatgt tgaatactca tactcttcct ttttcaatat    4260
tattgaagca tttatcaggg ttattgtctc atgagcggat acatatttga atgtatttag    4320
aaaaataaac aaataggggt tccgcgcaca tttccccgaa aagtgccacc tgacgtctaa    4380
gaaaccatta ttatcatgac attaacctat aaaaataggc gtatcacgag gccctttcgt    4440
ctcgcgcgtt tcggtgatga cggtgaaaac ctctgacaca tgcagctccc ggagacggtc    4500
acagcttgtc tgtaagcgga tgccgggagc agacaagccc gtcagggcgc gtcagcgggt    4560
gttggcgggt gtcggggctg gcttaactat gcggcatcag agcagattgt actgagagtg    4620
caccatatgc ggtgtgaaat accgcacaga tgcgtaagga gaaaataccg catcaggcga    4680
ttccaacatc aataaaatca tacaggcaag gcaaagaatt agcaaaatta agcaataaag    4740
cctcagagca taaagctaaa tcggttgtac caaaaacatt atgaccctgt aatacttttg    4800
cgggagaagc ctttatttca acgcaaggat aaaaattttt agaaccctca tatattttaa    4860
atgcaatgcc tgagtaatgt gtaggtaaag attcaaacgg gtgagaaagg ccggagacag    4920
tcaaatcacc atcaatatga tattcaaccg ttctagctga taaattcatg ccggagaggg    4980
tagctatttt tgagaggtct ctacaaaggc tatcaggtca ttgcctgaga gtctggagca    5040
aacaagagaa tcgatgaacg gtaatcgtaa aactagcatg tcaatcatat gtaccccggt    5100
tgataatcag aaaagcccca aaaacaggaa gattgtataa gcaaatattt aaattgtaag    5160
cgttaatatt ttgttaaaat tcgcgttaaa ttttttgttaa atcagctcat tttttaacca    5220
ataggccgaa atcggcaaaa tcccttataa atcaaaagaa tagaccgaga tagggttgag    5280
tgttgttcca gtttggaaca agagtccact attaaagaac gtggactcca acgtcaaagg    5340
gcgaaaaacc gtctatcagg gcgatggccc actacgtgaa ccatcaccct aatcaagttt    5400
tttggggtcg aggtgccgta aagcactaaa tcggaaccct aaagggagcc ccgatttag    5460 agcttgacgg ggaaagccgg cgaacgtggc gagaaaggaa gggaagaaag cgaaaggagc    5520
gggcgctagg gcgctggcaa gtgtagcggt cacgctgcgc gtaaccacca cacccgccgc    5580
gcttaatgcg ccgctacagg gcgcgtacta tggttgcttt gacgagcacg tataacgtgc    5640
tttcctcgtt agaatcagag cgggagctaa acaggaggcc gattaaaggg attttagaca    5700
ggaacggtac gccagaatcc tgagaagtgt ttttataatc agtgaggcca ccgagtaaaa    5760
gagtctgtcc atcacgcaaa ttaaccgttg tcgcaatact tctttgatta gtaataacat    5820
cacttgcctg agtagaagaa ctcaaactat cggccttgct ggtaatatcc agaacaatat    5880
taccgccagc cattgcaacg gaatcgccat tcgccattca ggctgcgcaa ctgttgggaa    5940
gggcgatcgg tgcgggcctc ttcgctatta cgccagctgc gcgctcgctc gctcactgag    6000
gccgcccggg caaagcccgg gcgtcgggcg acctttggtc gcccggcctc agtgagcgag    6060
cgagcgcgca gagagggagt ggccaactcc atcactaggg gttccttgta gttaatgatt    6120
```

| | |
|---|---|
| aacccgccat gctacttatc tactcgacat tgattattga ctagttatta atagtaatca | 6180 |
| attacggggt cattagttca tagcccatat atggagttcc gcgttacata acttacggta | 6240 |
| aatggcccgc ctggctgacc gcccaacgac ccccgcccat tgacgtcaat aatgacgtat | 6300 |
| gttcccatag taacgccaat agggactttc cattgacgtc aatgggtgga gtatttacgg | 6360 |
| taaactgccc acttggcagt acatcaagtg tatcatatgc caagtacgcc ccctattgac | 6420 |
| gtcaatgacg gtaaatggcc cgcctggcat tatgcccagt acatgacctt atgggacttt | 6480 |
| cctacttggc agtacatcta cgtattagtc atcgctatta ccatggtcga ggtgagcccc | 6540 |
| acgttctgct tcactctccc catctccccc cctccccac ccccaatttt gtatttattt | 6600 |
| attttttaat tattttgtgc agcgatgggg gcggggggggg gggggggcg cgcgccaggc | 6660 |
| ggggcgggc ggggcgaggg gcggggcggg gcgaggcgga gaggtgcggc ggcagccaat | 6720 |
| cagagcggcg cgctccgaaa gtttcctttt atggcgaggc ggcggcggcg gcggccctat | 6780 |
| aaaaagcgaa gcgcgcggcg gcgggagtc gctgcgttgc cttcgccccg tgccccgctc | 6840 |
| cgccgccgcc tcgcgccgcc cgccccggct ctgactgacc gcgttactcc cacaggtgag | 6900 |
| cgggcgggac ggcccttctc ctccgggctg taattagcgc ttggtttaat gacggcttgt | 6960 |
| ttcttttctg tggctgcgtg aaagccttga ggggctccgg gagggccctt tgtgcggggg | 7020 |
| gagcggctcg gggggtgcgt gcgtgtgtgt gtgcgtgggg agcgccgcgt gcggctccgc | 7080 |
| gctgcccggc ggctgtgagc gctgcgggcg cggcgcgggg ctttgtgcgc tccgcagtgt | 7140 |
| gcgcgagggg agcgcggccg ggggcggtgc cccgcggtgc gggggggct gcgaggggaa | 7200 |
| caaaggctgc gtgcggggtg tgtgcgtggg gggtgagca gggggtgtgg gcgcgtcggt | 7260 |
| cgggctgcaa ccccccctgc acccccctcc ccgagttgct gagcacggcc cggcttcggg | 7320 |
| tgcgggctc cgtacggggc gtggcgcggg gctcgccgtg ccgggcgggg ggtgcggca | 7380 |
| ggtgggggtg ccggcggggg cggggccgcc tcgggccggg gagggctcgg gggaggggcg | 7440 |
| cggcggcccc cggagcgccg gcggctgtcg aggcgcggcg agccgcagcc attgcctttt | 7500 |
| atggtaatcg tgcgagaggg cgcagggact tcctttgtcc caaatctgtg cggagccgaa | 7560 |
| atctgggagg cgccgccgca ccccctctag cgggcgcggg gcgaagcggt gcggcgccgg | 7620 |
| caggaaggaa atgggcgggg agggccttcg tgcgtcgccg cgccgccgtc cccttctccc | 7680 |
| tctccagcct cggggctgtc cgcggggga cggctgcctt cggggggac ggggcagggc | 7740 |
| ggggttcggc ttctggcgtg tgaccggcgg ctctagagcc tctgctaacc atgttcatgc | 7800 |
| cttcttcttt ttcctacagc tcctgggcaa cgtgctggtt attgtgctgt ctcatcattt | 7860 |
| tggcaaagaa ttgattaatt cgagcgaa | 7888 |

<210> SEQ ID NO 7
<211> LENGTH: 4307
<212> TYPE: DNA
<213> ORGANISM: Artificial Sequence
<220> FEATURE:
<223> OTHER INFORMATION: AAV9-CAG-ohIDS-version1

<400> SEQUENCE: 7

| | |
|---|---|
| attacgccag ctgcgcgctc gctcgctcac tgaggccgcc cgggcaaagc ccgggcgtcg | 60 |
| ggcgaccttt ggtcgcccgg cctcagtgag cgagcgagcg cgcagagagg gagtggccaa | 120 |
| ctccatcact aggggttcct tgtagttaat gattaacccg ccatgctact tatctactcg | 180 |
| acattgatta ttgactagtt attaatagta atcaattacg ggtcattag ttcatagccc | 240 |
| atatatggag ttccgcgtta cataacttac ggtaaatggc ccgcctggct gaccgcccaa | 300 |

```
cgaccccgc ccattgacgt caataatgac gtatgttccc atagtaacgc caatagggac      360
tttccattga cgtcaatggg tggagtattt acggtaaact gcccacttgg cagtacatca      420
agtgtatcat atgccaagta cgcccctat tgacgtcaat gacggtaaat ggcccgcctg       480
gcattatgcc cagtacatga ccttatggga ctttcctact tggcagtaca tctacgtatt      540
agtcatcgct attaccatgg tcgaggtgag ccccacgttc tgcttcactc tccccatctc      600
ccccccctcc ccaccccaa ttttgtattt atttattttt taattatttt gtgcagcgat       660
gggggcgggg gggggggggg ggcgcgcgcc aggcggggcg gggcggggcg aggggcgggg      720
cggggcgagg cggagaggtg cggcggcagc aatcagagc ggcgcgctcc gaaagtttcc       780
ttttatggcg aggcggcggc ggcggcggcc ctataaaaag cgaagcgcgc ggcgggcggg      840
agtcgctgcg ttgccttcgc cccgtgcccc gctccgccgc cgcctcgcgc cgcccgcccc      900
ggctctgact gaccgcgtta ctcccacagg tgagcgggcg ggacggccct tctcctccgg      960
gctgtaatta gcgcttggtt taatgacggc ttgtttcttt tctgtggctg cgtgaaagcc     1020 ttgagggct ccgggagggc cctttgtgcg ggggagcgg ctcggggggt gcgtgcgtgt       1080
gtgtgtgcgt gggagcgcc gcgtgcggct ccgcgctgcc cggcggctgt gagcgctgcg      1140
ggcgcggcgc ggggctttgt gcgctccgca gtgtgcgcga gggagcgcg gccggggggcg     1200 gtgccccgcg gtgcggggg ggctgcgagg ggaacaaagg ctgcgtgcgg ggtgtgtgcg      1260
tgggggggtg agcaggggt gtgggcgcgt cggtcgggct gcaacccccc ctgcacccccc     1320 ctccccgagt tgctgagcac ggcccggctt cgggtgcggg gctccgtacg gggcgtggcg     1380
cggggctcgc cgtgccgggc gggggtggc ggcaggtggg ggtgccgggc ggggcggggc      1440
cgcctcgggc cggggagggc tcgggggagg ggcgcggcgg ccccggagc gccggcggct      1500 gtcgaggcgc ggcgagccgc agccattgcc ttttatggta atcgtgcgag agggcgcagg     1560
gacttccttt gtcccaaatc tgtgcggagc cgaaatctgg gaggcgccgc cgcaccccct     1620
ctagcgggcg cgggggcgaag cggtgcgcg ccggcaggaa ggaaatgggc ggggagggcc     1680
ttcgtgcgtc gccgcgccgc cgtcccctttc tccctctcca gcctcggggc tgtccgcggg     1740
gggacggctg ccttcggggg ggacggggca gggcggggtt cggcttctgg cgtgtgaccg     1800
gcggctctag agcctctgct aaccatgttc atgccttctt cttttttccta cagctcctgg     1860 gcaacgtgct ggttattgtg ctgtctcatc attttggcaa agaattgatt aattcgagcg     1920
aacgcgtgcc accatgcccc cacctagaac cggaagagga ttgctctggc tcggacttgt     1980
gctgtccagc gtgtgtgtgg ccctgggctc ggaaacccag gccaacagca ccaccgacgc     2040
cctgaatgtg ctgctgatta tcgtggacga tctccggcct tcgctgggct gctacgggga     2100
taagctggtc cgctccccga atatcgacca actggcttca catagcctgc ttttccaaaa     2160
cgcattcgcc caacaagccg tgtgcgcccc gagccgcgtg tctttcctca ccggccggcg     2220
ccctgatact acccggctct acgacttcaa cagctactgg agagtgcacg caggaaactt     2280
ctccaccatt cctcagtact ttaaggagaa cggttacgtc accatgagcg tggggaaggt     2340
gttccaccct ggaatttcct ccaaccacac cgacgactcg ccatactcct ggtcctttcc     2400
cccttaccac ccatcatccg agaagtacga gaacaccaag acgtgcaggg gcccagacgg     2460
ggaactgcac gcgaacctcc tctgcccggt cgatgtgctg gatgtgcccg aaggcacact     2520
ccctgacaaa cagagcaccg aacaggccat ccagctcctc gagaagatga aaacttcagc     2580
ctccccgttc tttctggccg tgggatacca caagccgcat atccccttcc ggtacccaaa     2640
ggagttccag aagctgtacc cgctggagaa cattaccctg gctcctgatc ccgaagtgcc     2700
```

```
ggacggcctg ccgcccgtgg catacaaccc ttggatggac atccgccaga gggaggatgt    2760
gcaagccctg aacatctccg tgccatacgg tccgatcccg gtcgacttcc agcggaagat    2820
taggcagtca tatttcgcgt ccgtgtccta cttggacact caggtcggac gcctcctctc    2880
cgctctcgac gatctgcagc tggccaactc gaccattatc gcgttcacct cggaccatgg    2940
ttgggctctg ggcgaacacg gagaatgggc caagtacagc aatttcgatg tcgcgactca    3000
cgtgcccctg atcttctacg tgcccggacg cacagccagc ttgcctgaag cgggggaaaa    3060
gctgttccct tacctggatc ccttcgactc cgcctctcaa cttatggagc caggcagaca    3120
gtcgatggac ctggtggaac tcgtgtcact gttccctacc ctcgccggtc tggccggact    3180
tcaggtcccg cctcggtgcc cggtgccgtc cttccacgtg gagctgtgtc gcagggaaa     3240 gaacctcctg aaacacttcc ggttccgcga cctggaggaa gatccctact gcccgggcaa    3300
cccgagagaa cttatcgcat actcccagta ccctcgcccc tccgacatcc cgcagtggaa    3360
ctccgacaag ccgagcctga aggacattaa gatcatgggg tactccatcc ggactattga    3420
ctatcggtac actgtgtggg tcgggttcaa cccagatgag tttctggcca acttctccga    3480
tatccatgcc ggagagctgt acttcgtgga ctcggacccg ctgcaggacc acaacatgta    3540
caacgactca cagggcggcg acctgttcca gttgctgatg ccctgagaat tcgagctcgg    3600
tacccgggaa tcaattcact cctcaggtgc aggctgccta tcagaaggtg gtggctggtg    3660
tggccaatgc cctggctcac aaataccact gagatctttt tccctctgcc aaaaattatg    3720
gggacatcat gaagccccct tgagcatctga cttctggcta ataaaggaaa tttattttca    3780
ttgcaatagt gtgttggaat tttttgtgtc tctcactcgg aaggacatat gggagggcaa    3840
atcatttaaa acatcagaat gagtatttgg tttagagttt ggcaacatat gcccatatgc    3900
tggctgccat gaacaaaggt tggctataaa gaggtcatca gtatatgaaa cagcccctg     3960 ctgtccattc cttattccat agaaaagcct tgacttgagg ttagattttt tttatatttt    4020
gttttgtgtt attttttctt ttaacatccc taaaattttc cttacatgtt ttactagcca    4080
gatttttcct cctctcctga ctactcccag tcatagctgt ccctcttctc ttatggagat    4140
ccctcgacct gcagcccaag ctgtagataa gtagcatggc gggttaatca ttaactacaa    4200 ggaacccta gtgatggagt tggccactcc ctctctgcgc gctcgctcgc tcactgaggc     4260
cgcccgggct tgcccgggc ggcctcagtg agcgagcgag cgcgcag                   4307
```

<210> SEQ ID NO 8
<211> LENGTH: 1653
<212> TYPE: DNA
<213> ORGANISM: Artificial Sequence
<220> FEATURE:
<223> OTHER INFORMATION: ohIDS-version2

<400> SEQUENCE: 8

```
atgcctcctc ctagaactgg aagggggctg ctgtggctgg ggctggtcct gtcatcagtg      60
tgtgtcgctc tgggctccga gactcaggca aactccacca cagacgccct gaatgtgctg     120
ctgatcattg tcgacgatct gcgaccttcc ctggggtgct acggcgacaa gctggtgagg     180
tctccaaaca tcgatcagct ggcttcacac agcctgctgt tccagaatgc ctttgctcag     240
caggcagtgt gtgcaccatc acgggtcagc ttcctgaccg gaaggagacc tgacactacc     300
aggctgtacg attttaactc atattggaga gtgcatgccg gaaatttcag caccatccca     360
cagtacttta aggagaacgg ctatgtgaca atgtccgtgg aaaagtctt ccaccccggc      420 attagctcca atcatacaga cgattctcca tactcctggt cttttccccc ttatcacccc     480
```

```
tctagtgaga agtacgaaaa cacaaaaact tgcaggggac cagacgggga gctgcatgca      540
aatctgctgt gtcccgtgga cgtcctggat gtgcccgaag cacactgcc  tgataagcag      600
agcactgagc aggccattca gctgctggaa aagatgaaaa caagtgcttc acccttcttt      660
ctggcagtgg gatatcacaa accacatatc cccttcagat atcccaagga gtttcagaaa      720
ctgtacccctc tggaaaacat tactctggct cccgaccctg aggtgcctga tggactgcca      780
cccgtcgcat ataacccatg gatggacatc cggcagcgcg aggatgtgca ggccctgaat      840
atcagtgtcc cttacgggcc aattcccgtg gacttccaga gaaagattcg gcagtcttac      900
tttgccagcg tctcctatct ggatactcaa gtgggacgac tgctgagcgc tctggacgat      960
ctgcagctgg ccaacagcac catcattgct ttcacatccg accacggatg ggctctggga     1020
gagcatggag aatgggcaaa gtatagcaat ttcgatgtgg ccactcacgt cccactgatc     1080
ttttacgtgc ccggccgaac cgcatccctg ccagaggctg agaaaaaact gttcccttac     1140
ctggacccat tgattctgc  tagtcagctg atggagcctg ccgacagtc  tatggacctg     1200
gtggaactgg tcagtctgtt ccctacactg gctggactgg caggactgca ggtgcctcca     1260
agatgccctg tgccatcttt tcacgtcgag ctgtgtcggg aaggcaagaa cctgctgaaa     1320
catttcaggt tcagggacct ggaggaagat ccttatctgc caggaaatcc cagggagctg     1380
atcgcctaca gtcagtatcc ccgcccttca gacattcctc agtggaactc cgacaagcca     1440
tctctgaagg atatcaaaat tatgggatac agcatccgca ctattgatta ccgatatacc     1500
gtgtgggtcg ggttcaaccc cgacgagttc ctggcaaatt ttagtgatat ccacgccggc     1560
gaactgtatt ttgtggactc agatcctctg caggaccata acatgtacaa tgacagccag     1620
ggcggagatc tgttccagct gctgatgcca tga                                  1653

<210> SEQ ID NO 9
<211> LENGTH: 7888
<212> TYPE: DNA
<213> ORGANISM: Artificial Sequence
<220> FEATURE:
<223> OTHER INFORMATION: pAAV-CAG-ohIDS-version2

<400> SEQUENCE: 9
cgcgtgccac catgcctcct cctagaactg aaggggggct gctgtggctg ggctggtcc       60
tgtcatcagt gtgtgtcgct ctgggctccg agactcaggc aaaactccac cacagacgccc     120
tgaatgtgct gctgatcatt gtcgacgatc tgcgaccttc cctggggtgc tacggcgaca     180
agctggtgag gtctccaaac atcgatcagc tggcttcaca cagcctgctg ttccagaatg     240
cctttgctca gcaggcagtg tgtgcaccat cacgggtcag cttcctgacc ggaaggagac     300
ctgacactac caggctgtac gattttaact catattggag agtgcatgcc gggaattttca     360
gcaccatccc acagtacttt aaggagaacg gctatgtgac aatgtccgtg ggaaaagtct     420
tccacccggg cattagctcc aatcatacag acgattctcc atactcctgg tcttttcccc     480
cttatcaccc ctctagtgag aagtacgaaa acacaaaaac ttgcaggga  ccagacgggg     540
agctgcatgc aaatctgctg tgtcccgtgg acgtcctgga tgtgcccgaa ggcacactgc     600
ctgataagca gagcactgag caggccattc agctgctgga aaagatgaaa acaagtgctt     660
caccccttctt tctggcagtg ggatatcaca aaccacatat ccccttcaga tatcccaagg     720
agtttcagaa actgtaccct ctggaaaaca ttactctggc tccgaccct  gaggtgcctg     780
atggactgcc acccgtcgca tataacccat ggatggacat ccggcagcgc gaggatgtgc     840
aggccctgaa tatcagtgtc ccttacgggc caattcccgt ggacttccag agaaagattc     900
```

```
ggcagtctta cttttgccagc gtctcctatc tggatactca agtgggacga ctgctgagcg      960
ctctggacga tctgcagctg gccaacagca ccatcattgc tttcacatcc gaccacggat     1020
gggctctggg agagcatgga gaatgggcaa agtatagcaa tttcgatgtg ccactcacg      1080
tcccactgat cttttacgtg cccggccgaa ccgcatccct gccagaggct ggagaaaaac     1140
tgttccctta cctggaccca tttgattctg ctagtcagct gatggagcct ggccgacagt     1200
ctatggacct ggtggaactg gtcagtctgt tccctacact ggctggactg gcaggactgc     1260
aggtgcctcc aagatgccct gtgccatctt ttcacgtcga gctgtgtcgg aaggcaaga      1320
acctgctgaa acatttcagg ttcagggacc tggaggaaga tccttatctg ccaggaaatc     1380
ccagggagct gatcgcctac agtcagtatc cccgcccttc agacattcct cagtggaact     1440
ccgacaagcc atctctgaag gatatcaaaa ttatgggata cagcatccgc actattgatt     1500
accgatatac cgtgtgggtc gggttcaacc ccgacgagtt cctggcaaat tttagtgata     1560
tccacgccgg cgaactgtat tttgtggact cagatcctct gcaggaccat aacatgtaca     1620
atgacagcca gggcggagat ctgttccagc tgctgatgcc atgagaattc gagctcggta     1680
cccgggaatc aattcactcc tcaggtgcag gctgcctatc agaaggtggt ggctggtgtg     1740
gccaatgccc tggctcacaa ataccactga gatctttttc cctctgccaa aaattatggg     1800
gacatcatga agcccttga gcatctgact tctggctaat aaaggaaatt tattttcatt      1860
gcaatagtgt gttggaattt tttgtgtctc tcactcggaa ggacatatgg agggcaaat     1920
catttaaaac atcagaatga gtatttggtt tagagtttgg caacatatgc ccatatgctg     1980
gctgccatga acaaaggttg gctataaaga ggtcatcagt atatgaaaca gcccctgct     2040
gtccattcct tattccatag aaaagccttg acttgaggtt agatttttt tatattttgt     2100
tttgtgttat ttttttcttt aacatcccta aaatttttcct tacatgtttt actagccaga     2160
tttttcctcc tctcctgact actcccagtc atagctgtcc ctcttctctt atggagatcc     2220
ctcgacctga gcccaagct gtagataagt agcatggcgg gttaatcatt aactacaagg      2280
aaccctagt gatggagttg ccactccct ctctgcgcgc tcgctcgctc actgaggccg      2340
cccgggcttt gcccggcgg cctcagtgag cgagcgagcg cgcagctgca ttaatgaatc      2400
ggccaacgcg cggggagagg cggtttgcgt attgggcgct cttccgcttc ctcgctcact     2460
gactcgctgc gctcggtcgt tcggctgcgg cgagcggtat cagctcactc aaaggcggta     2520
atacggttat ccacagaatc aggggataac gcaggaaaga acatgtgagc aaaaggccag     2580
caaaaggcca ggaaccgtaa aaaggccgcg ttgctggcgt ttttccatag gctccgcccc     2640
cctgacgagc atcacaaaaa tcgacgctca agtcagaggt ggcgaaaccc gacaggacta     2700
taaagatacc aggcgtttcc ccctggaagc tccctcgtgc gctctcctgt tccgaccctg     2760
ccgcttaccg gatacctgtc cgcctttctc ccttcgggaa gcgtggcgct ttctcatagc     2820
tcacgctgta ggtatctcag ttcggtgtag gtcgttcgct ccaagctggg ctgtgtgcac     2880
gaaccccccg ttcagcccga ccgctgcgcc ttatccggta actatcgtct tgagtccaac     2940
ccggtaagac acgacttatc gccactggca gcagccactg gtaacaggat tagcagagcg     3000
aggtatgtag gcggtgctac agagttcttg aagtggtggc ctaactacgg ctacactaga     3060
agaacagtat ttggtatctg cgctctgctg aagccagtta ccttcggaaa aagagttggt     3120
agctcttgat ccggcaaaca aaccaccgct ggtagcggtg gtttttttgt ttgcaagcag     3180
cagattacgc gcagaaaaaa aggatctcaa gaagatcctt tgatctttc tacgggtct      3240
gacgctcagt ggaacgaaaa ctcacgttaa gggattttgg tcatgagatt atcaaaaagg     3300
```

```
atcttcacct agatccttt aaattaaaaa tgaagttta aatcaatcta aagtatatat    3360
gagtaaactt ggtctgacag ttaccaatgc ttaatcagtg aggcacctat ctcagcgatc    3420
tgtctatttc gttcatccat agttgcctga ctccccgtcg tgtagataac tacgatacgg    3480
gagggcttac catctggccc cagtgctgca atgataccgc gagacccacg ctcaccggct    3540
ccagatttat cagcaataaa ccagccagcc ggaagggccg agcgcagaag tggtcctgca    3600
actttatccg cctccatcca gtctattaat tgttgccggg aagctagagt aagtagttcg    3660
ccagttaata gtttgcgcaa cgttgttgcc attgctacag gcatcgtggt gtcacgctcg    3720
tcgtttggta tggcttcatt cagctccggt tcccaacgat caaggcgagt tacatgatcc    3780
cccatgttgt gcaaaaaagc ggttagctcc ttcggtcctc cgatcgttgt cagaagtaag    3840
ttggccgcag tgttatcact catggttatg gcagcactgc ataattctct tactgtcatg    3900
ccatccgtaa gatgcttttc tgtgactggt gagtactcaa ccaagtcatt ctgagaatag    3960
tgtatgcggc gaccgagttg ctcttgcccg gcgtcaatac gggataatac cgcgccacat    4020
agcagaactt taaaagtgct catcattgga aaacgttctt cggggcgaaa actctcaagg    4080
atcttaccgc tgttgagatc cagttcgatg taacccactc gtgcacccaa ctgatcttca    4140
gcatctttta ctttcaccag cgtttctggg tgagcaaaaa caggaaggca aaatgccgca    4200
aaaaagggaa taagggcgac acggaaatgt tgaatactca tactcttcct ttttcaatat    4260
tattgaagca tttatcaggg ttattgtctc atgagcggat acatatttga atgtatttag    4320
aaaaataaac aaataggggt tccgcgcaca tttccccgaa aagtgccacc tgacgtctaa    4380
gaaaccatta ttatcatgac attaacctat aaaaataggc gtatcacgag gccctttcgt    4440
ctcgcgcgtt tcggtgatga cggtgaaaac ctctgacaca tgcagctccc ggagacggtc    4500
acagcttgtc tgtaagcgga tgccgggagc agacaagccc gtcagggcgc gtcagcgggt    4560
gttggcgggt gtcggggctg gcttaactat gcggcatcag agcagattgt actgagagtg    4620
caccatatgc ggtgtgaaat accgcacaga tgcgtaagga gaaaataccg catcaggcga    4680
ttccaacatc aataaatca tacaggcaag gcaaagaatt agcaaaatta agcaataaag    4740
cctcagagca taaagctaaa tcggttgtac caaaaacatt atgaccctgt aatacttttg    4800
cgggagaagc ctttatttca acgcaaggat aaaaatttt agaaccctca tatatttaa    4860
atgcaatgcc tgagtaatgt gtaggtaaag attcaaacgg gtgagaaagg ccggagacag    4920
tcaaatcacc atcaatatga tattcaaccg ttctagctga taaattcatg ccggagaggg    4980
tagctatttt tgagaggtct ctacaaaggc tatcaggtca ttgcctgaga gtctggagca    5040
aacaagagaa tcgatgaacg gtaatcgtaa aactagcatg tcaatcatat gtaccccggt    5100
tgataatcag aaaagcccca aaacaggaa gattgtataa gcaaatattt aaattgtaag    5160
cgttaatatt ttgttaaaat tcgcgttaaa tttttgttaa atcagctcat ttttaacca    5220
ataggccgaa atcggcaaaa tcccttataa atcaaaagaa tagaccgaga tagggttgag    5280
tgttgttcca gtttggaaca agagtccact attaagaac gtggactcca acgtcaaagg    5340
gcgaaaaacc gtctatcagg gcgatggccc actacgtgaa ccatcaccct aatcaagttt    5400
tttggggtcg aggtgccgta aagcactaaa tcggaaccct aaaggagcc cccgatttag    5460
agcttgacgg ggaaagccgg cgaacgtggc gagaaaggaa gggaagaaag cgaaaggagc    5520
gggcgctagg gcgctggcaa gtgtagcggt cacgctgcgc gtaaccacca cacccgccgc    5580
gcttaatgcg ccgctacagg gcgcgtacta tggttgcttt gacgagcacg tataacgtgc    5640
tttcctcgtt agaatcagag cgggagctaa acaggaggcc gattaaaggg attttagaca    5700
```

```
ggaacggtac gccagaatcc tgagaagtgt ttttataatc agtgaggcca ccgagtaaaa    5760
gagtctgtcc atcacgcaaa ttaaccgttg tcgcaatact tctttgatta gtaataacat    5820
cacttgcctg agtagaagaa ctcaaactat cggccttgct ggtaatatcc agaacaatat    5880
taccgccagc cattgcaacg gaatcgccat tcgccattca ggctgcgcaa ctgttgggaa    5940
gggcgatcgg tgcgggcctc ttcgctatta cgccagctgc gcgctcgctc gctcactgag    6000
gccgcccggg caaagcccgg gcgtcgggcg acctttggtc gcccggcctc agtgagcgag    6060
cgagcgcgca gagagggagt ggccaactcc atcactaggg gttccttgta gttaatgatt    6120
aacccgccat gctacttatc tactcgacat tgattattga ctagttatta atagtaatca    6180
attacggggt cattagttca tagcccatat atggagttcc gcgttacata acttacggta    6240
aatggcccgc ctggctgacc gcccaacgac ccccgcccat tgacgtcaat aatgacgtat    6300
gttcccatag taacgccaat agggactttc cattgacgtc aatgggtgga gtatttacgg    6360
taaactgccc acttggcagt acatcaagtg tatcatatgc caagtacgcc ccctattgac    6420
gtcaatgacg gtaaatggcc cgcctggcat tatgcccagt acatgacctt atgggacttt    6480
cctacttggc agtacatcta cgtattagtc atcgctatta ccatggtcga ggtgagcccc    6540
acgttctgct tcactctccc catctccccc ccctccccac cccaatttt gtatttattt    6600 atttttaat tatttgtgc agcgatgggg gcggggggg ggggggggcg cgcgccaggc       6660 ggggcgggc gggcgaggg gcgggcggg gcgaggcgga gaggtgcggc ggcagccaat       6720
cagagcggcg cgctccgaaa gtttcctttt atggcgaggc ggcggcggcg gcggccctat    6780
aaaaagcgaa gcgcgcggcg gcgggagtc gctgcgttgc cttcgccccg tgccccgctc    6840
cgccgccgcc tcgcgccgcc cgccccggct ctgactgacc gcgttactcc cacaggtgag    6900
cgggcgggac ggcccttctc ctccgggctg taattagcgc ttggtttaat gacggcttgt    6960
ttcttttctg tggctgcgtg aaagccttga ggggctccgg gagggccctt tgtgcggggg    7020
gagcggctcg gggggtgcgt gcgtgtgtgt gtgcgtgggg agcgccgcgt gcggctccgc    7080
gctgcccggc ggctgtgagc gctgcgggcg cggcgcgggg ctttgtgcgc tccgcagtgt    7140
gcgcgagggg agcgcggccg ggggcggtgc cccgcggtgc ggggggggct gcgaggggaa    7200
caaaggctgc gtgcggggtg tgtgcgtggg ggggtgagca gggggtgtgg gcgcgtcggt    7260
cgggctgcaa cccccctgc accccctcc ccgagttgct gagcacggcc cggcttcggg       7320
tgcggggctc cgtacggggc gtggcgcggg gctcgccgtg ccgggcgggg ggtggcggca    7380 ggtggggtg ccgggcgggg cggggccgcc tcggccgggg gagggctcgg ggaggggcg       7440 cggcggcccc cggagcgccg gcggctgtcg aggcgcggcg agccgcagcc attgcctttt    7500
atggtaatcg tgcgagaggg cgcagggact tcctttgtcc caaatctgtg cggagccgaa    7560
atctgggagg cgccgccgca cccctctag cgggcgcggg gcgaagcggt gcggcgccgg      7620
caggaaggaa atggcgggg agggccttcg tgcgtcgccg cgccgccgtc cccttctccc      7680
tctccagcct cggggctgtc cgcggggga cggctgcctt cgggggggac ggggcagggc     7740
ggggttcggc ttctggcgtg tgaccggcgg ctctagagcc tctgctaacc atgttcatgc    7800
cttcttcttt ttcctacagc tcctgggcaa cgtgctggtt attgtgctgt ctcatcattt    7860
tggcaaagaa ttgattaatt cgagcgaa                                        7888

<210> SEQ ID NO 10
<211> LENGTH: 4307
<212> TYPE: DNA
<213> ORGANISM: Artificial Sequence
```

<220> FEATURE:
<223> OTHER INFORMATION: AAV9-CAG-ohIDS-version2

<400> SEQUENCE: 10

| | | | | | | |
|---|---|---|---|---|---|---|
| attacgccag | ctgcgcgctc | gctcgctcac | tgaggccgcc | cgggcaaagc | ccgggcgtcg | 60 |
| ggcgaccttt | ggtcgcccgg | cctcagtgag | cgagcgagcg | cgcagagagg | gagtggccaa | 120 |
| ctccatcact | aggggttcct | tgtagttaat | gattaacccg | ccatgctact | tatctactcg | 180 |
| acattgatta | ttgactagtt | attaatagta | atcaattacg | gggtcattag | ttcatagccc | 240 |
| atatatggag | ttccgcgtta | cataacttac | ggtaaatggc | ccgcctggct | gaccgcccaa | 300 |
| cgacccccgc | ccattgacgt | caataatgac | gtatgttccc | atagtaacgc | caatagggac | 360 |
| tttccattga | cgtcaatggg | tggagtattt | acggtaaact | gcccacttgg | cagtacatca | 420 |
| agtgtatcat | atgccaagta | cgccccctat | tgacgtcaat | gacggtaaat | ggcccgcctg | 480 |
| gcattatgcc | cagtacatga | ccttatggga | ctttcctact | tggcagtaca | tctacgtatt | 540 |
| agtcatcgct | attaccatgg | tcgaggtgag | ccccacgttc | tgcttcactc | tccccatctc | 600 |
| ccccccctcc | ccacccccaa | ttttgtattt | atttattttt | taattatttt | gtgcagcgat | 660 |
| gggggcgggg | gggggggggg | ggcgcgcgcc | aggcggggcg | gggcggggcg | aggggcgggg | 720 |
| cggggcgagg | cggagaggtg | cggcggcagc | caatcagagc | ggcgcgctcc | gaaagtttcc | 780 |
| ttttatggcg | aggcggcggc | ggcggcggcc | ctataaaaag | cgaagcgcgc | ggcgggcggg | 840 |
| agtcgctgcg | ttgccttcgc | cccgtgcccc | gctccgccgc | cgcctcgcgc | cgcccgcccc | 900 |
| ggctctgact | gaccgcgtta | ctcccacagg | tgagcgggcg | ggacggccct | tctcctccgg | 960 |
| gctgtaatta | gcgcttggtt | taatgacggc | ttgtttcttt | tctgtggctg | cgtgaaagcc | 1020 |
| ttgaggggct | ccgggagggc | cctttgtgcg | ggggagcgg | ctcggggggt | gcgtgcgtgt | 1080 |
| gtgtgtgcgt | ggggagcgcc | gcgtgcggct | ccgcgctgcc | cggcggctgt | gagcgctgcg | 1140 |
| ggcgcggcgc | ggggctttgt | gcgctccgca | gtgtgcgcga | ggggagcgcg | gccggggcg | 1200 |
| gtgccccgcg | gtgcgggggg | ggctgcgagg | ggaacaaagg | ctgcgtgcgg | ggtgtgtgcg | 1260 |
| tgggggggtg | agcaggggt | gtgggcgcgt | cggtcgggct | gcaacccccc | ctgcaccccc | 1320 |
| ctcccccgagt | tgctgagcac | ggcccggctt | cgggtgcggg | gctccgtacg | gggcgtggcg | 1380 |
| cggggctcgc | cgtgccgggc | ggggggtggc | ggcaggtggg | ggtgccgggc | ggggcgggc | 1440 |
| cgcctcgggc | cggggagggc | tcggggagg | gcgcggcgg | ccccggagc | gccggcggct | 1500 |
| gtcgaggcgc | ggcgagccgc | agccattgcc | ttttatggta | atcgtgcgag | agggcgcagg | 1560 |
| gacttccttt | gtcccaaatc | tgtgcggagc | cgaaatctgg | gaggcgccgc | cgcacccct | 1620 |
| ctagcgggcg | cggggcgaag | cggtgcgcg | ccggcaggaa | ggaaatgggc | ggggagggcc | 1680 |
| ttcgtgcgtc | gccgcgccgc | cgtcccctc | tccctctcca | gcctcggggc | tgtccgcggg | 1740 |
| gggacggctg | ccttcggggg | ggacggggca | gggcggggtt | cggcttctgg | cgtgtgaccg | 1800 |
| gcggctctag | agcctctgct | aaccatgttc | atgccttctt | ctttttccta | cagctcctgg | 1860 |
| gcaacgtgct | ggttattgtg | ctgtctcatc | attttggcaa | agaattgatt | aattcgagcg | 1920 |
| aacgcgtgcc | accatgcctc | ctcctagaac | tggaagggg | ctgctgtggc | tgggctggt | 1980 |
| cctgtcatca | gtgtgtgtcg | ctctgggctc | cgagactcag | gcaaactcca | ccacagacgc | 2040 |
| cctgaatgtg | ctgctgatca | ttgtcgacga | tctgcgacct | tccctggggt | gctacgcgga | 2100 |
| caagctggta | aggtctccaa | acatcgatca | gctggcttca | cacagcctgc | tgttccaaa | 2160 |
| tgcctttgct | cagcaggcag | tgtgtgcacc | atcacgggtc | agcttcctga | ccggaaggag | 2220 |

```
acctgacact accaggctgt acgattttaa ctcatattgg agagtgcatg ccgggaattt    2280
cagcaccatc ccacagtact ttaaggagaa cggctatgtg acaatgtccg tgggaaaagt    2340
cttccacccc ggcattagct ccaatcatac agacgattct ccatactcct ggtctttccc    2400
cccttatcac ccctctagtg agaagtacga aacacaaaaa acttgcaggg gaccagacgg    2460
ggagctgcat gcaaatctgc tgtgtcccgt ggacgtcctg gatgtgcccg aaggcacact    2520
gcctgataag cagagcactg agcaggccat tcagctgctg gaaaagatga aaacaagtgc    2580
ttcacccttc tttctggcag tgggatatca caaaccacat atccccttca gatatcccaa    2640
ggagtttcag aaactgtacc ctctggaaaa cattactctg ctcccgacc ctgaggtgcc     2700
tgatggactg ccacccgtcg catataaccc atggatggac atccggcagc gcgaggatgt    2760
gcaggccctg aatatcagtg tcccttacgg gccaattccc gtggacttcc agagaaagat    2820
tcggcagtct tactttgcca gcgtctccta tctggatact caagtgggac gactgctgag    2880
cgctctggac gatctgcagc tggccaacag caccatcatt gctttcacat ccgaccacgg    2940
atgggctctg ggagagcatg gagaatgggc aaagtatagc aatttcgatg tggccactca    3000
cgtcccactg atcttttacg tgcccggccg aaccgcatcc ctgccagagg ctggagaaaa    3060
actgttccct tacctggacc catttgattc tgctagtcag ctgatggagc ctggccgaca    3120
gtctatggac ctggtggaac tggtcagtct gttccctaca ctggctggac tggcaggact    3180
gcaggtgcct ccaagatgcc ctgtgccatc ttttcacgtc gagctgtgtc gggaaggcaa    3240
gaacctgctg aaacatttca ggttcaggga cctggaggaa gatccttatc tgccaggaaa    3300
tcccagggag ctgatcgcct acagtcagta tccccgccct tcagacattc tcagtggaa    3360
ctccgacaag ccatctctga aggatatcaa aattatggga tacagcatcc gcactattga    3420
ttaccgatat accgtgtggg tcgggttcaa ccccgacgag ttcctggcaa attttagtga    3480
tatccacgcc ggcgaactgt attttgtgga ctcagatcct ctgcaggacc ataacatgta    3540
caatgacagc cagggcggag atctgttcca gctgctgatg ccatgagaat tcgagctcgg    3600
tacccgggaa tcaattcact cctcaggtgc aggctgccta tcagaaggtg gtggctggtg    3660
tggccaatgc cctggctcac aaataccact gagatctttt tccctctgcc aaaaattatg    3720
gggacatcat gaagcccctt gagcatctga cttctggcta ataaaggaaa tttattttca    3780
ttgcaatagt gtgttggaat ttttgtgtc tctcactcgg aaggacatat gggagggcaa     3840
atcatttaaa acatcagaat gagtatttgg tttagagttt ggcaacatat gcccatatgc    3900
tggctgccat gaacaaaggt tggctataaa gaggtcatca gtatatgaaa cagcccctg     3960
ctgtccattc cttattccat agaaaagcct tgacttgagg ttagattttt tttatatttt    4020
gttttgtgtt attttttct ttaacatccc taaaattttc cttacatgtt ttactagcca     4080
gattttccct cctctcctga ctactcccag tcatagctgt ccctcttctc ttatggagat    4140
ccctcgacct gcagcccaag ctgtagataa gtagcatggc gggttaatca ttaactacaa    4200
ggaaccccta gtgatggagt tggccactcc ctctctgcgc gctcgctcgc tcactgaggc    4260
cgcccgggct tgcccgggc ggcctcagtg agcgagcgag cgcgcag                   4307
```

```
<210> SEQ ID NO 11
<211> LENGTH: 1665
<212> TYPE: DNA
<213> ORGANISM: Artificial Sequence
<220> FEATURE:
<223> OTHER INFORMATION: omIDS
```

<400> SEQUENCE: 11

```
atgagcccac ctcccccacc cccaatctgg cggcagctga gcttcagcct gctgctgggc      60
agcttctgta tcgccctgga aagcgccaag cttgcccagg caacagcgc caccgacgcc     120
ctgaacatcc tgctgatcat cgtggacgac ctgaggccca gctgggatg ctacggcgac     180
aagctggtcc gcagccccaa catcgaccag ctggcttctc acagcgtgct gttccagaac    240
gcattcgcac agcaggccgt gtgcgccccc agcagagtgt ctttcctgac cggcagaagg    300
cccgacacca ccagactgta cgacttcaac agctactggc gggtgcacag cggcaacttc    360
agcaccatcc cccagtactt caaagaaaac ggctacgtga ccatgagcgt gggcaaggtg    420
ttccaccccg gcatcagcag caaccacagc gacgactacc cctacagctg gtccttccca    480
ccctaccacc ccagcagcga gaagtacgag aacaccaaga cctgcaaggg ccaggacggc    540
aagctgcacg ccaacctgct gtgccctgtg gacgtggcag acgtgccaga gggaaccctg    600
cctgacaagc agagcaccga ggaagccatc agactgctgg aaaagatgaa gaccagcgcc    660
agccccttct tcctggccgt gggctaccac aagccccaca tccctttcag ataccccaaa    720
gagttccaga gctgtaccc ctggaaaac atcaccctgg ccccgaccc ccacgtgcca      780
gattctctgc ccccgtggc ctacaacccc tggatggata ccgcgagcg cgaggacgtg     840
caggctctga acatcagcgt gcctacggc cctatccccg aggacttcca gagaaagatc     900
agacagagct acttcgccag cgtgtcctac ctggacaccc aagtgggaca cgtgctgagc    960
gccctggacg atctgagact ggcccacaac accatcattg ccttcaccag cgaccacggc   1020
tgggctctgg agagcacgg cgagtgggcc aagtacagca acttcgacgt ggccaccaga   1080
gtgcccctga tgctgtacgt gcccggcaga accgccccctc tgcctgccgc tggacagaag   1140
ctgttcccctt accgggaccc cttcgacccc gccagcgatt ggatgacgc cggcagacac   1200
accgaggacc tggtggaact ggtgtccctg ttccccaccc tggccggact ggctggactg   1260
cctgtgcccc ccagatgccc catccctagc ttccacgtcg aactgtgcag agagggccag   1320
aacctgcaga acatctgca gctgcacgac ctggaagagg aacccgaccct gttcggcaac   1380
cccagagagc tgatcgccta cagccagtac cccagaccg ccgacttccc ccagtggaac   1440
agcgacaagc ccagcctgaa cgacatcaaa gtgatgggct acagcatcag gaccgtggac   1500
tacagataca ccgtgtgggt cggattcgac cccagcgagt tcctggccaa cttcagcgac   1560
atccacgccg gcgagctgta cttcgtggac agcgaccccc tgcaggacca caacgtgtac   1620
aacgacagcc agcacggcgg cctgctgcac agcctgaggc cttga                    1665
```

<210> SEQ ID NO 12
<211> LENGTH: 7914
<212> TYPE: DNA
<213> ORGANISM: Artificial Sequence
<220> FEATURE:
<223> OTHER INFORMATION: pAAV-CAG-omIDS

<400> SEQUENCE: 12

```
cgcgtgctag cgccaccatg agcccacctc cccacccc aatctggcgg cagctgagct      60
tcagcctgct gctgggcagc ttctgtatcg ccctggaaag cgccaagctt gcccagggca    120
acagcgccac cgacgccctg aacatcctgc tgatcatcgt ggacgacctg aggcccagcc    180
tgggatgcta cggcgacaag ctggtccgca gccccaacat cgaccagctg gcttctcaca    240
gcgtgctgtt ccagaacgca ttcgcacagc aggccgtgtg cgcccccagc agagtgtctt    300
cctgaccgg cagaaggccc gacaccacca gactgtacga cttcaacagc tactggcggg    360
```

```
tgcacagcgg caacttcagc accatccccc agtacttcaa agaaaacggc tacgtgacca    420
tgagcgtggg caaggtgttc cacccggca tcagcagcaa ccacagcgac gactacccct    480
acagctggtc cttcccaccc taccacccca gcagcgagaa gtacgagaac accaagacct    540
gcaagggcca ggacggcaag ctgcacgcca acctgctgtg ccctgtggac gtggcagacg    600
tgccagaggg aaccctgcct gacaagcaga gcaccgagga agccatcaga ctgctggaaa    660
agatgaagac cagcgccagc cccttcttcc tggccgtggg ctaccacaag ccccacatcc    720
ctttcagata ccccaaagag ttccagaagc tgtaccccct ggaaaacatc accctggccc    780
ccgaccccca cgtgccagat tctctgcccc ccgtggccta caaccctggg atggatatcc    840
gcgagcgcga ggacgtgcag gctctgaaca tcagcgtgcc ctacggccct atccccgagg    900
acttccagag aaagatcaga cagagctact tcgccagcgt gtcctacctg gacacccaag    960
tgggacacgt gctgagcgcc ctggacgatc tgagactggc ccacaacacc atcattgcct   1020
tcaccagcga ccacgctgg gctctgggag agcacggcga gtgggccaag tacagcaact   1080
tcgacgtggc caccagagtg cccctgatgc tgtacgtgcc cggcagaacc gcccctctgc   1140
ctgccgctgg acagaagctg ttcccttacc gggacccctt cgaccccgcc agcgattgga   1200
tggacgccgg cagacacacc gaggacctgg tggaactggt gtccctgttc ccacccctgg   1260
ccggactggc tggactgcct gtgcccccca gatgccccat ccctagcttc cacgtcgaac   1320
tgtgcagaga gggccagaac ctgcagaaac atctgcagct gcacgacctg gaagaggaac   1380
ccgacctgtt cggcaacccc agagagctga tcgcctacag ccagtacccc agacccgccg   1440 acttcccca gtgaacagc gacaagccca gcctgaacga catcaaagtg atgggctaca   1500
gcatcaggac cgtggactac agatacaccg tgtgggtcgg attcgacccc agcgagttcc   1560
tggccaactt cagcgacatc cacgccgcg agctgtactt cgtggacagc gaccccctgc   1620
aggaccacaa cgtgtacaac gacagccagc acggcggcct gctgcacagc ctgaggcctt   1680
gagcggccgc gaattcgagc tcggtacccg ggaatcaatt cactcctcag gtgcaggctg   1740
cctatcagaa ggtggtggct ggtgtggcca atgccctggc tcacaaatac cactgagatc   1800 tttttcccctc tgccaaaaat tatggggaca tcatgaagcc ccttgagcat ctgacttctg   1860
gctaataaag gaaatttatt ttcattgcaa tagtgtgttg aatttttttg tgtctctcac   1920
tcggaaggac atatgggagg gcaaatcatt taaaacatca gaatgagtat ttggtttaga   1980
gtttggcaac atatgcccat atgctggctg ccatgaacaa aggttggcta taaagaggtc   2040
atcagtatat gaaacagccc cctgctgtcc attccttatt ccatagaaaa gccttgactt   2100
gaggttagat ttttttata ttttgttttg tgttatttt tctttaaca tccctaaaat   2160 tttccttaca tgttttacta gccagatttt tcctcctctc ctgactactc ccagtcatag   2220
ctgtccctct tctcttatgg agatccctcg acctgcagcc caagctgtag ataagtagca   2280
tggcgggtta atcattaact acaaggaacc cctagtgatg gagttggcca ctccctctct   2340
gcgcgctcgc tcgctcactg aggccgcccg ggctttgccc gggcggcctc agtgagcgag   2400
cgagcgcgca gctgcattaa tgaatcggcc aacgcgcggg gagaggcggt ttgcgtattg   2460
ggcgctcttc cgcttcctcg ctcactgact cgctgcgctc ggtcgttcgg ctgcggcgag   2520
cggtatcagc tcactcaaag gcggtaatac ggttatccac agaatcaggg gataacgcag   2580
gaaagaacat gtgagcaaaa ggccagcaaa aggccaggaa ccgtaaaaag gccgcgttgc   2640
tggcgttttt ccataggctc cgcccccctg acgagcatca caaaaatcga cgctcaagtc   2700
agaggtggcg aaacccgaca ggactataaa gataccaggc gtttccccct ggaagctccc   2760
```

```
tcgtgcgctc tcctgttccg acccctgccgc ttaccggata cctgtccgcc tttctccctt    2820
cgggaagcgt ggcgctttct catagctcac gctgtaggta tctcagttcg gtgtaggtcg    2880
ttcgctccaa gctgggctgt gtgcacgaac cccccgttca gcccgaccgc tgcgccttat    2940
ccggtaacta tcgtcttgag tccaacccgg taagacacga cttatcgcca ctggcagcag    3000
ccactggtaa caggattagc agagcgaggt atgtaggcgg tgctacagag ttcttgaagt    3060
ggtggcctaa ctacggctac actagaagaa cagtatttgg tatctgcgct ctgctgaagc    3120
cagttacctt cggaaaaaga gttggtagct cttgatccgg caaacaaacc accgctggta    3180
gcggtggttt ttttgtttgc aagcagcaga ttacgcgcag aaaaaaagga tctcaagaag    3240
atcctttgat cttttctacg gggtctgacg ctcagtggaa cgaaaactca cgttaaggga    3300
ttttggtcat gagattatca aaaggatct tcacctagat ccttttaaat taaaaatgaa    3360
gttttaaatc aatctaaagt atatatgagt aaacttggtc tgacagttac caatgcttaa    3420
tcagtgaggc acctatctca gcgatctgtc tatttcgttc atccatagtt gcctgactcc    3480
ccgtcgtgta gataactacg atacgggagg gcttaccatc tggccccagt gctgcaatga    3540
taccgcgaga cccacgctca ccggctccag atttatcagc aataaaccag ccagccggaa    3600
gggccgagcg cagaagtggt cctgcaactt tatccgcctc catccagtct attaattgtt    3660
gccgggaagc tagagtaagt agttcgccag ttaatagttt gcgcaacgtt gttgccattg    3720
ctacaggcat cgtggtgtca cgctcgtcgt ttggtatggc ttcattcagc tccggttccc    3780
aacgatcaag gcgagttaca tgatccccca tgttgtgcaa aaaagcggtt agctccttcg    3840
gtcctccgat cgttgtcaga agtaagttgg ccgcagtgtt atcactcatg gttatggcag    3900
cactgcataa ttctcttact gtcatgccat ccgtaagatg cttttctgtg actggtgagt    3960
actcaaccaa gtcattctga gaatagtgta tgcggcgacc gagttgctct tgcccggcgt    4020
caatacggga taataccgcg ccacatagca gaactttaaa agtgctcatc attggaaaac    4080
gttcttcggg gcgaaaactc tcaaggatct taccgctgtt gagatccagt tcgatgtaac    4140
ccactcgtgc acccaactga tcttcagcat cttttacttt caccagcgtt tctgggtgag    4200
caaaaacagg aaggcaaaat gccgcaaaaa agggaataag ggcgacacgg aaatgttgaa    4260
tactcatact cttcctttt caatattatt gaagcattta tcagggttat tgtctcatga    4320
gcggatacat atttgaatgt atttagaaaa ataaacaaat aggggttccg cgcacatttc    4380
cccgaaaagt gccacctgac gtctaagaaa ccattattat catgacatta acctataaaa    4440
ataggcgtat cacgaggccc tttcgtctcg cgcgtttcgg tgatgacggt gaaaacctct    4500
gacacatgca gctcccggag acggtcacag cttgtctgta agcggatgcc gggagcagac    4560
aagcccgtca gggcgcgtca gcgggtgttg gcgggtgtcg gggctggctt aactatgcgg    4620
catcagagca gattgtactg agagtgcacc atatgcggtg tgaaataccg cacagatgcg    4680
taaggagaaa ataccgcatc aggcgattcc aacatccaat aaatcataca ggcaaggcaa    4740
agaattagca aaattaagca ataaagcctc agagcataaa gctaaatcgg ttgtaccaaa    4800
aacattatga ccctgtaata cttttgcggg agaagccttt atttcaacgc aaggataaaa    4860
atttttagaa ccctcatata ttttaaatgc aatgcctgag taatgtgtag gtaaagattc    4920
aaacgggtga gaaaggccgg agacagtcaa atcaccatca atatgatatt caaccgttct    4980
agctgataaa ttcatgccgg agagggtagc tattttgag aggtctctac aaaggctatc    5040
aggtcattgc ctgagagtct ggagcaaaca agagaatcga tgaacggtaa tcgtaaaact    5100
agcatgtcaa tcatatgtac cccggttgat aatcagaaaa gccccaaaaa caggaagatt    5160
```

```
gtataagcaa atatttaaat tgtaagcgtt aatattttgt taaaattcgc gttaaatttt      5220
tgttaaatca gctcattttt taaccaatag gccgaaatcg gcaaaatccc ttataaatca      5280
aaagaataga ccgagatagg gttgagtgtt gttccagttt ggaacaagag tccactatta      5340
aagaacgtgg actccaacgt caaagggcga aaaccgtct atcagggcga tggcccacta       5400
cgtgaaccat caccctaatc aagttttttg gggtcgaggt gccgtaaagc actaaatcgg      5460
aaccctaaag ggagccccg atttagagct tgacggggaa agccggcgaa cgtggcgaga       5520
aaggaaggga agaaagcgaa aggagcgggc gctagggcgc tggcaagtgt agcggtcacg      5580
ctgcgcgtaa ccaccacacc cgccgcgctt aatgcgccgc tacagggcgc gtactatggt      5640
tgctttgacg agcacgtata acgtgctttc ctcgttagaa tcagagcggg agctaaacag      5700
gaggccgatt aaagggattt tagacaggaa cggtacgcca gaatcctgag aagtgttttt      5760
ataatcagtg aggccaccga gtaaaagagt ctgtccatca cgcaaattaa ccgttgtcgc      5820
aatacttctt tgattagtaa taacatcact tgcctgagta gaagaactca aactatcggc      5880
cttgctggta atatccagaa caatattacc gccagccatt gcaacggaat cgccattcgc      5940
cattcaggct gcgcaactgt tgggaagggc gatcggtgcg ggcctcttcg ctattacgcc      6000
agctgcgcgc tcgctcgctc actgaggccg cccgggcaaa gcccgggcgt cgggcgacct      6060
ttggtcgccc ggcctcagtg agcgagcgag cgcgcagaga gggagtggcc aactccatca      6120
ctaggggttc cttgtagtta atgattaacc cgccatgcta cttatctact cgacattgat      6180
tattgactag ttattaatag taatcaatta cggggtcatt agttcatagc ccatatatgg      6240
agttccgcgt tacataactt acggtaaatg gcccgcctgg ctgaccgccc aacgacccc       6300 gcccattgac gtcaataatg acgtatgttc ccatagtaac gccaataggg actttccatt      6360
gacgtcaatg ggtggagtat ttacggtaaa ctgcccactt ggcagtacat caagtgtatc      6420
atatgccaag tacgccccct attgacgtca atgacggtaa atggcccgcc tggcattatg      6480
cccagtacat gaccttatgg gactttccta cttggcagta catctacgta ttagtcatcg      6540
ctattaccat ggtcgaggtg agccccacgt tctgcttcac tctccccatc tccccccct       6600 ccccaccccc aattttgtat ttatttattt tttaattatt ttgtgcagcg atggggcgg       6660 gggggggggg ggggcgcgcg ccaggcgggg cgggcgggg cgaggggcgg ggcggggcga       6720
ggcggagagg tgcggcggca gccaatcaga gcggcgcgct ccgaaagttt cctttatgg       6780 cgaggcggcg gcggcggcgg ccctataaaa agcgaagcgc gcggcgggcg ggagtcgctg      6840
cgttgccttc gccccgtgcc ccgctccgcc gccgcctcgc gccgcccgcc ccggctctga      6900
ctgaccgcgt tactcccaca ggtgagcggg cgggacggcc cttctcctcc gggctgtaat      6960
tagcgcttgg tttaatgacg gcttgtttct tttctgtggc tgcgtgaaag ccttgagggg      7020
ctccgggagg gccctttgtg cggggggagc ggctcggggg gtgcgtgcgt gtgtgtgtgc      7080
gtggggagcg ccgcgtgcgg ctccgcgctg cccggcggct gtgagcgctg cgggcgcggc      7140
gcggggcttt gtgcgctccg cagtgtgcgc gaggggagcg cggccggggg cggtgccccg      7200
cggtgcgggg gggctgcga ggggaacaaa ggctgcgtgc ggggtgtgtg cgtgggggg       7260 tgagcagggt gtgtgggcgc gtcggtcggg ctgcaacccc ccctgcaccc ccctccccga      7320
gttgctgagc acggcccggc ttcgggtgcg gggctccgta cggggcgtgg cgcggggctc      7380
gccgtgccgg gcggggggtg gcggcaggtg ggggtgccgg gcggggcggg gccgcctcgg      7440
gccggggagg gctcggggga ggggcgcggc ggccccgga gcgccggcgg ctgtcgaggc       7500
gcggcgagcc gcagccattg ccttttatgg taatcgtgcg agagggcgca gggacttcct      7560
```

| | | |
|---|---|---|
| ttgtcccaaa tctgtgcgga gccgaaatct gggaggcgcc gccgcacccc ctctagcggg | 7620 | |
| cgcggggcga gcggtgcgg cgccggcagg aaggaaatgg gcggggaggg ccttcgtgcg | 7680 | |
| tcgccgcgcc gccgtcccct tctccctctc cagcctcggg gctgtccgcg ggggacggc | 7740 | |
| tgccttcggg ggggacgggg cagggcgggg ttcggcttct ggcgtgtgac cggcggctct | 7800 | |
| agagcctctg ctaaccatgt tcatgccttc ttctttttcc tacagctcct gggcaacgtg | 7860 | |
| ctggttattg tgctgtctca tcattttggc aaagaattga ttaattcgag cgaa | 7914 | |

<210> SEQ ID NO 13
<211> LENGTH: 4333
<212> TYPE: DNA
<213> ORGANISM: Artificial Sequence
<220> FEATURE:
<223> OTHER INFORMATION: AAV9-CAG-omIDS

<400> SEQUENCE: 13

| | | |
|---|---|---|
| attacgccag ctgcgcgctc gctcgctcac tgaggccgcc cgggcaaagc ccgggcgtcg | 60 | |
| ggcgaccttt ggtcgcccgg cctcagtgag cgagcgagcg cgcagagagg gagtggccaa | 120 | |
| ctccatcact aggggttcct tgtagttaat gattaacccg ccatgctact tatctactcg | 180 | |
| acattgatta ttgactagtt attaatagta atcaattacg gggtcattag ttcatagccc | 240 | |
| atatatggag ttccgcgtta cataacttac ggtaaatggc ccgcctggct gaccgcccaa | 300 | |
| cgaccccgc ccattgacgt caataatgac gtatgttccc atagtaacgc caatagggac | 360 | |
| tttccattga cgtcaatggg tggagtattt acggtaaact gcccacttgg cagtacatca | 420 | |
| agtgtatcat atgccaagta cgccccctat tgacgtcaat gacggtaaat ggcccgcctg | 480 | |
| gcattatgcc cagtacatga ccttatggga ctttcctact tggcagtaca tctacgtatt | 540 | |
| agtcatcgct attaccatgg tcgaggtgag ccccacgttc tgcttcactc tccccatctc | 600 | |
| ccccccctcc ccaccccaa ttttgtattt atttattttt taattatttt gtgcagcgat | 660 | |
| gggggcgggg ggggggggg ggcgcgcgcc aggcggggcg gggcggggcg aggggcgggg | 720 | |
| cggggcgagg cggagaggtg cggcggcagc caatcagagc ggcgcgctcc gaaagtttcc | 780 | |
| ttttatggcg aggcggcggc ggcggcggcc ctataaaaag cgaagcgcgc ggcgggcggg | 840 | |
| agtcgctgcg ttgccttcgc cccgtgcccc gctccgccgc cgcctcgcgc cgcccgcccc | 900 | |
| ggctctgact gaccgcgtta ctcccacagg tgagcgggcg ggacggccct tctcctccgg | 960 | |
| gctgtaatta gcgcttggtt taatgacggc ttgtttcttt tctgtggctg cgtgaaagcc | 1020 | |
| ttgaggggct ccgggagggc cctttgtgcg ggggagcgg ctcggggggt gcgtgcgtgt | 1080 | |
| gtgtgtgcgt ggggagcgcc gcgtgcggct ccgcgctgcc cggcggctgt gagcgctgcg | 1140 | |
| ggcgcggcgc ggggctttgt gcgctccgca gtgtgcgcga ggggagcgcg gccggggcg | 1200 | |
| gtgccccgcg gtgcgggggg ggctgcgagg ggaacaaagg ctgcgtgcgg ggtgtgtgcg | 1260 | |
| tgggggggtg agcaggggt gtgggcgcgt cggtcgggct gcaacccccc ctgcaccccc | 1320 | |
| ctccccgagt tgctgagcac ggcccggctt cgggtgcggg gctccgtacg gggcgtggcg | 1380 | |
| cggggctcgc cgtgccgggc gggggtggc ggcaggtggg ggtgccgggc ggggcgggc | 1440 | |
| cgcctcgggc cggggagggc tcggggagg ggcgcggcgg ccccggagc gccggcggct | 1500 | |
| gtcgaggcgc ggcgagccgc agccattgcc ttttatggta atcgtgcgag agggcgcagg | 1560 | |
| gacttccttt gtcccaaatc tgtgcggagc cgaaatctgg gaggcgccgc cgcacccct | 1620 | |
| ctagcgggcg cggggcgaag cggtgcgcg ccggcaggaa ggaaatgggc ggggagggcc | 1680 | |
| ttcgtgcgtc gccgcgccgc cgtccccttc tccctctcca gcctcggggc tgtccgcggg | 1740 | |

```
gggacggctg ccttcggggg ggacggggca gggcggggtt cggcttctgg cgtgtgaccg    1800
gcggctctag agcctctgct aaccatgttc atgccttctt cttttttccta cagctcctgg    1860 gcaacgtgct ggttattgtg ctgtctcatc attttggcaa agaattgatt aattcgagcg    1920
aacgcgtgct agcgccacca tgagcccacc tcccccaccc ccaatctggc ggcagctgag    1980
cttcagcctg ctgctgggca gcttctgtat cgccctggaa agcgccaagc ttgcccaggg    2040
caacagcgcc accgacgccc tgaacatcct gctgatcatc gtggacgacc tgaggcccag    2100
cctgggatgc tacggcgaca agctggtccg cagccccaac atcgaccagc tggcttctca    2160
cagcgtgctg ttccagaacg cattcgcaca gcaggccgtg tgcgccccca gcagagtgtc    2220
tttcctgacc ggcagaaggc ccgacaccac cagactgtac gacttcaaca gctactggcg    2280
ggtgcacagc ggcaacttca gcaccatccc ccagtacttc aaagaaaacg gctacgtgac    2340
catgagcgtg ggcaaggtgt ccacccccgg catcagcagc aaccacagcg acgactaccc    2400
ctacagctgg tccttcccac cctaccaccc cagcagcgag aagtacgaga acaccaagac    2460
ctgcaagggc caggacggca agctgcacgc caacctgctg tgccctgtgg acgtggcaga    2520
cgtgccagag ggaaccctgc ctgacaagca gagcaccgag gaagccatca gactgctgga    2580
aaagatgaag accagcgcca gcccttcttc cctggccgtg ggctaccaca gccccacat    2640 cccttcaga tacccaaag agttccagaa gctgtacccc ctggaaaaca tcaccctggc    2700
ccccgacccc cacgtgccag attctctgcc ccccgtggcc tacaaccct ggatggatat    2760 ccgcgagcgc gaggacgtgc aggctctgaa catcagcgtg ccctacggcc tatccccga    2820 ggacttccag agaaagatca gacagagcta cttcgccagc gtgtcctacc tggacaccca    2880
agtgggacac gtgctgagcg ccctggacga tctgagactg gcccacaaca ccatcattgc    2940
cttcaccagc gaccacggct gggctctggg agagcacggc gagtgggcca agtacagcaa    3000
cttcgacgtg gccaccagag tgcccctgat gctgtacgtg cccggcagaa ccgcccctct    3060
gcctgccgct ggacagaagc tgttcccctta ccgggacccc ttcgaccccg ccagcgattg    3120
gatggacgcc ggcagacaca ccgaggacct ggtggaactg gtgtccctgt tccccaccct    3180
ggccggactg gctggactgc ctgtgccccc cagatgcccc atccctagct ccacgtcga    3240 actgtgcaga gagggccaga acctgcagaa acatctgcag ctgcacgacc tggaagagga    3300
acccgacctg ttcggcaacc ccagagagct gatcgcctac agccagtacc ccagacccgc    3360
cgacttcccc cagtggaaca cgacaagcc cagcctgaac gacatcaaag tgatgggcta    3420
cagcatcagg accgtggact acagatacac cgtgtgggtc ggattcgacc ccagcgagtt    3480
cctggccaac ttcagcgaca tccacgccgg cgagctgtac ttcgtggaca cgacccccct    3540
gcaggaccac aacgtgtaca cgacagcca gcacggcggc ctgctgcaca gcctgaggcc    3600
ttgagcggcc gcgaattcga gctcggtacc cgggaatcaa ttcactcctc aggtgcaggc    3660
tgcctatcag aaggtggtgg ctggtgtggc caatgccctg gctcacaaat accactgaga    3720
tctttttccc tctgccaaaa attatgggga catcatgaag ccccttgagc atctgacttc    3780
tggctaataa aggaaatta ttttcattgc aatagtgtgt tggaattttt tgtgtctctc    3840
actcggaagg acatatggga gggcaaatca tttaaaacat cagaatgagt atttggttta    3900
gagtttggca acatatgccc atatgctggc tgccatgaac aaaggttggc tataagagg    3960 tcatcagtat atgaaacagc cccctgctgt ccattcctta ttccatagaa aagccttgac    4020
ttgaggttag attttttttta tatttttgttt tgtgttattt ttttctttaa catccctaaa    4080
```

```
attttccetta catgttttac tagccagatt tttcctcctc tcctgactac tcccagtcat    4140
agctgtccct cttctcttat ggagatccct cgacctgcag cccaagctgt agataagtag    4200
catggcgggt taatcattaa ctacaaggaa ccectagtga tggagttggc cactccctct    4260
ctgcgcgctc gctcgctcac tgaggccgcc cgggctttgc ccgggcggcc tcagtgagcg    4320
agcgagcgcg cag                                                       4333
```

```
<210> SEQ ID NO 14
<211> LENGTH: 646
<212> TYPE: DNA
<213> ORGANISM: Artificial Sequence
<220> FEATURE:
<223> OTHER INFORMATION: CAG promoter

<400> SEQUENCE: 14
actagttatt aatagtaatc aattacgggg tcattagttc atagcccata tatggagttc      60
cgcgttacat aacttacggt aaatggcccg cctggctgac cgcccaacga ccccegccca    120 ttgacgtcaa taatgacgta tgttcccata gtaacgccaa tagggacttt ccattgacgt    180
caatgggtgg agtatttacg gtaaactgcc cacttggcag tacatcaagt gtatcatatg    240
ccaagtacgc cccctattga cgtcaatgac ggtaaatggc ccgcctggca ttatgcccag    300
tacatgacct tatgggactt tcctacttgg cagtacatct acgtattagt catcgctatt    360
accatggtcg aggtgagccc cacgttctgc ttcactctcc ccatctcccc cccctcccca    420
cccccaattt tgtatttatt tattttttaa ttattttgtg cagcgatggg ggcggggggg    480 ggggggggc gcgcgccagg cggggcgggg cggggcgagg gccggggcgg ggcgaggcgg    540
agaggtgcgg cggcagccaa tcagagcggc gcgctccgaa agtttccttt tatggcgagg    600
cggcggcggc ggcggcccta taaaaagcga agcgcgcggc gggcgg                   646
```

```
<210> SEQ ID NO 15
<211> LENGTH: 20
<212> TYPE: DNA
<213> ORGANISM: Artificial Sequence
<220> FEATURE:
<223> OTHER INFORMATION: Forward Primer

<400> SEQUENCE: 15
ttttgtgtac tccaaccccg                                                 20
```

```
<210> SEQ ID NO 16
<211> LENGTH: 20
<212> TYPE: DNA
<213> ORGANISM: Artificial Sequence
<220> FEATURE:
<223> OTHER INFORMATION: Reverse Primer

<400> SEQUENCE: 16
tgtctgcata acagcccagg                                                 20
```

```
<210> SEQ ID NO 17
<211> LENGTH: 20
<212> TYPE: DNA
<213> ORGANISM: Artificial Sequence
<220> FEATURE:
<223> OTHER INFORMATION: Reverse Primer Mutation

<400> SEQUENCE: 17
gccctcacat tgccaaagga                                                 20
```

```
<210> SEQ ID NO 18
<211> LENGTH: 25
<212> TYPE: DNA
<213> ORGANISM: Artificial Sequence
<220> FEATURE:
<223> OTHER INFORMATION: Forward primer for the HBB2 sequence

<400> SEQUENCE: 18
cttgagcatc tgacttctgg ctaat                                              25

<210> SEQ ID NO 19
<211> LENGTH: 21
<212> TYPE: DNA
<213> ORGANISM: Artificial Sequence
<220> FEATURE:
<223> OTHER INFORMATION: Reverse primer for the HBB2 sequence

<400> SEQUENCE: 19
gatttgccct cccatatgtc c                                                  21

<210> SEQ ID NO 20
<211> LENGTH: 30
<212> TYPE: DNA
<213> ORGANISM: Artificial Sequence
<220> FEATURE:
<223> OTHER INFORMATION: Probe for the HBB2 sequence

<400> SEQUENCE: 20
ccgagtgaga gacacaaaaa attccaacac                                         30
```

ADENOASSOCIATED VIRUS VECTORS FOR THE TREATMENT OF MUCOPOLYSACCHARIDOSES

FIELD OF THE INVENTION

The present invention relates to vectors useful for the expression of proteins of interest and their utilization in gene therapy. The present invention also relates to vectors and nucleic acid sequences helpful for the treatment of mucopolysaccharidoses (MPS), and in particular, for the treatment of mucopolysaccharidoses type II or Hunter syndrome.

BACKGROUND OF THE INVENTION

The lysosome is an organelle found in the cytoplasm of animal cells that contains more than 50 hydrolases that break down biomolecules during the recycling of worn-out cellular components or after the engulfment of viruses and bacteria. This organelle contains several types of hydrolytic enzymes, including proteases, nucleases, glycosidases, lipases, phospholipases, phosphatases and sulfatases. All enzymes are acid hydrolases.

Lysosomal storage diseases (LSDs) are caused by genetic defects that affect one or more lysosomal enzymes. These genetic diseases result generally from a deficiency in a particular enzyme activity present in the lysosome. To a lesser extent, these diseases may be due to deficiencies in proteins involved in lysosomal biogenesis.

LSDs are individually rare, although as a group these disorders are relatively common in the general population. The combined prevalence of LSDs is approximately 1 per 5,000 live births. See Meikle P, et al., JAMA 1999; 281: 249-254. However, some groups within the general population are particularly afflicted by a high occurrence of LSDs. For instance, the prevalence of Gaucher and Tay-Sachs diseases in descendants from Jewish Central and Eastern European (Ashkenazi) individuals is 1 per 600 and 1 per 3,900 births, respectively.

Type II mucopolysaccharidoses (MPSII), known also as Hunter syndrome and first described by Dr. Charles Hunter, is a chronic, progressive and multisystemic LSDs caused by deficiency or absence of activity of the iduronate-2-sulfatase (IDS) enzyme, encoded by the IDS gene and involved in the lysosomal stepwise degradation of the glycosaminoglycans (GAG) heparan sulfate (HS) and dermatan sulfate (DS), leading to their pathological accumulation. See Hunter, Proc R Soc Med. 1917; 10 (Sect Study Dis Child): 104-16. Due to the X-linked recessive inheritance, almost all Hunter patients are males, although some women with Hunter syndrome have been reported in the literature. See Mossman et al., Arch Dis Child. 1983; 58.911-915, Gullén-Navarro et al., Orphanet J Rare Dis. 2013; 25(8):92, Valstar et al., J. Inherit. Metab. Dis. 2008; 31(2):240-52.

MPSII is characterized clinically as a childhood-onset, progressive neuropathy of the Central Nervous System (CNS). Hunter children are usually normal at birth and develop symptoms before the age of 2 years. See Schwartz et al., Acta Paediatr Suppl. 2007; 96:63-70. The clinical course generally begins with slow-progressive cognitive impairment followed by behavioural problems and progressive intellectual decline. Loss of locomotion occurs later. In addition to the neurological symptoms, MPSII patients suffer from non-neurological alterations, including recurrent ear, nose, throat and chest infections, frequent diarrhoea and constipation, cardiac failure, coarse facial features, short stature, progressive joint stiffness and degeneration, skeletal abnormalities which affect mobility, as well as hepato and splenomegaly. See Neufeld and Muenzer, "The Mucopolysaccharidoses" in Scriver C, et al., Eds., "The metabolic and molecular basis of inherited disease", McGraw-Hill Publishing Co., New York, N.Y., US, 2001, pp. 3421-3452. The spectrum of clinical manifestations of the disease varies considerably depending on the residual levels of IDS activity that the patient has, which in turn is determined by the underlying mutation of the IDS gene, with >300 mutations of the IDS gene described to date. In general, two clinical forms of MPSII have been described. The most severe form, with an onset between 18 months and 4 years of age, is three times more common than the mild form, and, is characterized by coarse facial features, skeletal deformities, hepatosplenomegaly and neurological involvement which leads to mental retardation. See Wraith et al., Eur J Pediatr. 2008; 167(3):267-277. Patients usually die during the second decade of life due to obstructive airway disease and cardiac failure. See Wraith et al., Eur J Pediatr. 2008; 167(3):267-277, Neufeld and Muenzer, supra. A more slowly progressive form of the disease, with later onset, longer survival and minimal neurological dysfunction, known as the attenuated phenotype, has also been reported in a subset of MPSII patients. See Wraith et al., Eur J Pediatr. 2008; 167(3):267-277, Neufeld and Muenzer, supra.

Until recently there were no specific approved therapies for MPSII syndrome and the only treatment available was symptomatic using a wide range of unspecific drugs for the prevention and management of disease complications. In the last few years, two main therapeutic options have become available: Enzyme Replacement Therapy (ERT) and hematopoietic stem cell transplantation (HSCT). The design of both therapeutic strategies relies on the possibility of cross-correction, based on the fact that normal cells secrete significant amounts of mannose-6-phosphate (M6P)-tagged soluble lysosomal enzymes, such as IDS, which can be subsequently taken up from the extracellular compartment by other cells via M6P receptors on the plasma membrane and targeted to the lysosomes. See Enns et al., Neurosurg Focus. 2008; 24(3-4):E12. In addition, there is a threshold of residual enzymatic activity, generally very low, above which the cell is capable of coping with substrate influx and subjects are not affected by the disease, suggesting that restoration of normal activity is not a requisite to modify the clinical course. See Neufeld, Annu Rev Biochem. 1991; 60:257-80.

Since its approval by the Food and Drug Administration (FDA) in 2006 and by the European Medicines Agency (EMA) in 2007, recombinant human iduronate-2-sulfatasa (Idursulfase, ELAPRASE®, Shire Pharmaceuticals) has been indicated for the treatment of patients with MPSII. The treatment is administered weekly at a dose of 0.5 mg/kg by intravenous infusion, with an average infusion time of 1-3 hours. See Giugliani et al., Genet Mol Biol. 2010; 33(4): 589-604. ELAPRASE® was approved after a randomized, double-blind, placebo-controlled study of 96 Hunter patients with no cognitive decline at baseline and with moderately advanced disease. See Muenzer et al., Genet Med. 2006; 8(8):465-73, Muenzer et al., Genet Med. 2011; 13(2):95-101. After one year of treatment, ELAPRASE®-treated patients showed an increase in the distance walked in six minutes (six-minute walk test) compared to patients on placebo. See Muenzer et al., Genet Med. 2011; 13(2):95-101. ERT with ELAPRASE® has also been shown to improve joint range of motion (ROM) and to reduce liver and spleen volumes. See Muenzer et al., Genet Med. 2011; 13(2):95-101. Furthermore, there is evidence of improved pulmonary function when neutralizing antibodies against Idursulfase are not present; development of anti-IDS antibodies was reported in 50% of the long-term treated patients. See Muenzer et al., Genet Med. 2011; 13(2):95-101.

A phase I/II study in 31 MPSII patients compared the efficacy of ELAPRASE® with that of a second product based on the beta isoform of Idursulfase with a proposed commercial name of Hunterase® (NCT01301898). Both proteins were administered intravenously at a dose of 0.5 mg/kg/week for ELAPRASE® and 0.5 and 1.0 mg/kg/week for Hunterase® during 24 weeks. The results from Hunterase® treatment showed reduced urine GAG excretion and improved performance in the 6-minute walking test, but none of the doses was able to mediate therapeutic efficacy in pulmonary function, cardiac function or joint mobility. See Sohn et al., Orphanet J Rare Dis. 2013; 8:42. Hunterase® infusions were generally safe and well-tolerated, although a few adverse events, such as urticaria and skin rash, were reported. See Sohn et al., Orphanet J Rare Dis. 2013; 8:42. A pivotal PIII study has recently been completed (NCT01645189), but results are not yet available.

Due to hypersensitivity to ELAPRASE®, medical support has to be available during product administration. During the trial, the most severe adverse events described were anaphylactic reactions that could appear anytime during ELAPRASE® infusion or up to 24 hours after product administration. See Muenzer et al., Genet Med. 2006; 8(8): 465-73, Muenzer et al., Genet Med. 2011; 13(2):95-101. These anaphylactic reactions, that can compromise the patient's life, include respiratory distress, hypoxia, hypotension, urticaria and/or angioedema of throat or tongue and may require interventions such as resuscitation or emergency tracheotomy, and treatment with inhaled beta-adrenergic agonists, epinephrine or intravenous corticosteroids. See Burton et al., Mol Genet Metab, 2011; 103(2):113-20. Other disadvantages of ERT include: 1) the difficulty of performing 1-3 hour-long intravenous infusions in paediatric patients, many of whom suffer from mental illness the fact that 50% of patients treated with ELAPRASE® in clinical studies became positive for antibodies to Idursulfase of yet unknown clinical significance, but which might limit product efficacy in the long-term, as suggested by tests of pulmonary function. See Muenzer et al., Mol Genet Metab. 2007; 90(3):329-37, Muenzer et al., Genet Med. 2006; 8(8):465-73, Muenzer et al., Genet Med. 2011; 13(2):95-101, and 3) the high cost of the therapy, which includes also the costs of home-care. See Wyatt et al., Health Technol Asses. 2012, 16(39):1-543.

Regardless of the safety concerns or the cost of ELAPRASE® administration, the inability of intravenously administered recombinant IDS to reach the CNS, at least at the currently recommended dose of 0.5 mg/kg per week, likely limits the potential applicability of ERT to the treatment of the severe neurodegeneration observed in Hunter patients. Only a partial rescue of IDS brain activity was achieved by weekly intravenous administration of 1.2 or 10 mg ELAPRASE®/kg to 2 or 7 month-old MPSII mice, respectively. See Polito et al., Hum Mol Genet. 2010; 19(24):4871-85. Furthermore, even at these high doses, IDS activity in circulation returned to pre-treatment levels 72 hours post-administration of the protein. See Polito et al., Hum Mol Genet. 2010; 19(24):4871-85. Indeed, intravenous ERT failed to correct GAG accumulation in the brains of a murine model of MPSII. See Garcia et al., Mol Genet Metab. 2007; 91(2):183-90. Therefore, the indication of ELAPRASE® is limited to the treatment of non-neurological symptoms of the disease.

An alternative to the intravenous delivery of ERT is the provision of the exogenous enzyme directly to the CNS. The administration of 20 μg of recombinant human IDS to the lateral ventricle of 5-month-old MPSII mice every 3 weeks increased IDS activity in cerebrum, cerebellum and somatic organs, such as liver, heart, kidney and testis. See Higuchi et al., Mol Genet Metab. 2012; 107(1-2):122-8. The restoration of IDS activity led to the recovery of short-term memory and locomotor activity and to a reduction in cellular vacuolation and lysosomal distension in cerebellum, liver and testis. However, therapeutic efficacy was partial, GAG content was not completely normalized and some behavioural alterations remained refractory to the treatment. See Higuchi et al., Mol Genet Metab. 2012; 107(1-2):122-8. A recent safety and dose ranging study of administration of Idursulfase to the cerebrospinal fluid (CSF) via an intrathecal drug delivery device to directly treat CNS pathology in Hunter patients has demonstrated reductions of approximately 80-90% in CSF GAG levels after 6 months of treatment. See Muenzer et al., Genet. Med. 2015; doi:10.1038/gim.2015.36 and www.clinicaltrials.gov (NCT00920647). However, the implantation of the permanent intrathecal delivery device that the therapy requires is associated with substantial risks and shortcomings and the therapy itself has a very high economic cost per patient/year.

Another way to reach the CNS by systemic administration is using a molecular Trojan horse. An example of that approach it the insulin Receptor Antibody-Iduronate 2-Sulfatase fusion protein (HIRMAb-IDS), which can cross the blood-brain barrier (BBB) via receptor-mediated transport. Intravenous administration of 3, 10 and 30 mg/kg of HIRMAb-IDS to male juvenile Rhesus monkeys weekly, for 26 weeks, resulted in a HIRMAb-IDS brain uptake of 1% of the total injected dose. See Boado et al., Biotechnol Bioeng. 2014; 111(11):2317-25. The study also demonstrated safety of the fusion protein, as no infusion-related reaction or immune response was observed.

Hematopoietic stem cell transplantation (HSCT) using bone marrow-derived stem cells (Bone marrow transplantation, BMT) has proven efficient in the treatment of both somatic and neurological pathology in patients with other MPSs. See Peters et al., Blood. 1996; 87(11):4894-902, Peters and Steward, Bone Marrow Transplant. 2003; 31(4): 229-39 and Yamada et al., Bone Marrow Transplant. 1998; 21(6):629-34. The principle underlying the correction by HSCT is that donor monocytes are able to cross the capillary wall, even at the blood-brain barrier, after which they differentiate into tissue macrophages, microglia in the case of the CNS, and secrete the deficient enzyme for delivery to the various cells. See Krivit et al., Cell Transplant. 1995; 4(4):385-92. BMT performed in MPSII mice reduced GAG accumulation in a variety of somatic tissues, including liver, spleen and lung, but not in the CNS. See Akiyama et al., Mol Genet Metab. 2014; 111(2):139-46. When BMT is combined with ERT (0.5 mg Idursulfase/kg/weekly), an additive effect on GAG levels in heart, kidney and lung was observed 7 months after treatment of MPSII mice, but accumulation of GAGs in the CNS remained at pathological levels. See Akiyama et al., Mol Genet Metab. 2014; 111(2):139-46. However, the evidence for clinical efficacy is not very strong in MPSII patients. The follow-up of 10 Hunter patients who received BMT between 1982 and 1991 showed highly varying degrees of success. See Vellodi et al., J Inherit Metab Dis. 1999; 22(5):638-48. Four of those patients died before 100 days post-BMT, and 3 more before 7 years after the procedure. Of the 3 patients that survived for more than 7 years after BMT, one of them reported no clinical benefit;

a second showed a minimal increase of IDS activity in plasma and the third failed to normalize GAG content despite having a slight increase in IDS activity in plasma. See Vellodi et al., J Inherit Metab Dis. 1999; 22(5):638-48. The Magnetic Resonance Imaging (MRI) of the brain showed a slight decrease in the number of cystic lesions 2.5 years after BMT in a patient with mild MPSII phenotype. See Seto et al., Ann Neurol. 2001; 50(1):79-92. However, the same study provided data on another patient with mild phenotype that did not show any improvement under MRI. See Seto et al., Ann Neurol. 2001; 50(1):79-92. Clinical outcomes appears to be highly variable among Hunter patients, presumably due to various factors; genotype, age at HSCT, patient's clinical status at HSCT, such as degree of neurological impairment, donor status, donor chimerism, stem cell source, and enzyme activity have all been suggested to influence the long-term outcome. See Giugliani et al., Genet Mol Biol. 2010; 33(4):589-604, Valayannopoulos et al., Rheumatology. 2011; 5:v49-59.

When successful, HSCT can contribute to some degree of clinical benefit at somatic level, decrease behavioural problems and better sleeping patterns, but whether the treatment can mediate any significant improvement of cognitive impairment remains unclear. See Giugliani et al., Genet Mol Biol. 2010; 33(4):589-604, Valayannopoulos et al., Rheumatology. 2011; 5:v49-59. In general, this approach is not recommended for Hunter patients, due to the high rate of morbidity and mortality and the variable neurocognitive benefits. See Giugliani et al., Genet Mol Biol. 2010; 33(4): 589-604.

A plausible explanation to the failure of HSCT is the limited IDS expression in engrafted cells, leading to an insufficient IDS cross-correction in the CNS. Lentiviral vectors encoding for the human IDS gene were used to transduce bone marrow cells prior to their transplantation into MPSII mice. Treated MPSII mice showed improved performance in the T-maze memory test 14 weeks post-transplant. See Podetz-Pedersen et al., Mol Ther. 2013; 21:s1-s285.

Given the limitations of current therapeutic options for MPSII, alternative approaches are needed. In vivo gene therapy offers the possibility of a one-time treatment for MPSII and other inherited diseases, with the prospect of lifelong beneficial effects. Several gene therapy approaches based on the use of different viral vectors combined with different routes of administration have been tested in animal models of MPSII disease.

Adenoassociated virus (AAV) vector-mediated gene transfer, in particular, is rapidly emerging as the approach of choice for many in vivo gene therapy applications, due to the high transduction efficiency and the lack of pathogenicity of these vectors. AAV vectors can transduce post-mitotic cells and several pre-clinical and clinical studies have demonstrated the potential of AAV vector-mediated gene transfer to efficiently drive sustained expression of therapeutic transgenes for a variety of diseases. See Bainbridge et al., N Engl J Med. 2008; 358(21):2231-9, Hauswirth et al., Hum Gene Ther. 2008; 19(10):979-90, Maguire et al., N Engl J Med. 2008; 358(21):2240-8, Niemeyer et al., Blood 2009; 113(4): 797-806, Rivera et al., Blood 2005; 105(4):1424-30, Nathawani et al., N Engl J Med. 2011; 365(25):2357-65 and Buchlis et al., Blood 2012; 119(13):3038-41.

Systemic administration of AAV5-CMV-human IDS vectors to the temporal vein of MPSII mouse pups (p2) resulted in an increase in IDS activity in heart, kidney, liver, lung, muscle and spleen, and a moderated increase in IDS activity in the brain, which led to a reduction in somatic tissue and urinary GAG content up to 18 months post a single vector administration. See Polito et al., Am J Hum Genet. 2009; 85(2):296-301. Also, this treatment prevented the development of CNS pathology by preventing neurodegeneration, and correcting astrogliosis and inflammation. The evaluation of mice in the Open Field Test 18 moths post AAV injection demonstrated the improvement with treatment in the gross motor phenotype of MPSII mice. See Polito et al., Am J Hum Genet. 2009; 85(2):296-301.

AAVs of serotype 8 encoding for the human IDS gene under the control of the liver-specific TBG promoter have also been used to treat MPSII. Up to 7 months following the intravenous administration of vectors to 2 month-old MPSII mice, an increase in serum, liver, spleen, lung, heart, kidney and muscle IDS activity was observed, resulting in complete correction of GAG storage in these somatic tissues. See Cardone et al., Hum Mol Genet. 2006; 15(7):1225-36. However, very high doses ($4 \times 10^{12}$ viral genomes/mouse) were required to achieve a slight increase in IDS activity and partial clearance of GAG accumulation in the brain when the vectors were administered intravenously. See Cardone et al., Hum Mol Genet. 2006; 15(7):1225-36. Similarly, the intravenous administration of AAV8 vectors in which the human IDS gene is under the control of the ubiquitous elongation factor 1-a (EF) promoter to adult MPSII mice demonstrated an increase in IDS activity in liver, heart, spleen and kidney up to 24 weeks after administration, with full correction of GAG accumulation in those organs. See Jung et al., Mol Cells. 2010; 30(1):13-8. IDS activity in the brain was only increased in the group of animals sacrificed at short-term (6 weeks post-injection); however, this was not sufficient to normalize GAG content in the CNS. See Jung et al., Mol Cells. 2010; 30(1):13-8.

None of aforementioned approaches has fully restored Iduronate-2-sulfatase activity, achieved full eradication of intracytoplasmic inclusions in the CNS and somatic tissues, or corrected all clinical signs of MPSII. Thus, there is a need for novel approaches to the treatment of MPSII that have better efficacy and safety profiles.

SUMMARY OF THE INVENTION

The present invention provides new nucleotide sequences for the treatment of mucopolysaccharidoses, in particular mucopolysaccharidoses type II (MPSII), or Hunter syndrome.

In a first aspect, the present invention relates to an isolated nucleotide sequence coding for the protein Iduronate-2-sulfatase (IDS) as set forth in SEQ ID NO:1 and having between 75% and 90% identity with SEQ ID NO:2. In particular, the isolated nucleotide sequences according to this first aspect of the invention are selected from SEQ ID NO:5 and SEQ ID NO:8.

In a second aspect, the present invention relates to a plasmid containing a nucleotide sequence coding for the protein Iduronate-2-sulfatase (IDS) as set forth in SEQ ID NO:1, and in particular a nucleotide sequence having at least 75% identity with SEQ ID NO:2, preferably having between 75% and 90% identity with SEQ ID NO:2.

In a third aspect, the invention provides new recombinant vectors for the treatment of mucopolysaccharidoses type II. Said recombinant vectors are in particular Adeno-associated Virus Vectors (AAV) containing a nucleotide sequence coding for the protein Iduronate-2-sulfatase (IDS) as set forth in SEQ ID NO:1, and in particular a nucleotide sequence having at least 75% identity with SEQ ID NO: 2, preferably having between 75% and 90% identity with SEQ ID NO:2.

In a preferred embodiment, the Adenoassociated Virus Vectors are of serotype 9 (AAV9). The AAV9 vectors of the present invention may further contain a promoter linked to the coding nucleotide sequence in order to control the expression of IDS. A suitable promoter is the CAG promoter, SEQ ID NO: 14.

A further aspect of the present invention relates to a pharmaceutical composition comprising a therapeutically effective amount of the nucleotide sequence or the plasmid or the recombinant vector described herein.

Still, a further aspect of the invention relates to the nucleotide sequences of the invention or a plasmid described herein, or a recombinant vector described herein for use as a medicament, in particular for the treatment of mucopolysaccharidoses type II.

The present invention also provides a method for the production of the plasmids according to the invention, as well as a method for the production of the recombinant vectors according to the invention.

In a further aspect, the invention relates to isolated cells comprising the nucleotide sequence coding for IDS, and in particular a nucleotide sequence having at least 75% identity with SEQ ID NO: 2, preferably having between 75% and 90% identity with SEQ ID NO:2.

Figure 1:
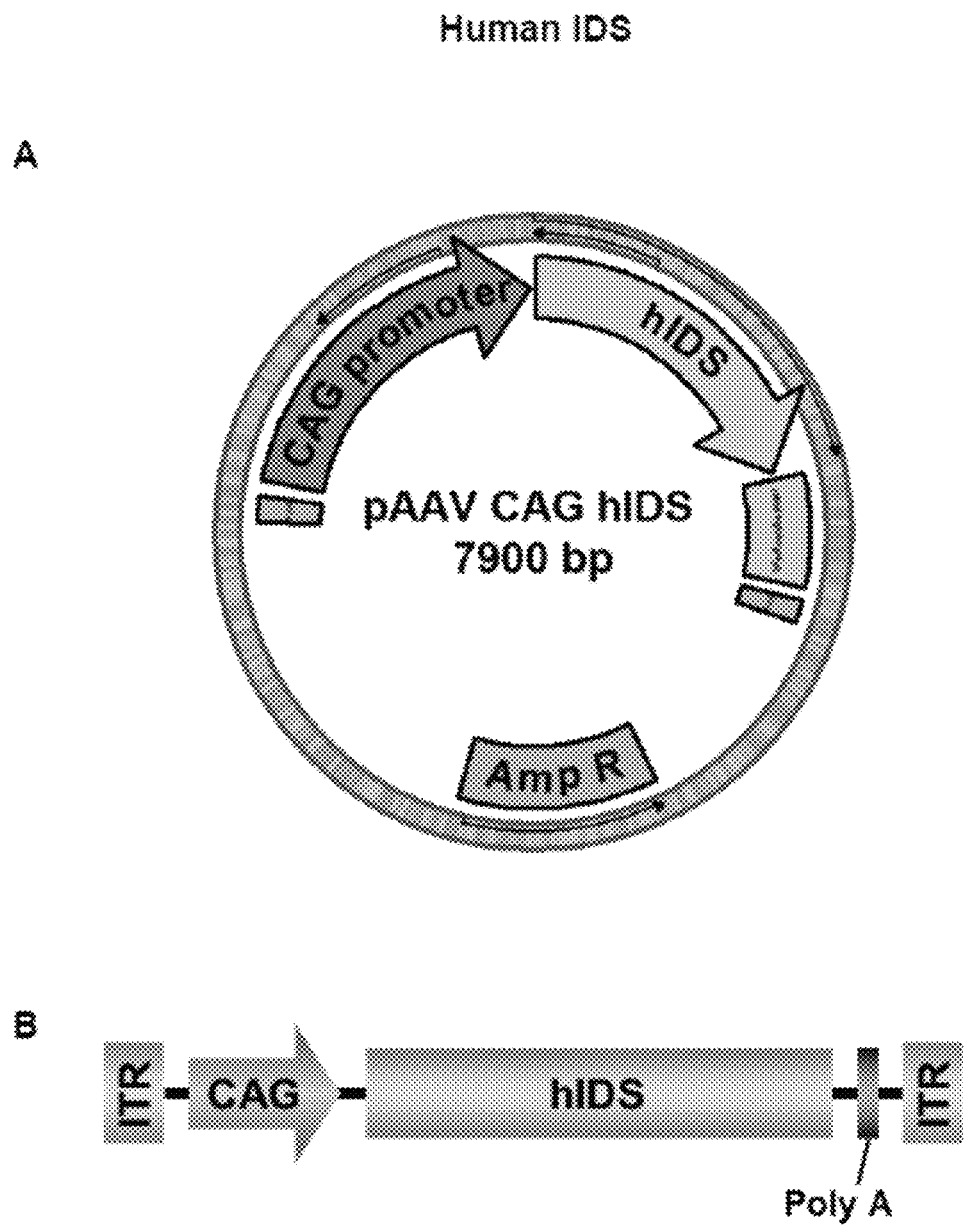
FIG. 1. Generation of pAAV-CAG-hIDS and AAV-CAG-hIDS. (A) Schematic representation of the plasmid pAAV-CAG-hIDS and its components. (B) Schematic representation of the genome of an Adeno-associated vector containing the hIDS coding sequence.

of wild-type (healthy) mice, untreated MPSII mice and MPSII mice administered in the CSF with different doses of AAV9-CAG-omIDS vector at 2 months of age and analysed 1.5 months later. WT IDS activity was set to 100%. (C) Quantification of glycosaminoglycans (GAGs) in somatic organs. Results are shown as means±SEM of 5 mice per group. * P<0.05,  P<0.01, * P<0.001, **** P<0.0001 vs. untreated MPSII.

DEPOSIT OF MICROORGANISMS

The plasmids pAAV-CAG-hIDS (SEQ ID NO: 3), pAAV-CAG-ohIDS-version1 (SEQ ID NO: 6) and pAAV-CAG-ohIDS-version2 (SEQ ID NO: 9) were deposited on Dec. 18, 2014, under access number DSM 29866, DSM 29867 and DSM 29868 at the DSMZ-Deutsche Sammlung von Mikroorganismen und Zellkulturen, Inhoffenstraße 7 B, D-38124 Braunschweig, Federal Republic of Germany.

Applicant has deposited plasmids disclosed herein with the Leibniz Institute DSMZ-German Collection of Microorganisms and Cell Cultures. Inhoffenstr. 7 B, D-38124, Braunschweig, GERMANY under the terms of the Budapest Treaty. The accession numbers for the deposits are DSM 29866, the date of deposit is 18 Dec. 2014; DSM Accession No. 29867, the date of deposit is 18 Dec. 2014; DSM Accession No. 29868, the date of deposit is 18 Dec. 2014.

Definitions

The term "nucleotide sequence" or "isolated nucleotide sequence" refers to a nucleic acid molecule, either DNA or RNA, containing deoxyribonucleotides or ribonucleotides respectively. The nucleic acid may be double stranded, single stranded, or contain portions of both double stranded or single stranded sequence.

The term "% sequence identity" or "% identity" refer to the percentage of nucleotides of a candidate sequence that are identical to the nucleotides in the sequence of reference, after aligning the sequences to achieve the maximum % sequence identity. The % sequence identity can be determined by any methods or algorithms established in the art, such as the ALIGN, BLAST and BLAST 2.0 algorithms. See Altschul S, et al., Nuc Acids Res. 1977; 25:3389-3402 and Altschul S, et al., J Mol Biol. 1990; 215:403-410.

Herein, the % sequence identity or "% identity" is calculated dividing the number of nucleotides that are identical after aligning the sequence of reference and the candidate sequence, by the total number of nucleotides in the sequence of reference and multiplying the result by 100.

The terms "codify" or "coding" refer to the genetic code that determines how a nucleotide sequence is translated into a polypeptide or a protein. The order of the nucleotides in a sequence determines the order of amino acids along a polypeptide or a protein.

The term "protein" refers to a macromolecule composed of one or more linear chains of amino acids or polypeptides. Proteins can suffer post-translational modifications, like the conversion of a cysteine residue to 3-oxoalanine, glycosylation or metal binding. Glycosylation of a protein is the addition of different carbohydrates that are linked covalently to the amino acid chain.

The term "effective amount" refers to an amount of a substance sufficient to achieve the intended purpose. For example, an effective amount of an AAV9 vector to increase iduronate-2-sulfatase (IDS) activity is an amount sufficient to reduce glycosaminoglycan accumulation. A "therapeutically effective amount" of an expression vector to treat a disease or disorder is an amount of the expression vector sufficient to reduce or eradicate the signs and symptoms of the disease or disorder. The effective amount of a given substance will vary with factors such as the nature of the substance, the route of administration, the size and species of the animal to receive the substance and the purpose of giving the substance. The effective amount in each individual case may be determined empirically by a skilled artisan according to established methods in the art.

The term "individual" refers to a mammal, preferably human or non-human mammal, more preferably mouse, rat, other rodents, rabbit, dog, cat, pig, cow, horse or primate, further more preferably human.

The term "operably linked" refers to the functional relation and the location of the promoter sequence with respect to the gene of interest (e.g. a promoter or enhancer is operably linked to a coding sequence if it affects the transcription of the sequence). Generally, a promoter operably linked is contiguous to the sequence of interest. However, an enhancer does not have to be contiguous to the sequence of interest to control its expression.

The term "tropism" refers to the way in which different viruses have evolved to preferentially target specific host species, or specific cell types within those species.

The term "gene therapy" refers to the transfer of genetic material (e.g. DNA or RNA) of interest into a cell to treat or prevent a genetic or acquired disease or condition. The genetic material of interest encodes a product (e.g. a protein polypeptide, peptide or functional RNA) whose production in vivo is desired. For example, the genetic material of interest can encode an enzyme, hormone, receptor, or polypeptide of therapeutic value.

The term "recombinant viral vector" or "viral vector" refers to an agent obtained from a naturally-occurring virus through genetic engineering techniques capable of transferring genetic material (e.g. DNA or RNA) of interest to a cell, which results in production of the product encoded by that said genetic material (e.g. a protein polypeptide, peptide or functional RNA) in the target cell.

The term "recombinant plasmid" or "plasmid" refers to a small, circular, double-stranded, self-replicating DNA molecule obtained through genetic engineering techniques capable of transferring genetic material of interest to a cell, which results in production of the product encoded by that said genetic material (e.g. a protein polypeptide, peptide or functional RNA) in the target cell. Furthermore, the term "recombinant plasmid" or "plasmid" also refers to a small, circular, double-stranded, self-replicating DNA molecule obtained through genetic engineering techniques used during the manufacturing of viral vectors as carriers of the recombinant vector genome.

DETAILED DESCRIPTION OF THE INVENTION

The present invention provides new nucleotide sequences for the treatment of mucopolysaccharidoses, in particular mucopolysaccharidoses type II (MPSII), or Hunter syndrome.

The nucleotide sequences according to the present invention codify for the protein Iduronate-2-sulfatase (referred to as IDS) as set forth in SEQ ID NO:1, enzyme involved in the stepwise degradation of the glycosaminoglycans heparan sulphate and dermatan sulphate. The "natural IDS" or "wild type IDS" terms refer in the context of the invention to a nucleotide sequence obtained or produced from host cells using methods known to those skilled in the art, or alternatively chemically synthetized using as starting material the coding sequence (CDS) for IDS of each species. Preferably, "natural IDS" or "wild type IDS" are chemically synthetized from the murine CDS (referred to as mIDS) or from the humans CDS (referred to as hIDS). More preferably the nucleotide sequence hIDS is chemically synthetized from human CDS and corresponds to SEQ ID NO: 2.

According to the present invention, evidence establishes that modified nucleotide sequences, also referred to as optimized nucleotide sequences, mediate the production of greater amounts of protein of interest, likely due to efficient transcription of mRNA or the transcription of a more stable mRNA, or the more efficient usage of codons. These sequences are referred herein also as "optimized sequences"; omIDS and ohIDS, when obtained from murine and human CDS, respectively. Advantageously, optimized sequences according to the present invention are codon optimized sequences.

Thus a first aspect of the invention relates to an isolated nucleotide sequence coding for the protein Iduronate-2-sulfatase (IDS) as set forth in SEQ ID NO:1 and having between 75% and 90% identity with SEQ ID NO:2. In particular, the isolated nucleotide sequence according to the invention has 75%, 76%, 77%, 78%, 79%, 80%, 82%, 85%, 87% or 90% identity with SEQ ID NO:2. In a preferred embodiment, the isolated nucleotide sequences of the present invention are selected from ohIDS-version1 as set forth in SEQ ID NO:5 and ohIDS-version2 as set forth in SEQ ID NO:8.

In accordance with the present invention, the isolated sequences described hereinbefore may be inserted into a multiple cloning site (MCS) of a backbone plasmid. In particular the backbone plasmid is a plasmid that contains the ITRs of the Adeno-associated Virus (AAV), referred to as pAAV herein.

A second aspect of the invention provides a plasmid containing a nucleotide sequence coding for the protein Iduronate-2-sulfatase (IDS) as set forth in SEQ ID NO:1 and having at least 75% identity with SEQ ID NO:2. Advantageously, the plasmid according to the present invention has between 75% and 90% identity with SEQ ID NO:2. In particular, the plasmid according to the invention contains an isolated nucleotide sequence having 75%, 76%, 77%, 78%, 79%, 80%, 82%, 85%, 87% or 90% identity with SEQ ID NO:2. In a preferred embodiment, the plasmid of the present invention contains a nucleotide sequence selected from hIDS as set forth in SEQ ID NO:2, ohIDS-version1 as set forth in SEQ ID NO:5 and ohIDS-version2 as set forth in SEQ ID NO:8.

In addition to the isolated sequences mentioned above, the plasmids according to the present invention also include conventional control elements which may be operably linked to the nucleotide sequence in a way that allows its transcription, translation and/or expression in a cell transfected with the plasmids. In particular, the plasmids according to the present invention contain a promoter as control element operably linked to the nucleotide sequence of interest. A great number of promoters, which are native or chimeric, constitutive or inducible, ubiquitous and/or tissue-specific are known in the art. Advantageously, the promoter used in the context of the present invention is the CAG promoter which refers to the combination comprising the cytomegalovirus early enhancer element and the chicken B-actin promoter. It further includes portions of the chicken B-actin and rabbit B-globin introns that confer stability to the mRNA derived from the nucleotide sequence of interest, See Alexopoulou A, et al., BMC Cell Biology 2008; 9(2): 1-11. The CAG promoter included in the pAAV plasmids of the present invention has a sequence SEQ ID NO:14. This specific CAG promoter allows a long-lasting expression of the missing enzyme in all areas of the brain and in the liver. As a consequence the lysosomal accumulation of glycosaminoglycan (GAG) is corrected, preventing in this way the neurological and somatic alterations characteristic of MPSII.

In a particularly advantageous embodiment, the plasmid according to the invention is the plasmid pAAV-CAG-hIDS, as set forth in SEQ ID NO:3 with access number DSM 29866.

In another particularly advantageous embodiment, the plasmid according to the invention is the plasmid pAAV-CAG-ohIDS-version1, as set forth in SEQ ID NO:6 with access number DSM 29867.

In another particularly advantageous embodiment, the plasmid according to the invention is the plasmid pAAV-CAG-ohIDS-version2, as set forth in SEQ ID NO:9 with access number DSM 29868.

A third aspect of the invention relates to new recombinant vectors for the treatment of mucopolysaccharidoses type II. It has to be understood that a vector of the present invention is a capsid protein as well as a vector genome contained within, used to transfer a genetic material of interest into a cell. Apart from said genetic material of interest, the genome of the vector may also contain different functional elements that include control elements for transcription such as promoters or operators, transcription factors binding regions or enhancers and control elements for the initiation or termination of translation.

The vectors according to the invention are derived from Adeno-associated viruses (AAV) and are used to transfer the nucleotide sequence of interest into a target cell. They have proved to have a high efficiency in transducing post-mitotic cells in a wide range of tissues. In the context of the present invention, the vectors are used to deliver the human Iduronate-2-sulfatase coding sequence (hIDS of SEQ ID NO: 2) or an optimized version of the human Iduronate-2-sulfatase coding sequence, (ohIDS-version1 of SEQ ID NO: 5 or ohIDS-version2 of SEQ ID NO: 8). An adeno-associated vector is a vector derived from an adeno-associated virus of the family of parvoviridae. The adenoassociated virus genome is built of single-stranded deoxyribonucleic acid (ssDNA). These viruses infect mammals but are non-pathogenic (i.e. do not cause disease). They can infect dividing or non-dividing cells, and their tropism changes depending on the serotype. The serotype is the classification of the viruses groups, depending on their capsid antigens. The serotype of adeno-associated virus, determined by its capsid protein, defines the virus tropism and allows its entry into a specific cell type. In the context of the present invention, the AAV has a serotype 1, 2, 5, 7, 8, 9 or 10. Preferably, the AAV is of serotype 9 (AAV9), since it shows the best ability to deliver the genetic material to the brain as well as to peripheral organs upon a single administration to the CSF. The AAV9 vectors of the present invention are composed of the viral capsid of the serotype 9 of human adenoassociated virus and a modified genome, containing the Inverted Terminal Repeats (ITRs) of human adenoassociated virus serotype 2, the CAG promoter, the coding sequence of the human Iduronate-2-sulfatase (hIDS) gene or an optimized version of it (also referred to as nucleotide sequence according to the present invention), and the polyA from the rabbit beta-globin gene.

Thus in this aspect the invention relates to a recombinant AAV containing a nucleotide sequence coding for the protein Iduronate-2-sulfatase (IDS) as set forth in SEQ ID NO:1 and having at least 75% identity with SEQ ID NO:2. Advantageously, the recombinant AAV according to the invention contains between 75% and 90% identity with SEQ ID NO:2. In particular the recombinant AAV according to the invention contains a nucleotide sequence according to the invention having 75%, 76%, 77%, 78%, 79%, 80%, 82%, 85%, 87% or 90% identity with SEQ ID NO:2. In a preferred embodiment, the isolated nucleotide sequences contained in the recombinant AAV of the present invention are selected from hIDS as set forth in SEQ ID NO:2, ohIDS-version1 as set forth in SEQ ID NO:5 and ohIDS-version2 as set forth in SEQ ID NO:8.

In an advantageous embodiment of this aspect, the present invention relates to a recombinant AAV9 containing a nucleotide sequence coding for the protein Iduronate-2-sulfatase IDS as set forth in SEQ ID NO:1 and having at least 75% identity with SEQ ID NO:2. Preferably, the recombinant AAV9 of the invention contains a nucleotide sequence having between 75% and 90% identity with SEQ ID NO:2. In particular the recombinant AAV9 of the invention contain a nucleotide sequence according to the invention having 75%, 76%, 77%, 78%, 79%, 80%, 82%, 85%, 87% or 90% identity with SEQ ID NO:2. In a preferred embodiment, the recombinant AAV9 of the invention contains the nucleotide sequences selected from hIDS as set forth in SEQ ID NO:2, ohIDS-version1 as set forth in SEQ ID NO:5 and ohIDS-version2 as set forth in SEQ ID NO:8.

It has further been surprisingly found that the association, in the same entity, of the AAV9 capsid with a nucleotide sequence coding for the Iduronate-2-sulfatase (IDS), together with a chosen promoter, especially the CAG promoter, allows a long-lasting expression of the missing enzyme in all areas of the brain, in particular when the entity is delivered to the cerebrospinal fluid (CSF) through intra-cisternal injection. As a consequence the lysosomal accumulation of glycosaminoglycan (GAG) is corrected, preventing by that way the neurological alterations characteristic of the MSPII disease. This effect has been observed even in the olfactory bulb, which is distant from the point of administration of the vectors (cisterna magna). Further the AAV9 vectors according to the invention delivered into the CSF were able to reach the systemic circulation to transduce the liver. The production and secretion of the enzyme by liver cells resulted in an increase of Iduronate-2-sulfatase (IDS) activity in serum, ultimately leading to the reduction of lysosomal pathology in many somatic tissues. This represents a clear advantage of the vectors according to the invention over the existing approaches that only partially corrected the clinical signs of the disease and usually exert their effect either in the brain or in the systemic circulation, but not in both.

Accordingly the present invention relates to AAV9 vectors containing a CAG promoter linked to a nucleotide sequence coding for protein Iduronate-2-sulfatase (IDS) as set forth in SEQ ID NO:1.

In particular the AAV9 vectors of the present invention contain a CAG promoter linked to a nucleotide sequence coding for the protein iduronate-2-sulfatase (IDS) as set forth in SEQ ID NO:1 and having at least 75% identity with SEQ ID NO:2. Advantageously, the AAV9 vectors of the invention contain a CAG promoter linked to a nucleotide sequence coding for the protein iduronate-2-sulfatase (IDS) as set forth in SEQ ID NO:1 and having between 75% and 90% identity with SEQ ID NO:2. In particular the nucleotide sequence contained in the AAV9 vector according to the invention has 75%, 76%, 77%, 78%, 79%, 80%, 82%, 85%, 87% or 90% identity with SEQ ID NO:2.

In a preferred embodiment, the recombinant vector of the present invention is the AAV9-CAG-hIDS (SEQ ID NO: 4) containing the nucleotide sequence SEQ ID NO:2 operably linked to the CAG promoter of SEQ ID NO:14.

In another preferred embodiment, the recombinant vector of the present invention is the AAV9-CAG-ohIDS-version1 (SEQ ID NO: 7) containing the nucleotide sequence SEQ ID NO:5 operably linked to the CAG promoter of SEQ ID NO:14.

In another preferred embodiment, the recombinant vector of the present invention is the AAV9-CAG-ohIDS-version2 (SEQ ID NO: 10) containing the nucleotide sequence SEQ ID NO:8 operably linked to the CAG promoter of SEQ ID NO:14.

The recombinant vectors of the invention as defined hereinbefore may be obtained from the corresponding plasmids also described hereinbefore by transfection of HEK293 cells using methods known in the state of the art.

Thus the present invention further provides a method for the production of the adenoassociated viral vectors AAV according to the invention, and especially a AAV9. The process comprises the steps of:
  i) providing a first plasmid comprising the sequence coding for the protein of interest interposed between a first AAV terminal repeat and a second AAV terminal repeat, a CAG promoter operably linked to the sequence coding for the protein of interest; a second vector comprising an AAV rep gene and a AAV cap gene, and a third vector comprising the adenovirus helper function genes;
  ii) co-transfection of competent cells with the vectors of step i);
  iii) culture of the transfected cells of step ii) for a period of time sufficient to produce viral particles; and
  iv) purification of the vectors from the culture of step iii).

In a preferred embodiment, the AAV first and second terminal repeats of the first vector are ITRs from the AAV serotype 2. In another preferred embodiment, the AAV rep genes of the second vector are from the AAV serotype 2. In another preferred embodiment, the competent cells are HEK293 cells. In another preferred embodiment, the AAV cap genes of the second vector are from the AAV serotype 9.

The invention also provides a method for the preparation of the plasmid according to the invention, comprising the steps of:
  i) excising the sequence coding for the protein of interest from the starting plasmid, by digestion, in particular using MluI/EcoRI,
  ii) cloning the sequence coding for the protein of interest between two restriction sites of the AAV backbone plasmid pAAV-CAG, hereby obtaining the corresponding plasmid including the sequence coding for the protein of interest.

The present invention contemplates, in an additional aspect, pharmaceutical compositions containing a therapeutically effective amount of the isolated nucleotide sequences described herein, the plasmids as described herein, or the AAV vectors, especially AAV9 vectors, described herein.

Pharmaceutical compositions of the invention comprise the isolated nucleotide sequences described herein, the plasmids as described herein, or the AAV vectors described herein in a pharmaceutically acceptable carrier. The composition may also comprise at least one auxiliary substance. The auxiliary substances can be selected among carriers, excipients, solvents, diluents, or adjuvants. Acceptable carriers, diluent or adjuvants are non-toxic and are preferably inert at the dosage and concentrations employed and include buffers such as phosphate, citrate or other organic acids; antioxidants; low molecular weight polypeptides, proteins such as serum albumin, gelatin or immunoglobulins; hydrophilic polymers; amino acids; monosaccharides, disaccharides and other carbohydrates including glucose, mannose or dextrins; chelating agents; sugar alcohols such as mannitol or sorbitol, salt forming counterions such as sodium; and/or non-ionic surfactants such as polyethylene-polyoxypropylene block copolymer (Pluronic F68®) and polyethylene glycol (PEG).

In a preferred embodiment, the pharmaceutical compositions according to the invention are suitable for parenteral administration. Examples of parenteral administration are intravenous, subcutaneous, intracisternal and intramuscular injections. Preferably, the pharmaceutical composition according to the invention is suitable for intravenous or intracisternal administration. Compositions suitable for such parenteral administration include sterile aqueous solutions or dispersions, sterile powders for extemporaneous preparation of sterile solutions or dispersions. Advantageously the pharmaceutical compositions according to the invention are preserved from contaminating action of bacteria and fungi.

The dosage for humans and animals may vary depending on factors that have their basis in the respective species or other factors, such as age, sex, weight or degree of illness and so forth.

Still a further aspect of the present invention relates to the therapeutical use of the isolated nucleotide sequences described herein, the plasmids as described herein, or the AAV vectors, especially AAV9 vectors, described herein. As mentioned above, the isolated nucleotide sequences, the plasmids as described herein, or the AAV vectors, especially AAV9 vectors according to the invention mediate expression of the missing IDS enzyme, thus correcting the lysosomal accumulation of GAGs. This allows correcting all clinical signs of mucopolysaccharidoses type II (MPSII). In this respect, the present invention also concerns the isolated nucleotide sequences described herein, the plasmids as described herein, or the AAV vectors, especially AAV9 vectors, described herein for use as a medicament.

In particular, the invention relates to the isolated nucleotide sequences described herein, the plasmids as described herein, or the AAV vectors, especially AAV9 vectors, described herein for increasing iduronate-2-sulfatase (IDS) activity in the body.

In a further preferred aspect, the present invention relates to the isolated nucleotide sequences described herein, the plasmids as described herein, or the AAV vectors, especially AAV9 vectors, described herein for treatment of mucopolysaccharidoses type II (MPSII).

In a still further embodiment, the present invention relates to the use of the isolated nucleotide sequences described herein, the plasmids as described herein, or the AAV vectors, especially AAV9 vectors, described herein for the manufacture of a medicament useful for the treatment of mucopolysaccharidoses type II (MPSII).

Another embodiment of the present invention is directed to the method of treatment of mucopolysaccharidoses type II (MPSII), comprising the step of administering at least an isolated nucleotide sequences described herein, a plasmid as described herein, or an AAV vectors, especially AAV9 vectors, described herein to a subject in need thereof.

The present invention further provides an isolated cell comprising the nucleotide sequence coding for Iduronate-2-sulfatase SEQ ID NO: 1. In particular the cell according to the invention comprises a nucleotide sequence coding for the protein Iduronate-2-sulfatase (IDS) as set forth in SEQ ID NO:1 and having at least 75% identity with SEQ ID NO:2, and advantageously between 75% and 90% identity with SEQ ID NO:2. In particular the nucleotide sequence contained in the isolated cell according to the invention has 75%, 76%, 77%, 78%, 79%, 80%, 82%, 85%, 87% or 90% identity with SEQ ID NO:2.

In a preferred embodiment the cells of the invention comprise the nucleotide sequence SEQ ID NO: 2 coding for Iduronate-2-sulfatase (IDS) SEQ ID NO: 1.

In another preferred embodiment the cells of the invention comprise the nucleotide sequence SEQ ID NO: 5 coding for Iduronate-2-sulfatase (IDS) SEQ ID NO: 1.

In another preferred embodiment the cells of the invention comprise the nucleotide sequence SEQ ID NO: 8 coding for Iduronate-2-sulfatase (IDS) SEQ ID NO: 1.

The following examples are merely illustrative of certain embodiments of the invention and cannot be considered as restricting in any way.

General Procedures

1. Recombinant AAV Vectors

The AAV vectors described herein were obtained by triple transfection. The materials required for making the vectors were: HEK293 cells (expressing adenoviral E1 genes), helper plasmid providing adenovirus function, plasmid providing AAV rep genes from serotype 2 and cap genes from serotype 9 (AAV9) and, finally, the backbone plasmid with AAV2 ITRs and the construct of interest.

To generate Iduronate-2-sulfatase-expressing AAV vectors, the optimized or non-optimized coding sequences of human or murine Iduronate-2-sulfatase were cloned into an AAV backbone plasmid under the control of the ubiquitous hybrid CAG promoter. Large-scale production of plasmids was done using an EndoFree Plasmid Megaprep Kit (Qiagen).

Vectors were generated by helper virus-free transfection of HEK293 cells using three plasmids with modifications. See Matsushita T, et al., Gene Ther. 1998; 5:938-945 and Wright J, et al., Mol. Ther. 2005; 12:171-178. Cells were cultured to 70% confluence in roller bottles (RB) (Corning, Corning, N.Y., US) in DMEM supplemented with 10% FBS and then co-transfected with: 1) a plasmid carrying the expression cassette flanked by the viral ITRs of serotype 2 AAV (described above); 2) a plasmid carrying the AAV rep2 and the cap9 genes; and 3) a plasmid carrying the adenovirus helper functions. Vectors were purified by two consecutives cesium chloride gradients using an optimized protocol as previously described. See Ayuso E, et al., Gene Ther. 2010; 17:503-510. Vectors were dialyzed against PBS+0.001% Pluronic® F68, filtered, titred by qPCR and stored at −80° C. until use.

The vectors of the present invention were constructed according to molecular biology techniques well known in the art.

2. Animals

An Iduronate-2-sulfatase-deficient mouse (MPSII) model was purchased from Taconic (Germantown, N.Y. 12526 USA, Stock TF1838). Affected MPSII and healthy control mice were inbred from hemizygous males and heterozygous female founders. Genotype was determined on genomic DNA from tail-clipped samples with a PCR analysis that amplifies a sequence encompassing the targeted mutation. The sequences of the respective sense and antisense primers were: Forward Primer: 5'-TTT TGT GTA CTC CAA CCC CG-3' (SEQ ID NO:15), Reverse Primer: 5'-TGT CTC CAT AAC AGC CCA GG-3' (SEQ ID NO:16), Reverse Primer Mutation: 5'-GCC CTC ACA TTG CCA AAG GA-3' (SEQ ID NO:17). Mice were fed ad libitum with a standard diet (Harlan, Tekland) and maintained under a light-dark cycle of 12 h (lights on at 9:00 A.M.).

3. Hydrodynamic Delivery of IDS-Encoding Plasmids to Mice

For hydrodynamic delivery of pAAV-CAG-hIDS, pAAV-CAG-ohIDS-version1 and pAAV-CAG-ohIDS-version2 plasmids, 3-month-old MPSII and wild-type animals received through tail vein injection in <5 seconds a total dose of 30 µg of plasmid in a volume equal to 10% of the body weight of the animal. This technique results in expression of plasmid-encoded transgenes mainly in the liver. See Liu et al., Gene Ther. 1990; 6(7):1258-66. As control, a cohort of mice received and equal volume of saline solution. Mice were divided into two cohorts, and sacrificed either at 48 hours or 1 week after hydrodynamic injection of the plasmids. Organs were harvested as described in the following section.

4. Vector Administration to Mice

For intra-CSF delivery of AAV9-CAG-omIDS vectors to mice, a total dose of $5 \times 10^{10}$ vg were injected to the cisterna magna of 2-month-old MPSII animals. A similar cohort of animals was injected with $5 \times 10^{10}$ vg control non-coding (AAV9-Null) vector. At 6 and 10 months of age, i.e. 4 and 8 months post vector administration, mice were anesthetized and tissues were harvested.

For the intravenous delivery of AAV9 vectors containing the wild-type hIDS or either of the optimized versions of the IDS coding sequence to mice, a total dose of $1 \times 10^{10}$ vg of vector were injected in the tail vein of 3.5-month-old MPSII animals. WT and untreated MPSII animals served as controls. Three weeks after vector administration, mice were anesthetized and tissues were harvested.

5. Sample Collection

At sacrifice, animals were deeply anesthetized and then transcardially perfused with 12 ml of PBS to completely clear blood from tissues. The entire brain and multiple somatic tissues (including liver, spleen, pancreas, kidney, lung, heart, skeletal muscle, testicles, urinary bladder, intestine and adipose tissue) were collected and either frozen in liquid nitrogen and stored at −80° C. or immersed in formalin for subsequent histological analyses.

6. Iduronate-2-Sulfatase Activity and Glycosaminoglycan Quantification

Brain, liver, lung and heart samples were sonicated in Mili-Q water. Serum was analysed unprocessed. Iduronate-2-sulfatase activity was determined with a 4-methylumbelliferone-derived fluorogenic substrate (Moscerdam Substrates, Oegstgeest, NL), as described previously. See Voznyi et al., J Inher Metab Diss 2001; 24:675-680. Brain, liver, lung and heart activity levels were normalized against the total amount of protein, quantified using Bradford protein assay (Bio-Rad, Hercules, Calif., US). Serum activity was normalized against volume.

For glycosaminoglycan (GAG) quantification, tissue samples were weighted and then digested with proteinase K and extracts were clarified by centrifugation and filtration. GAG levels were determined in tissue extracts with the Blyscan sulfated glycosaminoglycan kit (Biocolor, Carrickfergus, County Antrim, GB), using chondroitin 4-sulfate as standard. The levels of GAG were normalized to wet tissue weight.

7. Activity of Other Lysosomal Enzymes

Brain and liver samples were sonicated in 500 µl of Mili-Q water and enzyme activities were determined in supernatants using 4-methylumbelliferone-derived fluorogenic substrates. Serum was analysed unprocessed. IDUA activity was assayed in 15 µg of protein incubated for 1 h at 37° C. with 4-methylumbelliferyl α-L-iduronide (Glycosynth). See Bacter et al., Blood 2002; 99(5)1857-9. SGSH activity was measured as previously described. See Karpova et al., J Inherit Metab Dis. 1996; 19(3):278-285, Haurigot et al., supra. Briefly, 30 µg of protein were first incubated with 4-MU-αGlcNS for 17 hours at 47° C. The second incubation was carried out in the presence of 10 U/ml of α-glucosidase (Sigma-Aldrich) in 0.2% BSA for 24 hours at 37° C. For NAGLU activity, 30 µg of tissue protein extract were incubated with 4-methylumbelliferyl-α-N-acetyl-D-glucosaminide (Moscerdam Substrates) for 3 h at 37° C., as previously described. See Marsh et al., Clin Genet. 1985; 27(3):258-62, Ribera et al., supra. HGSNAT activity was determined from 30 µg of protein extract incubated with Acetylcoenzyme A and 4-methylumbelliferyl-β-D-glucosamine (MU-βGlcNH$_2$, Moscerdam Substrates) for 17 h at 37° C. See Voznyi et al., J Inh Metab Dis 1993; 16:465-72. GALNS activity was assayed by a 2-step protocol using 10 µg of protein extract and 4-Methylumbelliferyl β-D-Galactopyranoside-6-sulfate Sodium Sal (MU-βGal-6S) during the first incubation for 17 h at 37° C. The second step was carried out adding P$_i$-buffer (0.9M Na$_2$HPO$_4$/0.9M NaH$_2$PO$_4$ buffer, pH4.3+0.02% (w/v) Na-azide) and β-Galactosidase (β-Gal-Ao, Sigma) and incubating the mix for 2 h at 37° C. See van Diggelen et al., Clin Chim Acta 1990; 187:131-40. The activity of GUSB enzyme was determined from 10 µg of protein extract incubated with 4-methylumbelliferyl-β-D-glucuronide (Sigma) at 37° C. for 1 h. HEXB activity was assayed by incubation of 0.1 µg of protein extract with 4-methylumbelliferyl N-acetyl-β-D-glucosaminide (Sigma) for 1 h at 37° C. After stopping reactions by increasing the pH, released fluorescence was measured with FLx800 fluorimeter (BioTek Instruments). All brain and liver activities levels were normalized against the total amount of protein, quantified using Bradford protein assay (Bio-Rad, Hercules, Calif., US).

8. Histological Analysis

Tissues were fixed for 12-24 h in formalin, embedded in paraffin and sectioned. For immunohistochemical detection of LAMP2 in brain, paraffin sections were subjected to heat-induced epitope retrieval in citrate buffer, pH 6, and then incubated overnight at 4° C. with rat anti-LAMP2 antibody (Ab13524; Abcam, Cambridge, UK) diluted at 1:500 and subsequently incubated with biotinylated rabbit anti-rat antibody (Dako, Glostrup, DK) at 1:300. For GFAP immunostaining in brain samples, paraffin sections were incubated overnight at 4° C. with rabbit anti-GFAP antibody (Ab6673; Abcam, Cambridge, UK) diluted at 1:1000 and subsequently incubated with biotinylated goat anti-rabbit antibody (31820; Vector Laboratories, Burlingame, Calif., USA) at 1:300. LAMP2, and GFAP signals were amplified by incubating sections with ABC-Peroxidase staining kit (Thermo Scientific, Waltham, Mass., US) at 1:100 dilution and visualized using 3,3-diaminobenzidine (Sigma-Aldrich, St. Louis, Mo., US) as a chromogen.

To stain microglial cells in brain samples, paraffin sections were incubated overnight at 4° C. with BSI-B4 lectin (L5391; Sigma-Aldrich, St. Louis, Mo., USA) diluted at 1:100. BSI-B4 signal was visualized using 3,3-diaminobenzidine (Sigma-Aldrich, St. Louis, Mo., US) as a chromogen. Brightfield images were obtained with an optical microscope (Eclipse 90i; Nikon, Tokyo, JP).

The NIS Elements Advanced Research 2.20 software was used to quantify LAMP2, GFAP, and BSI-B4 signals in 3-4 images of each brain region (original magnification, ×20) per animal, using the same signal threshold settings for all animals. Then, the percentage of positive area was calculated, i.e., the area, in pixels, with a positive signal over the total tissue area in the image.

9. Quantification of Vector Genome Copy Number in Tissues

After an overnight tissue digestion in Proteinase K (0.2 mg/ml), total DNA was isolated with MasterPureDNA Purification Kit (Epicenter). Quantitative PCR with primers and probe specific for the HBB2 sequence (contained in the polyA segment) were used to quantify the vector genome copy numbers in 20 ng of total DNA. Forward primer: 5'-CTT GAG CAT CTG ACT TCT GGC TAA T-3' (SEQ ID NO: 18); reverse primer: 5'-GAT TTG CCC TCC CAT ATG TCC-3' (SEQ ID NO: 19); probe: 5'-CCG AGT GAG AGA CAC AAA AAA TTC CAA CAC-3' (SEQ ID NO: 20). Reference standard curve built by serial dilutions of the linearized plasmid containing polyA sequence was used to interpolate the final values of vg/sample.

10. Open Field Test

The behavior of 6-month-old mice was analyzed by the Open Field test performed between 9:00 am and 1:00 pm. Animals were placed in the lower left corner of a brightly lit chamber (41×41×30 cm) crossed by 2 bundles of photo-beams (SedaCom32; Panlab) that detected horizontal and vertical movements of the mice. The area surface was divided into three squared concentric regions: center (14×14 cm), periphery (27×27 cm) and border (41×41 cm). Exploratory and motor activities were recorded during the first 3 minutes of the test using a video-tracking system (SmartJunior, Panlab).

11. Statistical Analysis

All results are expressed as mean±SEM. Statistical comparisons were made using one-way ANOVA. Multiple comparisons between control and treatment groups will be made using Dunnett's post test, and between all groups using Tukey's post test. Statistical significance was considered if $P<0.05$. Kaplan-Meier curves were used to estimate survival and the long-rank test was used for comparisons.

EXAMPLES

Example 1: Construction of pAAV-CAG-hIDS

The CDS for human Iduronate-2-sulfatase was utilized as starting material (NCBI Reference Sequence: NM_000202.6) and chemically synthetized for this purpose (GenScript Inc). The CDS was received cloned inside the plasmid pUC57_(AmpR) flanked by SwaI restriction sites.

The SwaI-SwaI human Iduronate-2-sulfatase CDS fragment was excised from the pUC57 plasmid and subsequently cloned between the MluI and EcoRI restrictions sites of the AAV backbone plasmid pAAV-CAG after rendering the 5' and 3' overhangs blunt with Klenow fragment (Fermentas). The resulting plasmid was named pAAV-CAG-hIDS (accession number DSM 29866). See FIG. 1A and SEQ ID NO:3.

The pAAV-CAG plasmid had been previously generated and contained the ITRs from the AAV2 genome, the CAG promoter, and the polyA signal from rabbit β-globin, as well as a multicloning site for cloning of CDSs of interest. The CAG promoter is a hybrid promoter composed of the CMV early/intermediate enhancer and the chicken β-actin promoter. This promoter is able to drive a potent expression ubiquitously. See Sawicki J et al., Exper Cell Res. 1998; 244:367-369, Huang J et al., J Gene Med. 2003; 5:900-908, Liu Y et al., Exp Mol Med. 2007; 39(2):170-175.

Example 2: Construction of pAAV-CAG-ohIDS-Version1

Expression cassettes including an optimized version of human Iduronate-2-sulfatase cDNA sequence (ohIDS) were designed and obtained. The sequence optimization was performed to maximize the efficiency of Iduronate-2-sulfatase protein production in human beings through elimination of cryptic splice sites and RNA destabilizing sequence elements for increased RNA stability, addition of RNA stabilizing sequence elements, codon optimization and G/C content adaptation, avoidance of stable RNA secondary structures amongst others changes. The CDS for human Iduronate-2-sulfatase (NCBI Reference Sequence: NM_000202.6) was used as starting point for sequence optimization (DNA 2.0 Inc). The optimized CDS was received cloned inside the plasmid pJ204:191476 (AmpR) flanked by MluI and EcoRI restriction sites at 5' and 3', respectively.

Figure 2:
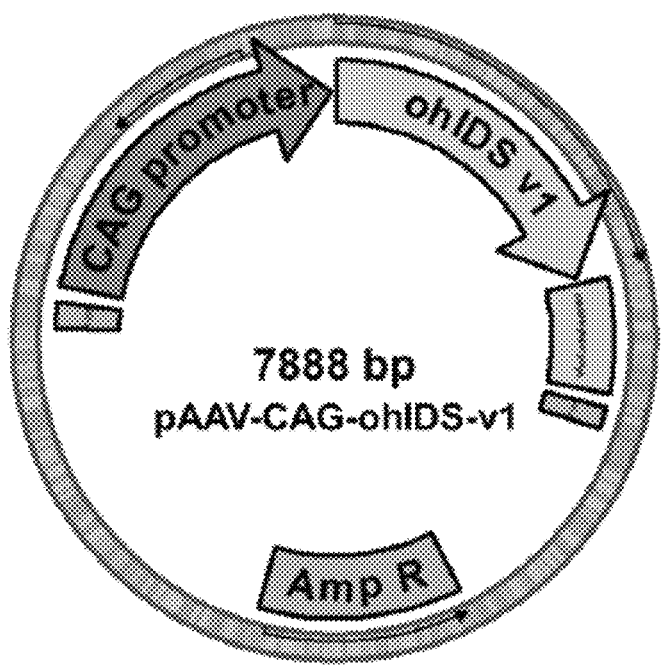
FIG. 2. Generation of pAAV-CAG-ohIDS-version1 and AAV-CAG-ohIDS-version1. (A) Schematic representation of the plasmid pAAV-CAG-ohIDS-version1 and its components. (B) Schematic representation of the genome of an Adeno-associated vector containing the ohIDS-version1 coding sequence.
Figure 2:

The MluI/EcoRI optimized human Iduronate-2-sulfatase CDS fragment was excised from the pJ204:191476 plasmid and subsequently cloned between the MluI and EcoRI restrictions sites of the AAV backbone plasmid pAAV-CAG. The resulting plasmid was named pAAV-CAG-ohIDS-version1 (accession number DSM 29867). See FIG. 2A and SEQ ID NO: 6.

Example 3: Construction of pAAV-CAG-ohIDS-Version2

The CDS for human Iduronate-2-sulfatase (NCBI Reference Sequence: NM_000202.6) was subjected to sequence optimization (GeneScript Inc). The optimized CDS was received cloned inside the plasmid pUC57 (AmpR) flanked by MluI and EcoRI restriction sites at 5' and 3', respectively.

Figure 3:
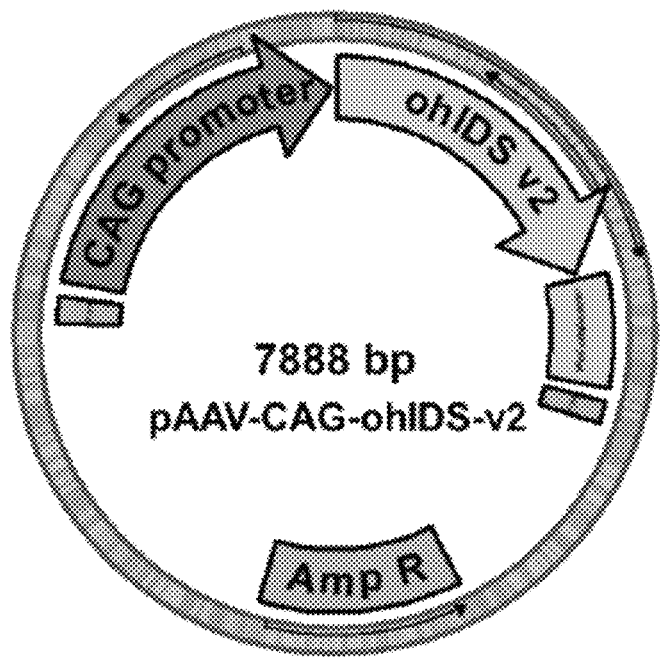
FIG. 3. Generation of pAAV-CAG-ohIDS-version2 and AAV-CAG-ohIDS-version2. (A) Schematic representation of the plasmid pAAV-CAG-ohIDS-version2 and its components. (B) Schematic representation of the genome of an Adeno-associated vector containing the ohIDS-version2 coding sequence.
Figure 3:

The pUC57-ohIDS plasmid was digested with MluI and EcoRI to excise the optimized Iduronate-2-sulfatase CDS. Subsequently, this fragment was cloned between the same restriction sites of the pAAV-CAG backbone plasmid to generate the pAAV-CAG-ohIDS-version2 plasmid (accession number DSM 29868). See FIG. 3A and SEQ ID NO:9.

Example 4: Construction of pAAV-CAG-omIDS

The CDS for murine Iduronate-2-sulfatase (NCBI Reference Sequence: NM_010498.3) was subjected to sequence optimization (GeneArt; Life Technologies). The optimized CDS was received cloned inside the plasmid pMA-RQ (AmpR) flanked by MluI and EcoRI restriction sites at 5' and 3', respectively.

Figure 4:
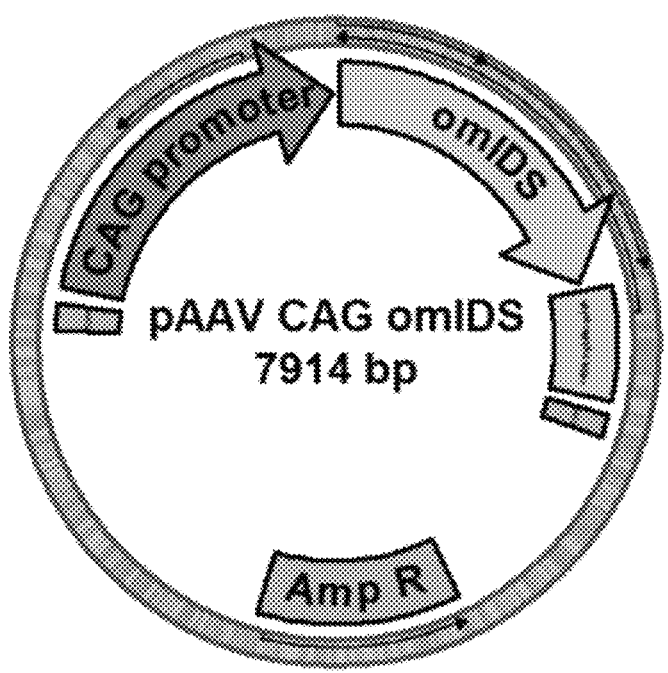
FIG. 4. Generation of pAAV-CAG-omIDS and AAV-CAG-omIDS. (A) Schematic representation of the plasmid pAAV-CAG-omIDS and its components. (B) Schematic representation of the genome of an Adeno-associated vector containing the omIDS coding sequence.
Figure 4:

The MluI/EcoRI optimized murine Iduronate-2-sulfatase CDS fragment (SEQ ID NO:11) was excised from the pMA-RQ plasmid and subsequently cloned between the MluI and EcoRI restrictions sites of the AAV backbone plasmid pAAV-CAG. The resulting plasmid was named pAAV-CAG-omIDS. See FIG. 4A and SEQ ID NO:12.

Example 5: Production of AAV9-CAG-hIDS

Vectors AAV9-CAG-hIDS (SEQ ID NO:4) were generated by helper virus-free transfection of HEK293 cells using three plasmids with modifications. See Matsushita et al., Gene Ther. 1998; 5(7):938-45, Wright et al., Mol Ther. 2005; 12(1)171-8. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-hIDS); 2) a plasmid carrying the AAV2 rep and the AAV9 cap genes (pREP2CAP9); and 3) a plasmid carrying the adenovirus helper functions. Vectors were purified by two consecutives cesium chloride gradients using an optimized protocol as previously described. See Ayuso et al., Gene Ther. 2010; 17(4):503-10. Vectors were dialyzed against PBS+0.001% Pluronic® F68, filtered, titred by qPCR and stored at −80° C. until use. See FIG. 1B.

Example 6: Production of AAV9-CAG-ohIDS-Version1

Vectors AAV9-CAG-ohIDS-version1 (SEQ ID NO:7) were generated by helper virus-free transfection of HEK293 cells using three plasmids with modifications. See Matsushita et al., and Wright et al., supra. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-ohIDS-version1); 2) a plasmid carrying the AAV2 rep and the AAV9 cap genes (pREP2CAP9); and 3) a plasmid carrying the adenovirus helper functions. Vectors were purified by two consecutives cesium chloride gradients using an optimized protocol as previously described. See Ayuso et al., supra. Vectors were dialyzed against PBS+0.001% Pluronic® F68, filtered, titred by qPCR and stored at −80° C. until use. See FIG. 2B.

Example 7: Production of AAV9-CAG-ohIDS-Version2

Vectors AAV9-CAG-ohIDS-version2 (SEQ ID NO:10) were generated by helper virus-free transfection of HEK293 cells using three plasmids with modifications. See Matsushita et al., and Wright et al., supra. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-ohIDS-version2); 2) a plasmid carrying the AAV2 rep and the AAV9 cap genes (pREP2CAP9); and 3) a plasmid carrying the adenovirus helper functions. Vectors were purified by two consecutives cesium chloride gradients using an optimized protocol as previously described. See Ayuso et al., supra. Vectors were dialyzed against PBS+0.001% Pluronic® F68, filtered, titred by qPCR and stored at −80° C. until use. See FIG. 3B.

Example 8: Production of AAV9-CAG-omIDS

Vectors AAV9-CAG-omIDS (SEQ ID NO:13) were generated by helper virus-free transfection of HEK293 cells using three plasmids with modifications. See Matsushita et al., and Wright et al., supra. Cells were cultured to 70% confluence in roller bottles (RB) (Corning, Corning, N.Y., US) in DMEM supplemented with 10% FBS and then co-transfected with: 1) a plasmid carrying the expression cassette flanked by AAV2 ITRs (pAAV-CAG-omIDS); 2) a plasmid carrying the AAV2 rep and the AAV9 cap genes (pREP2CAP9); and 3) a plasmid carrying the adenovirus helper functions. Vectors were purified by two consecutives cesium chloride gradients using an optimized protocol as previously described. See Ayuso et al., supra. Vectors were dialyzed against PBS+0.001% Pluronic® F68, filtered, titred by qPCR and stored at −80° C. until use. See FIG. 4B.

Example 9: Hydrodynamic Injection of pAAV-CAG-hIDS, pAAV-CAG-ohIDS-Version1 and pAAV-CAG-ohIDS-Version2 to Healthy Mice A total dose of 30 lag of the plasmids pAAV-CAG-hIDS, pAAV-CAG-ohIDS-version1 and pAAV-CAG-ohIDS-version2 containing different versions of the Iduronate-2-sulfatase expressing cassette were administered to 2-month-old WT mice via tail hydrodynamic tail vein injection. This technique targets expression of the delivered plasmid to the liver. See Liu et al., Gene Ther. 1990; 6(7):1258-66.

Figure 5:
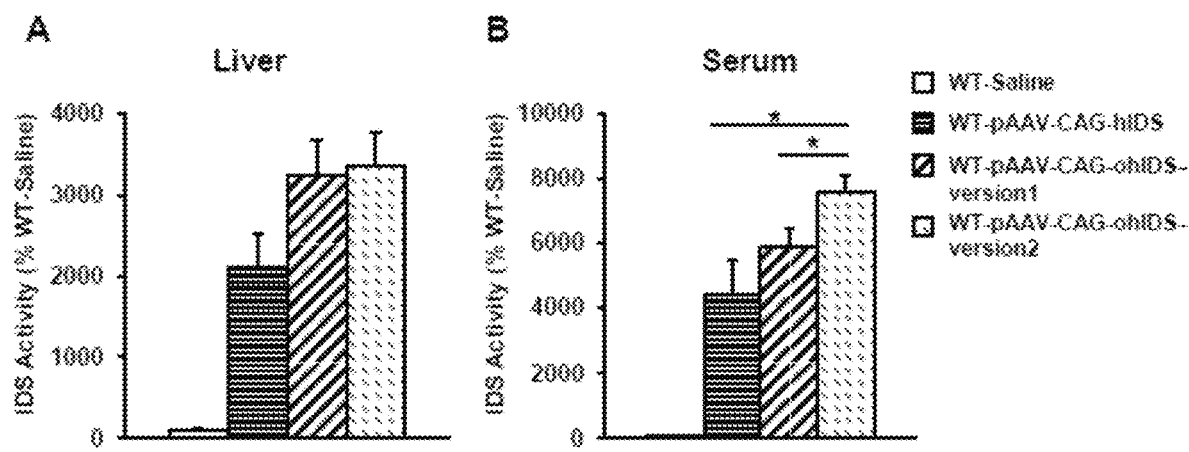
FIG. 5. Hydrodynamic delivery of pAAV-CAG-hIDS, pAAV-CAG-ohIDS-version1 and pAAV-CAG-ohIDS-version2 to healthy mice. Histograms depict iduronate-2-sulfatase (IDS) activity in liver (A) and serum (B) measured 48 hours post administration of 30 μg of the human IDS-encoding plasmids pAAV-CAG-hIDS, pAAV-CAG-ohIDS-version1 and pAAV-CAG-ohIDS-version2. IDS activity of saline-injected WT mice was set to 100%. Values are means±SEM of 5 mice per group. * $P<0.05$.

Forty-eight hours post plasmid delivery, a considerable increase over basal levels in Iduronate-2-sulfatase activity was documented in the livers and serums of all the animals administered with Iduronate-2-sulfatase-coding plasmids. In both liver and serum, the levels of activity reached with the expression cassettes containing optimized versions of the Iduronate-2-sulfatase gene were higher than those obtained with the wild-type gene. Furthermore, in serum, the animals that received the pAAV-CAG-ohIDS-version2 plasmid showed levels of Iduronate-2-sulfatase activity that were statistically higher than those documented with the other 2 plasmids. See FIGS. 5A and 5B.

Example 10: Hydrodynamic Injection of pAAV-CAG-hIDS, pAAV-CAG-ohIDS-Version1 and pAAV-CAG-ohIDS-Version2 to MPSII Mice A total dose of 30 μg of the plasmids pAAV-CAG-hIDS, pAAV-CAG-ohIDS-version1 and pAAV-CAG-ohIDS-version2 containing different versions of the Iduronate-2-sulfatase expressing cassette were administered to 3-month-old MPSII-affected mice via tail hydrodynamic tail vein injection.

Figure 6:
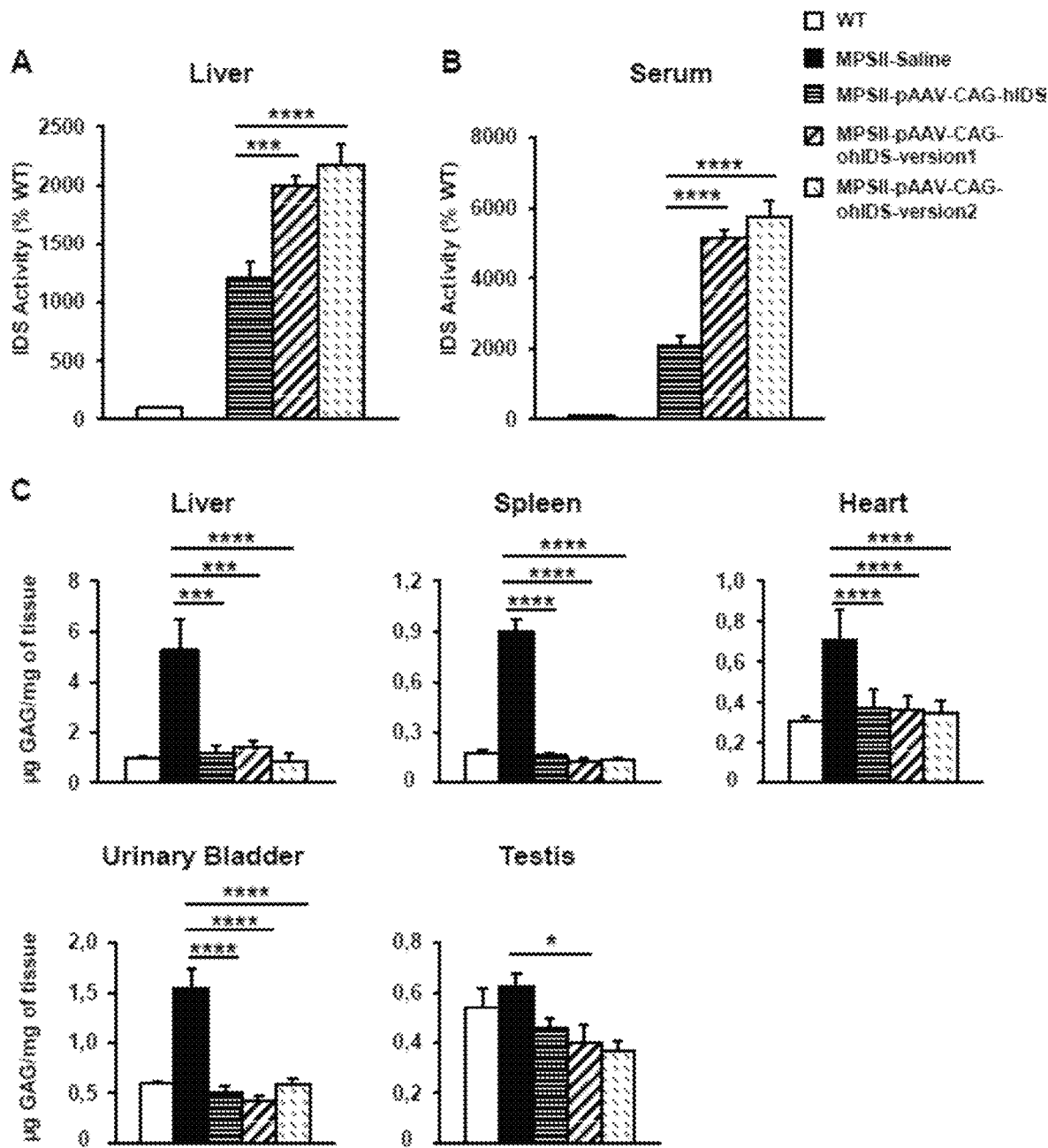
FIG. 6. Hydrodynamic delivery of pAAV-CAG-hIDS, pAAV-CAG-ohIDS-version1 and pAAV-CAG-ohIDS-version2 to MPSII mice. (A, B) Histograms depict iduronate-2-sulfatase (IDS) activity in liver (A) and serum (B) measured 1 week after administration of the human IDS-encoding plasmids pAAV-CAG-hIDS, pAAV-CAG-ohIDS-version1 and pAAV-CAG-ohIDS-version2. Wild-type and saline-injected MPSII mice were used as controls. IDS activity of WT mice was set to 100%. (C) Quantification of glycosaminoglycan (GAG) content in liver, spleen, heart, urinary bladder and testis 1 week after the administration of the different human IDS-coding plasmids. Values are means±SEM of 5 mice per group. * $P<0.05$, * $P<0.001$, ** $P<0.0001$.

Tissues were harvested 1 week after plasmid delivery. All three Iduronate-2-sulfatase-containing plasmids mediated a substantial increase in Iduronate-2-sulfatase activity with respect to MPSII animals that received saline injection; activities ranged from 1200% to 2200% of WT levels in liver and 2000% to 5700% of WT in serum. The levels of activity reached with the expression cassettes containing codon-optimized versions of the Iduronate-2-sulfatase gene were statistically higher than those mediated by the plasmid containing the wild-type gene. See FIGS. 6A and 6B.

Consistent with the high levels of Iduronate-2-sulfatase activity documented in liver and serum, GAG content was completely normalized in all tissues analysed with all plasmid constructs. See FIG. 6C.

Example 11: Intravenous Delivery of AAV9-CAG-hIDS, AAV9-CAG-ohIDS-Version1 and AAV9-CAG-ohIDS-Version2 to MPSII Mice MPSII mice (3.5-month-old) received an intravenous injection through the tail vein of $1 \times 10^{10}$ vg of AAV9 vectors containing either the wild-type or the optimized human Iduronate-2-sulfatase sequences. Separate cohorts of age-matched WT and untreated MPSII mice served as controls. Three weeks after the treatment, animals were sacrificed and blood and liver samples were collected and analysed.

Figure 7:
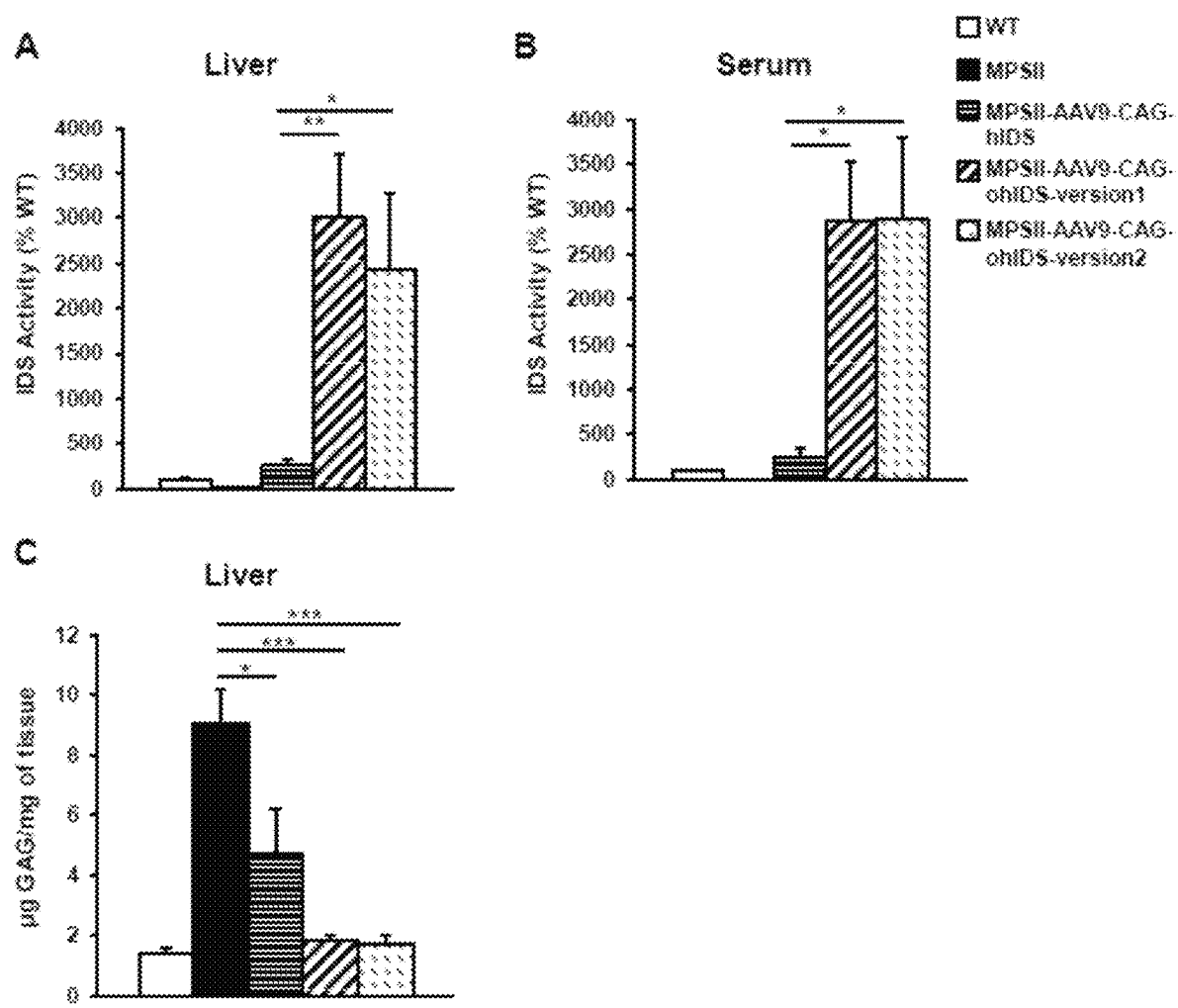
FIG. 7. Intravascular delivery of AAV9-CAG-hIDS, AAV9-CAG-ohIDS-version1 and AAV9-CAG-ohIDS-version2 to MPSII mice. MPSII mice were injected intravenously with $1\times10^{10}$ vg of AAV9 vectors encoding wild-type human IDS (AAV9-CAG-hIDS) or two different versions of optimized human IDS (AAV9-CAG-ohIDS-version1 and AAV9-CAG-ohIDS-version2). Wild-type and untreated MPSII mice were used as controls. (A, B) Histograms depict iduronate-2-sulfatase (IDS) activity in liver (A) and serum (B). IDS activity of WT mice was set to 100%. (C) Quantification of glycosaminoglycan (GAG) content in liver in animals administered with the different human IDS-coding vectors. Values are means±SEM of 5 mice per group. * $P<0.05$,  $P<0.01$ and * $P<0.001$.

The intravenous administration of AAV9 vectors at a dose of $1 \times 10^{10}$ vg/mouse targets transgene expression mainly to the liver. See Wu et al., Mol. Ther. 2006; 14(3):316-27, Inagaki et al., Mol. Ther. 2006; 14(1):45-33. When the activity of Iduronate-2-sulfatase was measured in liver extracts 3 weeks after vector delivery, a clear increase in enzymatic activity was documented in MPSII males that received any of the human IDS-coding vectors. See FIG. 7A. The increase was, however, significantly higher in the case of the MPSII animals that received the AAV9 vectors containing optimized human Iduronate-2-sulfatase sequences (AAV9-CAG-ohIDS-version1 and AAV9-CAG-ohIDS-version2). The levels of Iduronate-2-sulfatase activity reached in the animals that received vectors with the wild-type sequence were approximately the double of those observed in healthy WT animals. See FIG. 7A. With the vectors that contain the optimized human IDS sequences the levels of iduronate-2-sulfatase activity were several fold higher than those observed in healthy animals or in MPSII animals treated with vectors containing the wild-type IDS sequence. See FIG. 7A.

Iduronate-2-sulfatase is a secretable lysosomal enzyme, and as such its expression in the liver is a source of circulating enzyme. See Haurigot et al, supra. Similar to the observations made in liver extracts, the levels of Iduronate-2-sulfatase activity achieved in circulation of MPSII animals treated with the AAV9 vectors containing the optimized human IDS sequences were several fold higher than those observed in healthy animals or in MPSII animals treated with vectors containing the wild-type human IDS sequence. See FIG. 7B.

Consistent with the high levels of Iduronate-2-sulfatase activity documented in liver and serum, GAG content was completely normalized in the liver of the MPSII mice treated with AAV9-CAG-ohIDS-version1 and AAV9-CAG-ohIDS-version2. GAG levels were, however, only partially reduced in the liver of animals treated with an equal dose of AAV9 vectors carrying the wild-type IDS coding sequence. See FIG. 7C.

Example 12: Intracisternal Delivery of
AAV9-CAG-hIDS, AAV9-CAG-ohIDS-Version1
and AAV9-CAG-ohIDS-Version 2 to MPSII Mice Two-month-old MPSII mice received an intracisternal injection of $5\times10^{10}$ vg of AAV9 vectors containing either the wild-type or the optimized human Iduronate-2-sulfatase sequence in a total volume of 5 µl. Separate cohorts of age-matched WT, untreated MPSII mice and MPSII mice receiving $5\times10^{10}$ vg of a non-coding vector (AAV9-CAG-Null) served as controls. At 3.5 months of age, i.e. 1.5 months after treatment, animals were sacrificed and samples were collected and analysed.

Figure 8:
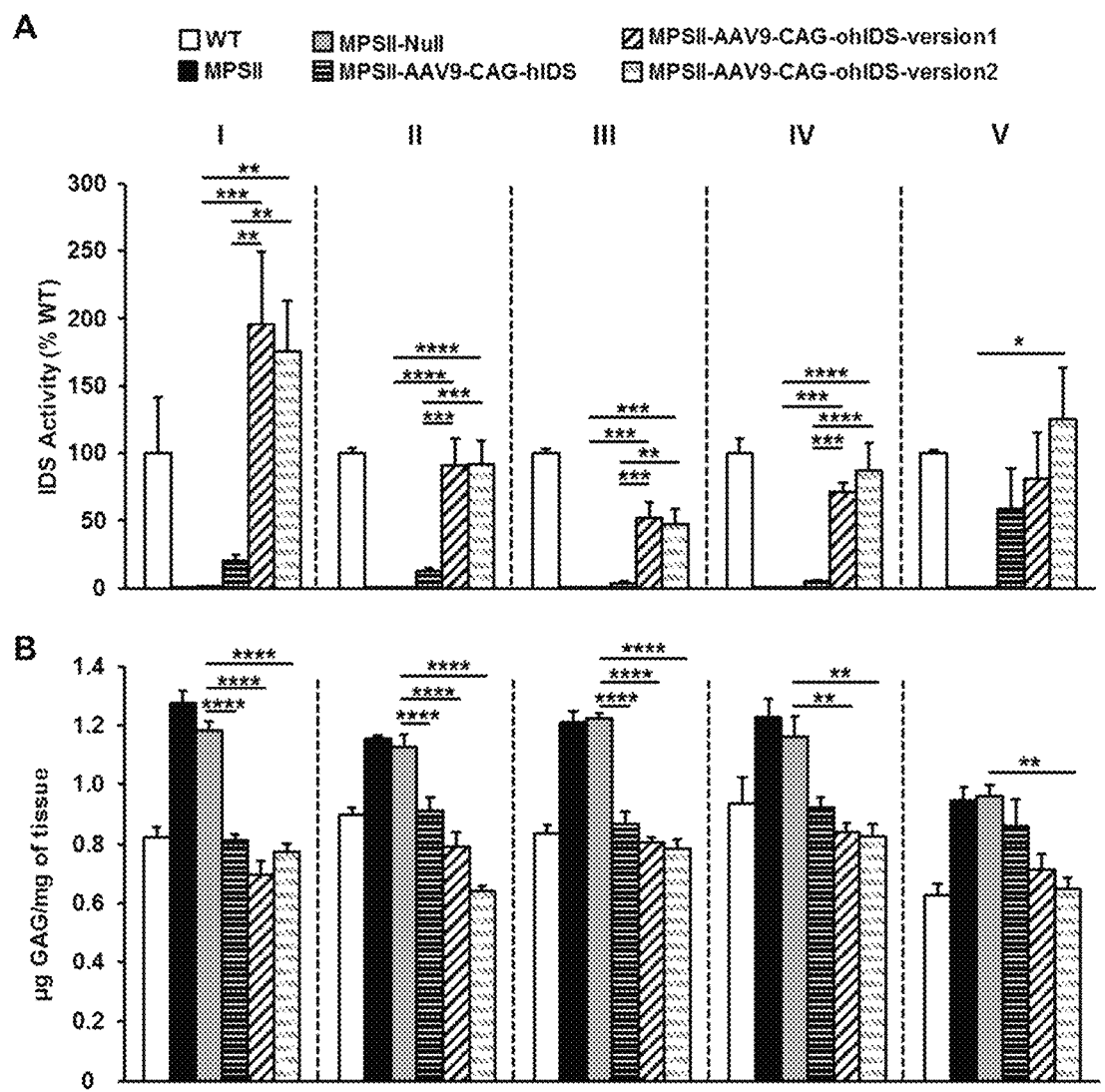
FIG. 8. Intra-CSF delivery of AAV9-CAG-hIDS, AAV9-CAG-ohIDS-version1 and AAV9-CAG-ohIDS-version2 to MPSII mice. MPSII mice aged 2 months were injected in the cisterna magna with $5\times10^{10}$ vg of AAV9 vectors encoding wild-type human IDS (AAV9-CAG-hIDS) or two different versions of optimized human IDS (AAV9-CAG-ohIDS-version1 and AAV9-CAG-ohIDS-version2). Wild-type (WT), untreated MPSII (MPSII) and MPSII mice administered with non-coding (Null) AAV9 vectors (MPSII-Null) were used as controls. (A) Iduronate-2-sulfatase activity analysed 1.5 months after vector delivery in different parts of the brain (Sections I-V, in which Section I represents the most rostral part of the brain and Section V represents the most caudal portion). IDS activity of WT mice was set to 100%. (B) Quantification of glycosaminoglycan (GAG) content in the same regions of the brain as in (A). Results are shown as mean±SEM of 5 mice per group. * $P<0.05$,  $P<0.01$, * $P<0.001$ and **** $P<0.0001$.

When the activity of Iduronate-2-sulfatase was measured in brain extracts, a clear increase in enzymatic activity was documented in MPSII males that received any of the human IDS-coding vectors. See FIG. 8A. The increase was, however, several folds higher in the case of the MPSII animals that received the AAV9 vectors containing optimized human Iduronate-2-sulfatase sequences (AAV9-CAG-ohIDS-version1 and AAV9-CAG-ohIDS-version2) than in those MPSII animals treated with vectors containing the wild-type IDS sequence. See FIG. 8A. The levels of Iduronate-2-sulfatase activity reached in the animals that received vectors with optimized human Iduronate-2-sulfatase sequences were almost as high as those of WT, or even higher; in the most rostral part of the brain (Section I) the IDS activity derived from vectors containing optimized human Iduronate-2-sulfatase sequences nearly doubled the levels of WT. See FIG. 8A.

In agreement with the increase in IDS activity throughout the brain, the accumulation of substrate that characterizes the disease was corrected in the brains of treated MPSII mice, as indicated by the significant reduction in the GAG content. See FIG. 8B. A full normalization of GAG levels was observed with all constructs in all regions analysed, except for Section V in which the effect of the expression of IDS derived from vectors containing the wild-type IDS sequence was not apparent. See FIG. 8B.

Figure 9:
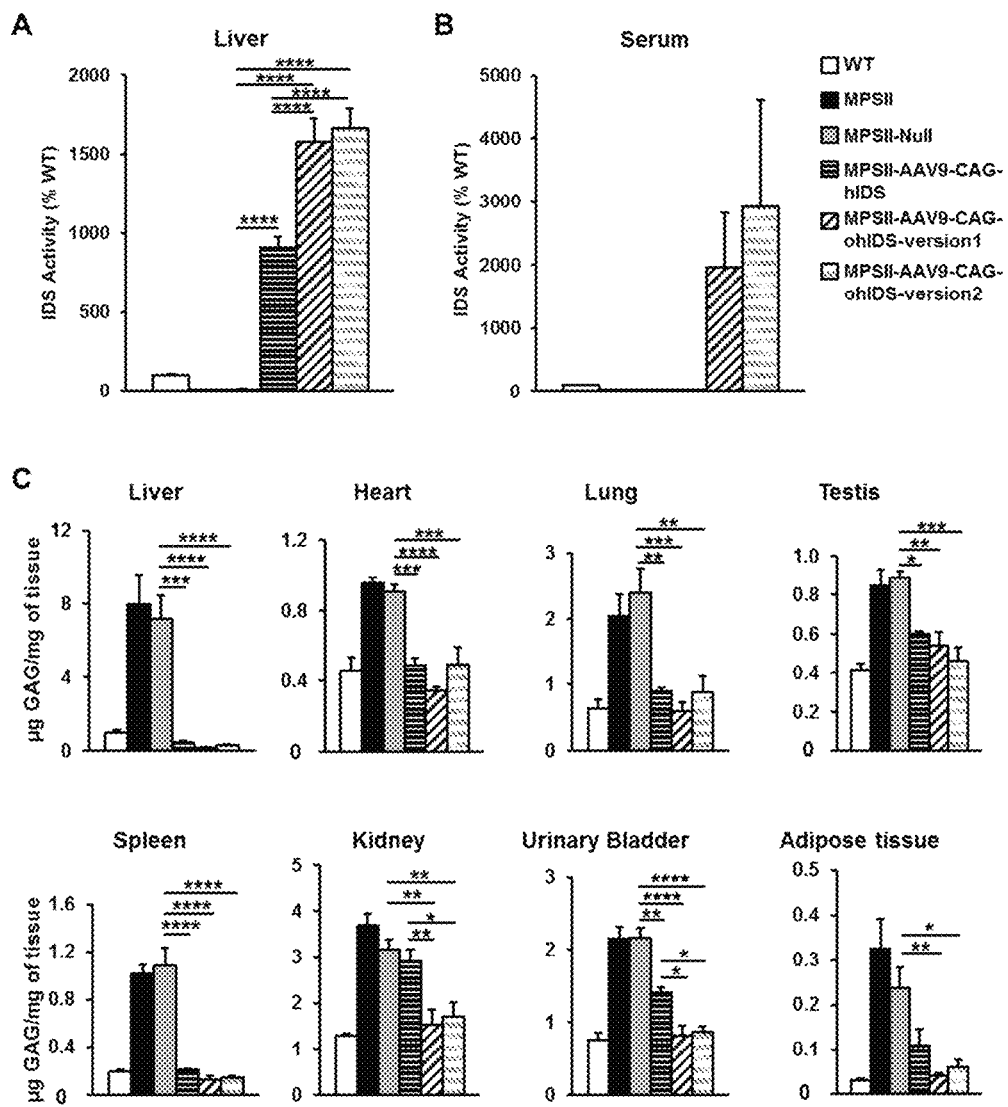
FIG. 9. Intra-CSF delivery of AAV9-CAG-hIDS, AAV9-CAG-ohIDS-version1 and AAV9-CAG-ohIDS-version2 to MPSII mice. MPSII mice aged 2 months were injected in the cisterna magna with $5\times10^{10}$ vg of AAV9 vectors encoding wild-type human IDS (AAV-CAG-hIDS) or two different versions of optimized human IDS (AAV-CAG-ohIDS-version1 and AAV-CAG-ohIDS-version2). Wild-type (WT), untreated MPSII (MPSII) and MPSII mice receiving non-coding (Null) AAV9 vectors (MPSII-Null) were used as controls. (A, B) Iduronate-2-sulfatase activity, expressed as % of WT activity, in liver (A) and serum (B), measured 1.5 months after treatment. (C) Quantification of glycosaminoglycan (GAG) content in somatic organs. Results are shown as mean±SEM of 5 mice per group. * $P<0.05$,  $P<0.01$, * $P<0.001$ and **** $P<0.0001$.

AAV9 vectors administered to the CSF leak to the periphery and transduce the liver. See Haurigot et al., Clin Invest. 2013; 123(8):3254-3271, Ribera et al., Hum Mol Genet. 2014; 24(7):2078-2095. Accordingly, an increase in Iduronate-2-sulfatase activity was documented in the liver and serum of MPSII mice treated with any of the human IDS-coding vectors. See FIGS. 9A and 9B. The increase was, again, significantly higher in the case of the MPSII animals that received the AAV9 vectors containing optimized human Iduronate-2-sulfatase sequences (AAV9-CAG-ohIDS-version1 and AAV9-CAG-ohIDS-version2) than in those MPSII animals treated with vectors containing the wild-type IDS sequence. See FIGS. 9A and 9B. When the efficacy of the therapy was evaluated through quantification of the GAG content in different somatic organs, a full normalization of the GAG levels was observed in all tissues of MPSII mice treated with any of the optimized human IDS-coding vectors. See FIG. 9C. The MPSII mice that received the wild-type human IDS sequence showed, however, a full normalization of GAG content in liver, heart, lung and spleen but only a partial correction in testis, kidney, urinary bladder and adipose tissue. See FIG. 9C.

Example 13: Intracisternal Delivery of
AAV9-CAG-omIDS

Figure 10:
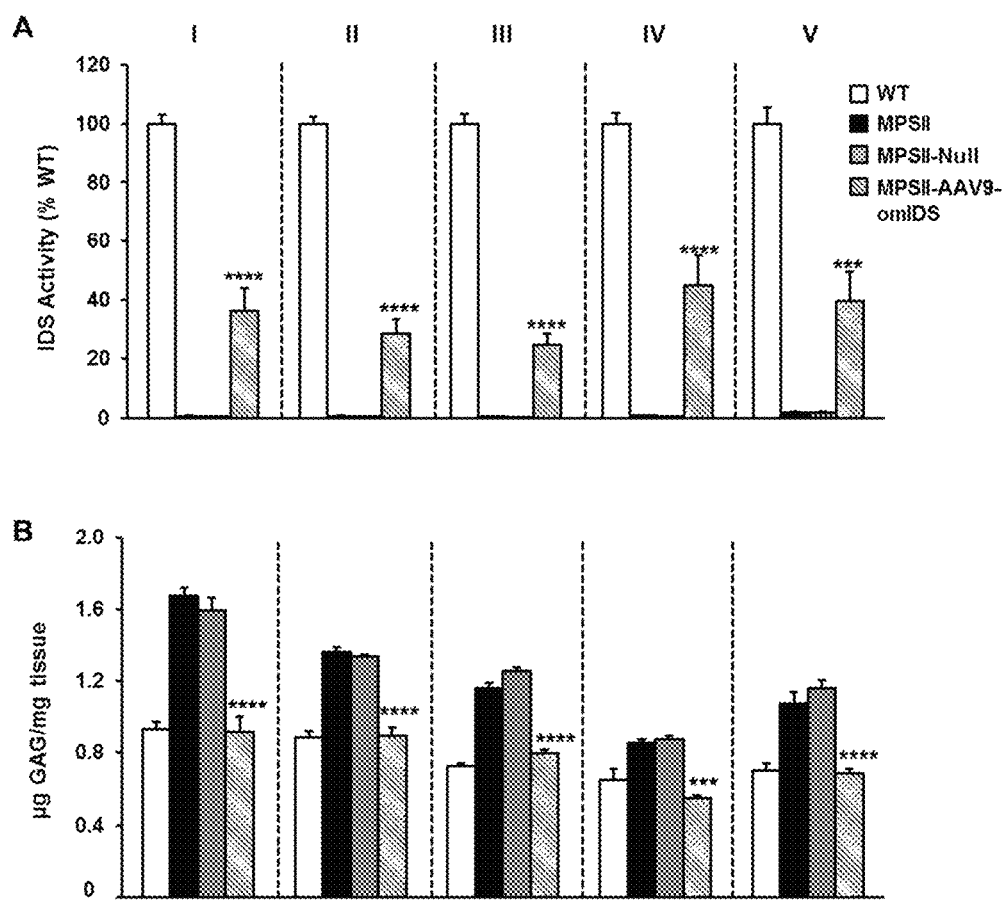
FIG. 10. Intra-CSF delivery of AAV9 vectors coding for optimized murine Iduronate-2-sulfatase (AAV9-CAG-omIDS). (A) Iduronate-2-sulfatase activity in different parts of the brain (sections I-V) of wild-type (healthy) mice, untreated MPSII mice and MPSII mice administered in the CSF, via intracisternal (IC) injection, with $5\times10^{10}$ vg of control non-coding vector (AAV9-Null) or AAV9-CAG-omIDS. WT IDS activity was set to 100%. Analysis was performed 4 months after vector delivery. (B) Quantification of glycosaminoglycans (GAGs) in the same parts of the brain as in (A). Results are shown as means±SEM of 4-5 mice per group. * $P<0.001$, ** $P<0.0001$ vs. MPSII-Null.
Figure 11:
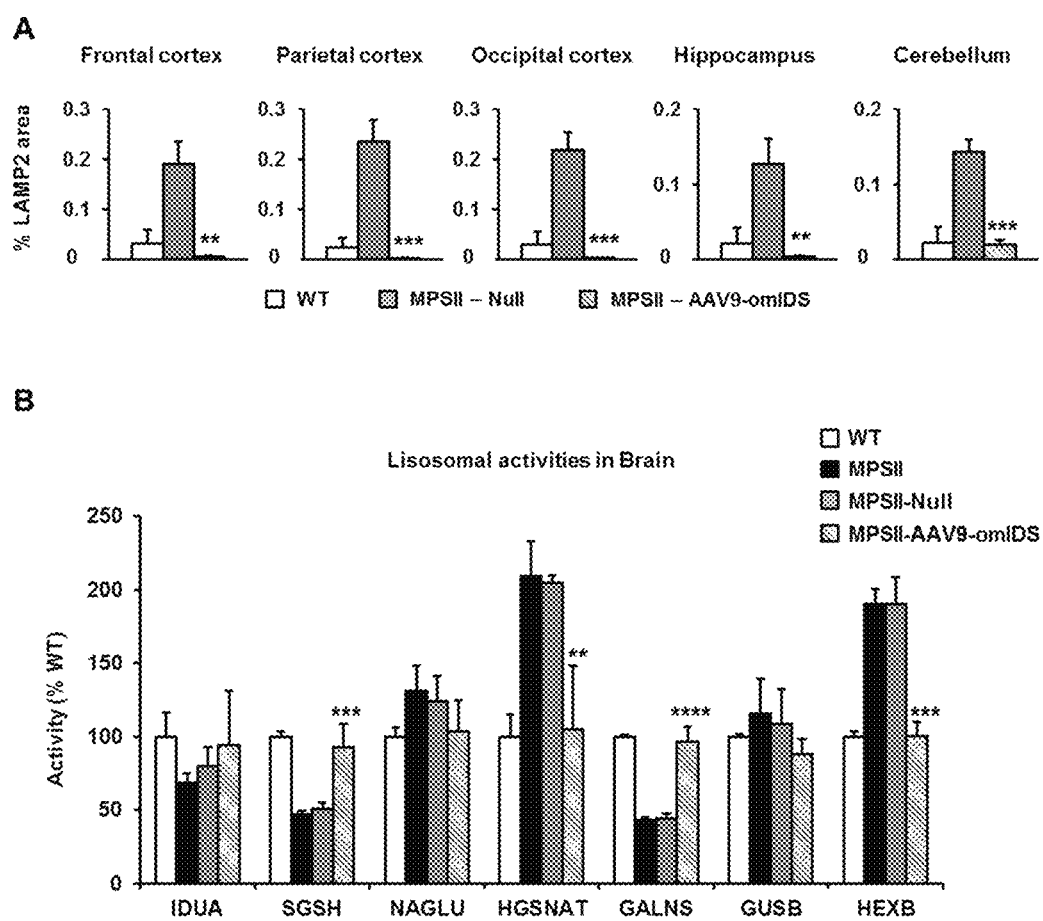
FIG. 11. Intra-CSF delivery of AAV9 vectors coding for optimized murine Iduronate-2-sulfatase (AAV9-CAGomIDS). (A) Quantification of the signal intensity obtained in different areas of the brain following staining for the lysosomal marker LAMP-2, in wild-type (healthy) mice and MPSII mice administered in the cisterna magna with either $5\times10^{10}$ vg of control non-coding vector (AAV9-Null) or $5\times10^{10}$ vg of AAV9-CAG-omIDS. Analysis was performed 4 months after vector delivery. (B) Activity of other lysosomal enzymes in brain extracts. IDUA, iduronidase, alpha-L-, SGSH, N-sulfoglucosamine sulfohydrolase, NAGLU, N-acetylglucosaminidase, alpha, HGSNAT, heparan-alpha-glucosaminide N-acetyltransferase, GALNS galactosamine (N-acetyl)-6-sulfatase, GUSB, glucuronidase, beta, HEXB, hexosaminidase B. Values are means±SEM of 4-5 mice per group.  $P<0.01$, * $P<0.001$, **** $P<0.0001$ vs. MPSII-Null.
Figure 12:
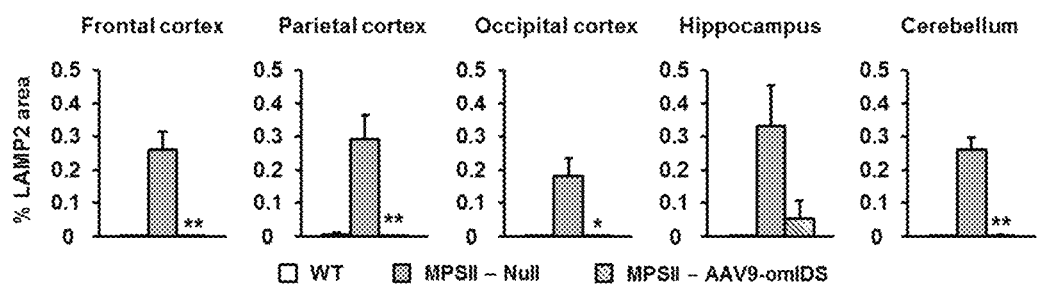
FIG. 12. Intra-CSF delivery of AAV9 vectors coding for optimized murine Iduronate-2-sulfatase (AAV9-CAG-omIDS). Quantification of the signal intensity obtained in different areas following staining of brain sections for the lysosomal marker LAMP2. Analysis was performed in wild-type (WT) mice and MPSII littermates 8 months after the latter received an intra-CSF administration of either $5\times10^{10}$ vg of control non-coding vector (AAV9-Null) or $5\times10^{10}$ vg of AAV9-CAG-omIDS. Results are shown as mean±SEM of 2-6 mice per group. *$P<0.05$ and **$P<0.01$ vs. MPSII-Null.

A total dose of $5\times10^{10}$ vector genomes of AAV9-CAG-omIDS vector was injected into the cisterna magna of 2-month-old MPSII animals in a total volume of 5 µl. First, mice were analysed at 6 months of age, i.e. 4 months after vector administration. The intra-CSF delivery of AAV9-CAG-omIDS vectors led to restoration of Iduronate-2-sulfatase activity in all brain areas analysed, reaching levels that averaged 40% of those observed in healthy animals in the different regions. See FIG. 10A. Four months post vector delivery the substrate accumulation characteristic of the disease was completely reverted in the brains of treated MPSII mice, as indicated by the normalization of GAG content in all brain areas analysed. See FIG. 10B. Likewise, the size of the lysosomal compartment was completely normalized, as indicated by the quantification of the signal intensity for the immune detection of the lysosomal marker LAMP2. LAMP2 signal is proportional to the size of the lysosomal compartment, which in turn, depends on the amount of accumulated undegraded heparan and dermatan sulphate. See FIG. 11A. Moreover, the effect of the treatment on lysosomal distension remained stable 8 months after AAV9-CAG-omIDS delivery, indicating long-term efficacy of the therapy. See FIG. 12.

The disruption of normal lysosomal homeostasis due to the accumulation of undegraded substrate can alter the activity of other lysosomal enzymes different from the one directly affected by the mutation. See Ribera et al., Hum Mol Genet. 2014; doi: 10.1093/hmg/ddu727. In the brains of untreated MPSII mice or MPSII mice treated with control "Null" vector, the activities of IDUA (iduronidase, alpha-L-), SGSH (N-sulfoglucosamine sulfohydrolase), NAGLU (N-acetylglucosaminidase, alpha), HGSNAT (heparan-alpha-glucosaminide N-acetyltransferase), GALNS (galactosamine (N-acetyl)-6-sulfatase), GUSB (glucuronidase, beta), HEXB (hexaminidase B) were altered, but treatment with AAV9-CAG-omIDS returned those activities to the levels observed in healthy WT animals indicating that the vector was capable of restoring lysosomal homeostasis. See FIG. 11B.

Figure 13:
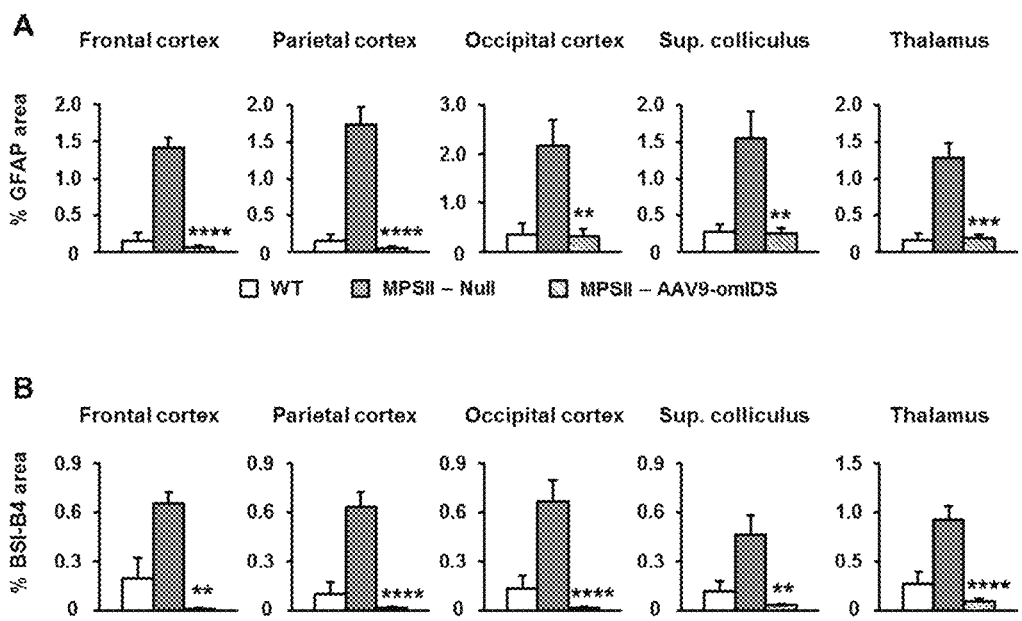
FIG. 13. Intra-CSF delivery of AAV9 vectors coding for optimized murine Iduronate-2-sulfatase (AAV9-CAG-omIDS). (A, B) Histograms represent the signal intensity measured following immunostaining for the astrocyte marker GFAP (A) and for the microglial marker BSI-B4 (B) in sections of frontal, parietal, and occipital cortex, superior colliculus, and thalamus from wild-type (healthy) mice, and MPSII mice administered 4 months before in the cisterna magna with either $5\times10^{10}$ vg of control non-coding vector (AAV9-Null) or $5\times10^{10}$ vg of AAV9-CAG-omIDS. Results are shown as means±SEM of 5 mice per group.  $P<0.01$, * $P<0.001$, **** $P<0.0001$ vs. MPSII-Null.
Figure 14:
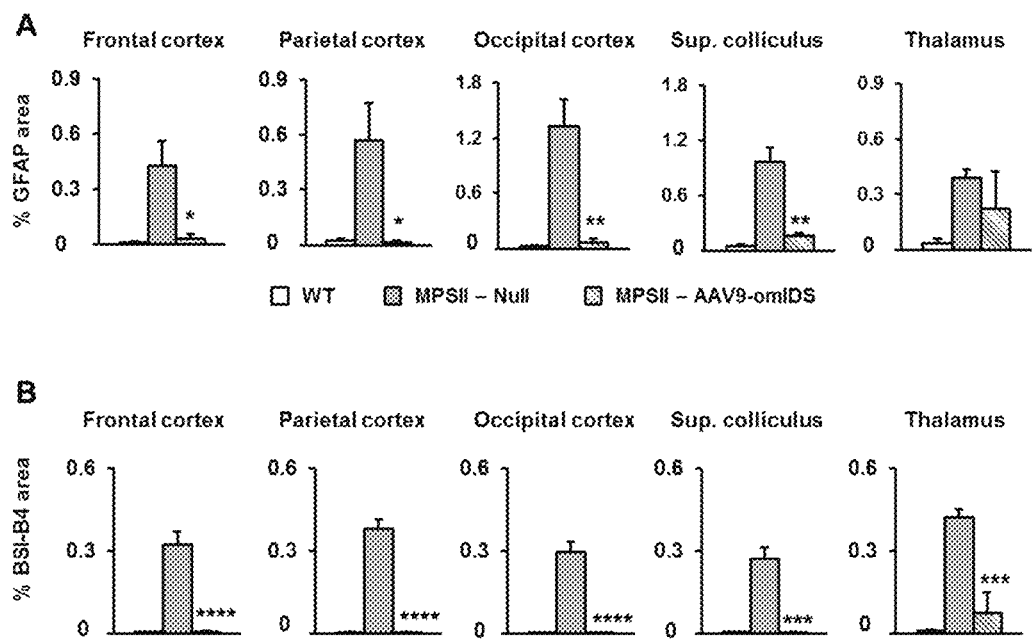
FIG. 14. Intra-CSF delivery of AAV9 vectors coding for optimized murine Iduronate-2-sulfatase (AAV9-CAG-omIDS). (A, B) Histograms represent the signal intensity measured following immunostaining for the astrocyte marker GFAP (A) and for the microglial marker BSI-B4 (B) in sections of the encephalon from healthy wild-type (WT) mice and MPSII littermates that received intra-CSF administration of either $5\times10^{10}$ vg of control non-coding vector (AAV9-Null) or $5\times10^{10}$ vg of AAV9-CAG-omIDS. Analysis was performed 8 months after vector delivery. Results are shown as mean±SEM of 2-6 mice per group. *$P<0.05$, $P<0.01$, *$P<0.001$ and **$P<0.0001$ vs. MPSII-Null FIG. 15. Intra-CSF delivery of AAV9 vectors coding for optimized murine Iduronate-2-sulfatase (AAV9-CAG-omIDS). (A,B) Iduronate-2-sulfatase activity, expressed as % of WT activity, in liver (A) and serum (B) of wild-type (healthy) mice, untreated MPSII mice and MPSII mice administered in the CSF with $5\times10^{10}$ vg of control non-coding vector (AAV9-Null) or $5\times10^{10}$ vg of AAV9-CAG-omIDS vector at 2 months of age and analysed 4 months later. WT IDS activity was set to 100%. (C) Quantification of glycosaminoglycans (GAGs) in somatic organs. Results are shown as means±SEM of 4-5 mice per group.  $P<0.01$, * $P<0.001$, ** $P<0.0001$ vs. MPSII-Null.

In agreement with the correction of the lysosomal pathology, all signs of inflammation disappeared from the brains of treated MPSII mice. Four months post treatment, the signal intensities for the stainings used to detect astrocytosis (GFAP) and microgliosis (BSI-B4) were similar in treated MPSII mice and in healthy animals in different brain regions, as opposed to the signal documented in MPSII mice administered with the control "Null" AAV9 vector that showed a clear upregulation of these markers of neuroinflammation. See FIGS. 13A and 13B. Furthermore, at 10 months of age, i.e. 8 months after gene transfer, the beneficial impact of AAV9-CAG-omIDS treatment on neuroinflammation-evaluated through staining for both GFAP and BSI-B4-persisted, indicating long-term eradication of neuroinflammation. See FIGS. 14A and 14B.

Figure 15:
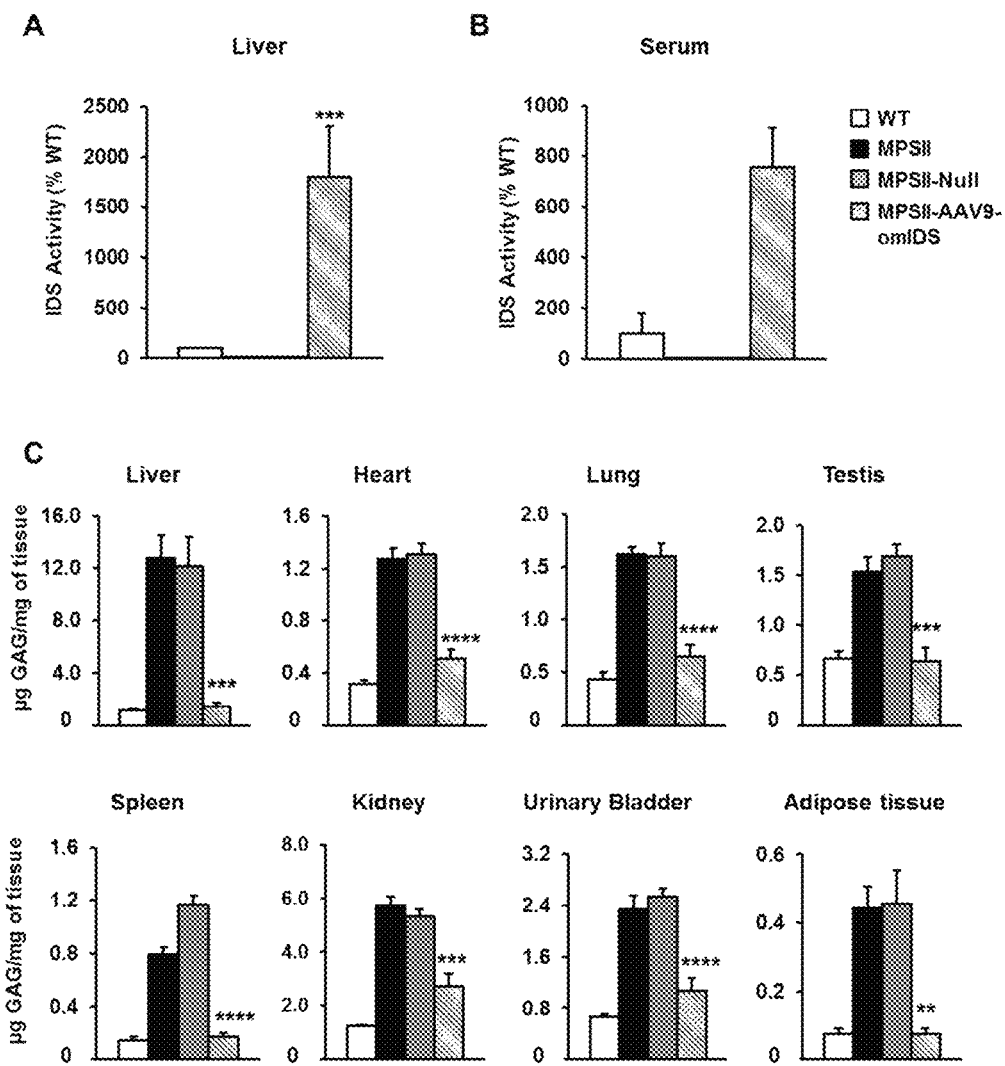

AAV9 vectors administered to the CSF leak to the periphery and transduce the liver. See Haurigot et al., Clin Invest. 2013; 123(8):3254-3271, Ribera et al., Hum Mol Genet. 2014; doi: 10.1093/hmg/ddu727. Accordingly, an increase in Iduronate-2-sulfatase activity was documented 4 months after gene transfer in the liver and serum of MPSII mice treated with AAV9-CAG-omIDS, reaching levels of approximately 1700% and 700% of the levels observed in healthy animals, respectively. See FIGS. 15A and 15B. When the somatic efficacy of the therapy was evaluated through quantification of the GAG content in different organs, a full normalization was observed in most tissues, including liver, heart, lung, testis, spleen and, adipose tissue, with the exception of kidney and urinary bladder, in which a >50% reduction of GAGs was observed. See FIG. 15C.

Figure 16:
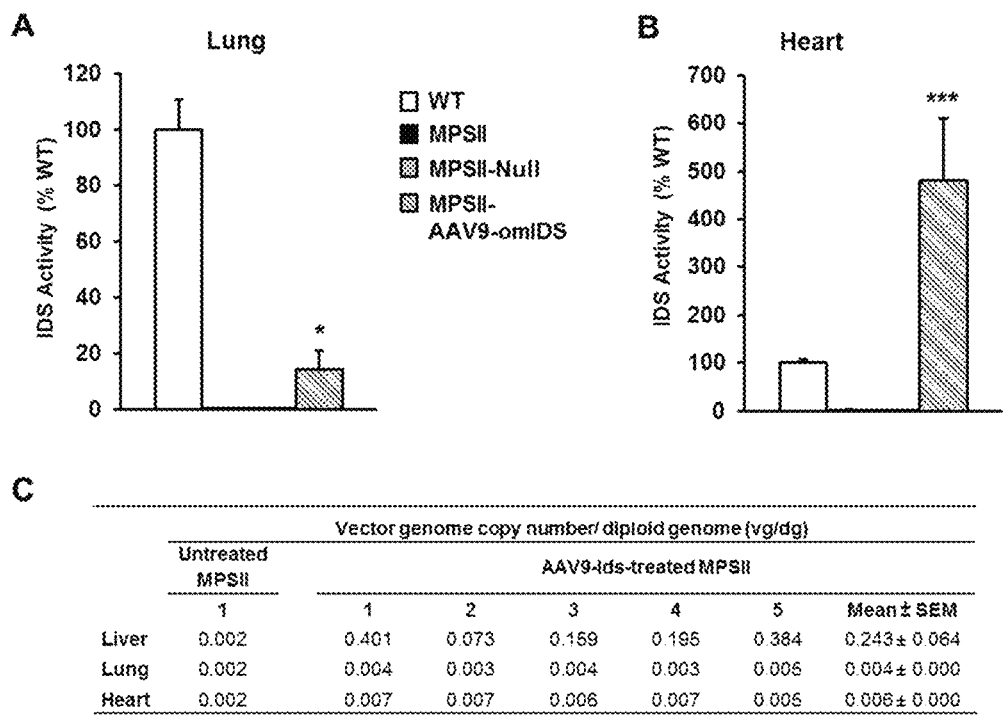
FIG. 16. Intra-CSF delivery of AAV9 vectors coding for optimized murine Iduronate-2-sulfatase (AAV9-CAG-omIDS). (A, B) Iduronate-2-sulfatase activity, expressed as % of WT activity, in lung (A) and heart (B) of healthy wild-type (WT) mice, untreated MPSII (MPSII) mice and MPSII mice administered in the CSF with $5\times10^{10}$ vg of control non-coding vector (AAV9-Null) or $5\times10^{10}$ vg of AAV9-CAG-omIDS vector at 2 months of age and analysed 4 months later. (C) Quantification of vector genome copy number/diploid genome (vg/dg) in liver, lung and heart in MPSII mice administered intra-CSF with AAV9-CAG-omIDS. Tissues obtained from an untreated MPSII mouse were used as controls. Results are shown as mean±SEM of 4-5 mice per group in (A and B). *$P<0.05$, $P<0.01$ and *$P<0.001$ MPSII-Null.

Four months after treatment IDS activity was also increased in lung and was particularly high in heart. See FIGS. 16A and 16B. These two organs, lung and heart, presented very low values of vector genome copy number/diploid genome, indicating lack of efficient transduction of these organs following intra-CSF AAV9-CAG-omIDS delivery at the dose of 5×10$^{10}$ vg. See FIG. 16C. This finding suggested cross-correction of IDS deficiency by uptake of IDS from the circulation.

Figure 17:
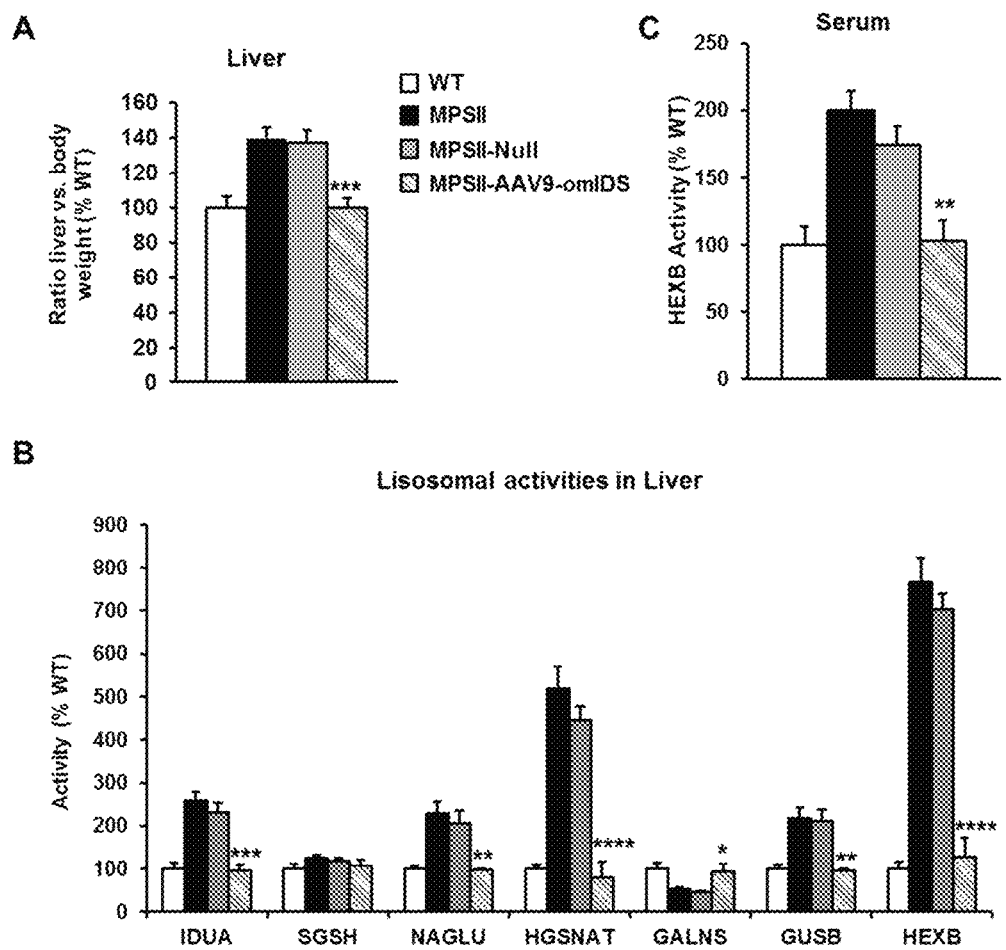
FIG. 17. Intra-CSF delivery of AAV9 vectors coding for optimized murine Iduronate-2-sulfatase (AAV9-CAG-omIDS). (A) Wet weight of the liver relative to whole body weight of wild-type (healthy) mice, untreated MPSII mice and MPSII mice administered in the CSF with $5\times10^{10}$ vg of control vector (AAV9-Null) or $5\times10^{10}$ vg of AAV9-CAG-omIDS vector at two months of age and analysed 4 months later. (B) Activity of other lysosomal enzymes in liver extracts obtained from the same cohorts of animals as in (A). (C) β-hexosaminidase (β-HEXO) activity, expressed as % of WT activity, in serum of the same animal cohorts as in (A). IDUA, iduronidase, alpha-L-, SGSH, N-sulfoglucosamine sulfohydrolase, NAGLU, N-acetylglucosaminidase, alpha, HGSNAT, heparan-alpha-glucosaminide N-acetyltransferase, GALNS galactosamine (N-acetyl)-6-sulfatase, GUSB, glucuronidase, beta, HEXB, hexosaminidase B. WT enzyme activities were set to 100%. Values are means±SEM of 4-5 mice per group. * $P<0.05$,  $P<0.01$, * $P<0.001$, *** $P<0.0001$ vs. MPSII-Null.
Figure 18:
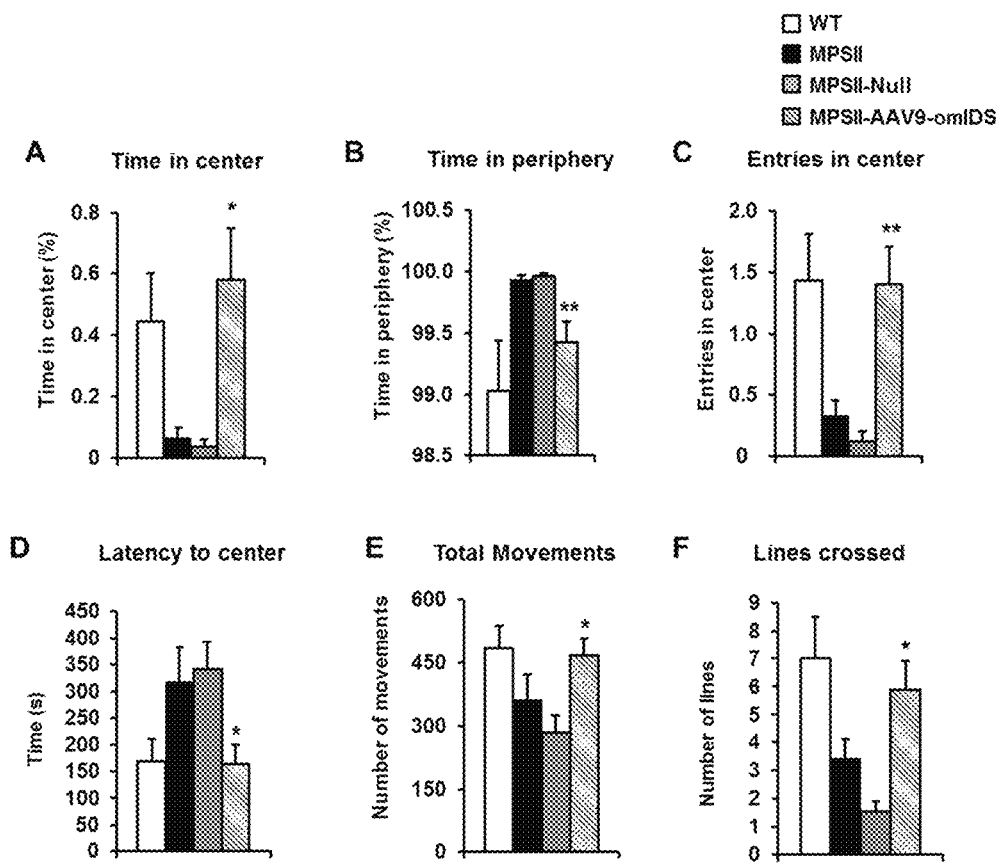
FIG. 18. Intra-CSF delivery of AAV9 vectors coding for optimized murine Iduronate-2-sulfatase (AAV9-CAG-omIDS). Locomotor and exploratory activity evaluation thorough the Open Field test in naïve wild-type (healthy) mice, untreated MPSII mice and MPSII mice administered in the CSF with $5\times10^{10}$ vg of control vector (AAV9-Null) or $5\times10^{10}$ vg of AAV9-CAG-omIDS vector at two months of age and analysed 4 months later. (A) Time in center, (B) Time in periphery, (C) Entries in center, (D) Latency to center, (E) Total movements, (F) Lines crossed. Values are means±SEM of 17-22 mice per group. * $P<0.05$, ** $P<0.01$ vs. MPSII-Null.

In agreement with the GAG content data, the weight of the liver was normalized in 6-month-old MPSII mice treated with AAV9-CAG-omIDS at the age of 2 months. See FIG. 17A. Further demonstration of the potential of intra-CSF AAV9-CAG-omIDS treatment to counteract lysosomal pathology in MPSII mice was provided by the measurement of activity of other lysosomal enzymes in liver extracts. IDUA, SGSH, NAGLU, HGSNAT, GALNS, GUSB, HEXB were considerably altered with respect to WT levels in untreated MPSII mice or in MPSII mice treated with control "Null" vector. Treatment with AAV9-CAG-omIDS completely normalized the activities of all these enzymes. See FIG. 17B. Furthermore, serum HEXB activity also increases as a consequence of lysosomal pathology, and it was completely normalized following AAV9-CAG-omIDS treatment, See FIG. 17C, providing evidence of whole-body correction of lysosomal functionality.

The impact of the intra-CSF administration of AAV9-CAG-omIDS on behaviour was assessed at 6 months of age with the Open Field test, which evaluates the general locomotor and exploratory activity of mice in unknown surroundings. Untreated and AAV9-null-treated MPSII mice displayed reduced exploratory activity compared with healthy mice in terms of the time spent in the centre and in the periphery, the number of entries in the centre and in the periphery and the total number of fast movements. Intracisternal administration of AAV9-CAG-omIDS completely corrected behavioural deficits in MPSII mice. See FIGS. 18A-F.

Figure 19:
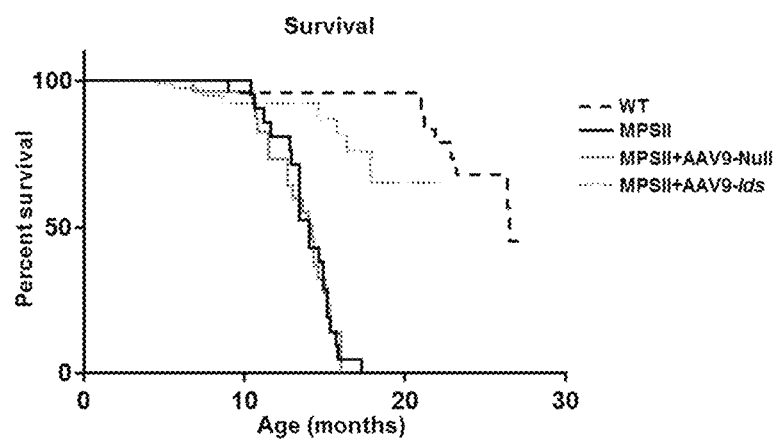
FIG. 19. Intra-CSF delivery of AAV9 vectors coding for optimized murine Iduronate-2-sulfatase (AAV9-CAG-omIDS). Kaplan-Meier analysis of survival in healthy wild-type (WT) mice, untreated MPSII (MPSII) mice and MPSII mice administered in the CSF with $5\times10^{10}$ vg of control non-coding vector (AAV9-Null) or $5\times10^{10}$ vg of AAV9-CAG-omIDS vector. N=24 for WT, N=22 for untreated MPSII, N=27 for Null-injected MPSII and N=91 for mice receiving therapeutic vector.

Finally, the therapeutic efficacy of intra-CSF AAV9-CAG-omIDS treatment was evaluated by comparing the survival of untreated and treated MPSII mice. AAV9-CAG-omIDS gene therapy considerably extended the lifespan of MPSII mice. See FIG. 19. Whilst at 17 months of age all untreated or AAV9-CAG-Null-treated MPSII mice were dead, 76% of MPSII mice receiving AAV9-CAG-omIDS treatment were alive. Moreover, 65% of treated animals were still alive at 22 months of age. The % of wild-type animals alive at this age was 79%. See FIG. 19.

Example 14: Intracisternal Delivery of Different Doses of AAV9-CAG-omIDS: Dose-Response Study Four different doses (1.58×10$^9$, 5×10$^9$, 1.58×10$^{10}$ and 5×10$^{10}$ vg/mouse) of AAV9-CAG-omIDS vectors were administered to 2-month-old MPSII animals via intracisternal injection in a total volume of 5 µl.

Figure 20:
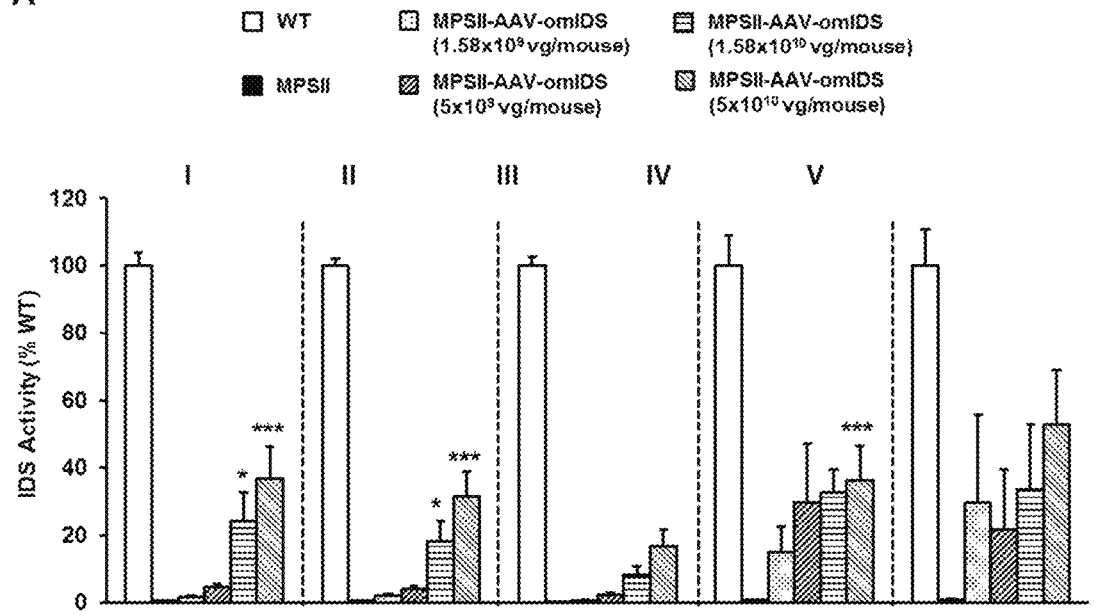
FIG. 20. Intra-CSF delivery of AAV9 vectors coding for optimized murine Iduronate-2-sulfatase (AAV9-CAG-omIDS) at different doses ($1.58\times10^9$, $5\times10^9$, $1.58\times10^{10}$ and $5\times10^{10}$ vg/mouse). (A) Iduronat-2-sulfatase activity in different parts of the brain (sections I-V) of wild-type (healthy) mice, untreated MPSII mice and MPSII mice administered in the CSF via intracisternal (IC) injection with different doses of AAV9-CAG-omIDS at 2 months of age and analysed 1.5 months later. WT IDS activity was set to 100%. (B) Quantification of glycosaminoglycans (GAGs) in the same parts of the brain as in (A). Results are shown as means±SEM of 5 mice per group. * $P<0.05$,  $P<0.01$, * $P<0.001$, **** $P<0.0001$ vs. untreated MPSII.
Figure 20:
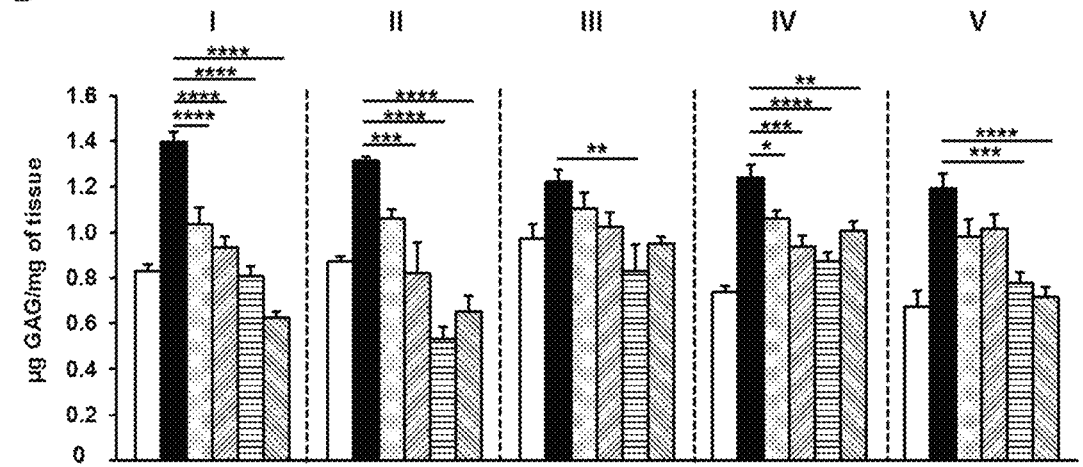

One and a half months post vector administration, animals were sacrificed and tissues harvested. Iduronat-2-sulfatase activity was measured in different parts of the brain (sections I-V). Activity increased with dose and ranged from 0.8 and 53% of WT activity in the different regions. See FIG. 20A. A similar dose-response was observed when the effect of the treatment on GAG storage was analysed. However, a complete correction of GAG accumulation was documented only at the two highest doses 1.58×10$^{10}$ and 5×10$^{10}$ vg/mouse. See FIG. 20B.

Figure 21:
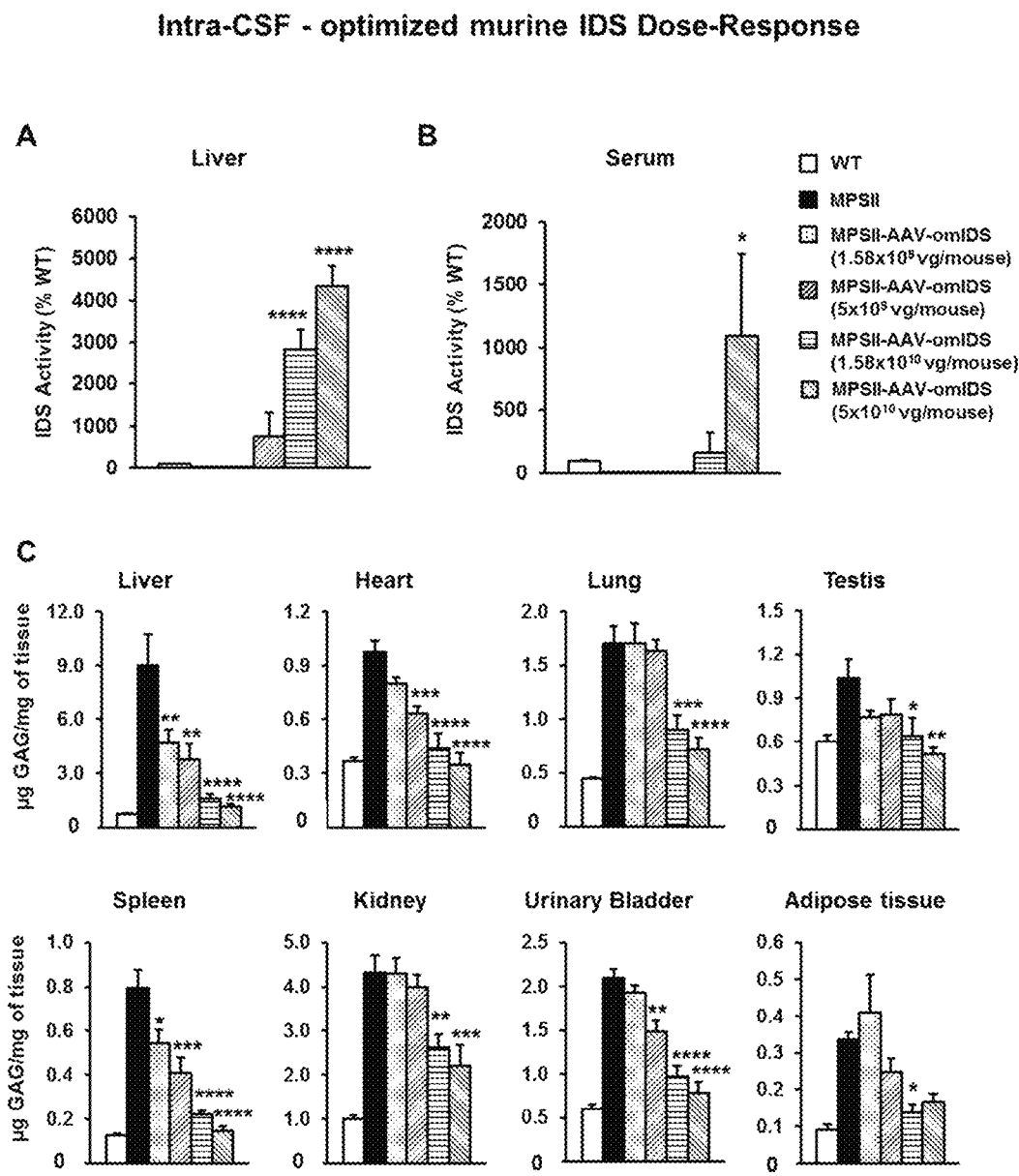
FIG. 21. Intra-CSF delivery of AAV9 vectors coding for optimized murine Iduronate-2-sulfatase (AAV9-CAG-omIDS) at different doses ($1.58\times10^9$, $5\times10^9$, $1.58\times10^{10}$ and $5\times10^{10}$ vg/mouse). (A, B) Iduronate-2-sulfatase activity, expressed as % of WT activity, in liver (A) and serum (B)

In the liver and serum, activity also increased with dose, ranging from 20% to 4300% in the liver and 0.4% and 1100% in serum. No IDS activity was detectable in serum with the 2 lowest doses (1.58×10$^9$, 5×10$^9$ vg/mouse). See FIGS. 21A and 21B. In agreement with the activity data, the measurement of GAG content in peripheral tissues demonstrated a dose-response decrease in GAG content in liver, heart, lung, testis, spleen, kidney, urinary bladder and adipose tissue. Complete or almost complete normalization of GAG levels was achieved in most tissues with the 2 highest doses (1.58×10$^{10}$ and 5×10$^{10}$ vg/mouse), with the exceptions of lung and urinary bladder, in which >70% reductions were documented, and kidney, in which an approximately 50% decrease was observed. See FIG. 21C.

The invention claimed is:

1. A plasmid comprising a nucleic acid sequence encoding Iduronate-2-sulfatase (IDS) enzyme consisting of the amino acid sequence as set forth in SEQ ID NO: 1, wherein the plasmid is pAAV-CAG-ohIDS-version1, deposited under accession number DSM 29867, comprising the nucleotide sequence as set forth in SEQ ID NO: 6.

2. A plasmid comprising a nucleic acid sequence encoding Iduronate-2-sulfatase (IDS) enzyme consisting of the amino acid sequence as set forth in SEQ ID NO: 1, wherein the plasmid is pAAV-CAG-ohIDS-version2, deposited under accession number DSM 29868, comprising the nucleotide sequence as set forth in SEQ ID NO: 9.

3. A recombinant wild type Adeno-associated Virus Vector of serotype 9 (AAV9) comprising a nucleic acid sequence encoding Iduronate-2-sulfatase (IDS) enzyme consisting of the amino acid sequence as set forth in SEQ ID NO: 1, wherein the AAV9 vector is AAV9-CAG-ohIDS-version1, comprising the nucleotide sequence as set forth in SEQ ID NO: 5.

4. A recombinant type Adeno-associated Virus Vector of serotype 9 (AAV9) comprising a nucleic acid sequence encoding Iduronate-2-sulfatase (IDS) enzyme consisting of the amino acid sequence as set forth in SE 0 ID NO: 1, wherein the AAV9 vector is AAV9-CAG-ohIDS-version2, comprising the nucleotide sequence as set forth in SEQ ID NO: 8.

5. A pharmaceutical composition comprising a therapeutically effective amount of the recombinant AAV9 of claim 3.

6. A pharmaceutical composition comprising a therapeutically effective amount of the recombinant AAV9 of claim 4.

7. The pharmaceutical composition of claim 6 which is in a form for intravenous or intracisternal administration.

* * * * *

UNITED STATES PATENT AND TRADEMARK OFFICE
CERTIFICATE OF CORRECTION

PATENT NO. : 10,617,771 B2
APPLICATION NO. : 15/578366
DATED : April 14, 2020
INVENTOR(S) : Fàtima Bosch Tubert, Virginia A. Haurigot-Mendonça and Sandra Motas Mallol Page 1 of 1

It is certified that error appears in the above-identified patent and that said Letters Patent is hereby corrected as shown below:

On the Title Page

Page 2, Column 1 under "OTHER PUBLICATIONS", Line 20: 2015 should read 2016.

Column 2, Line 38: Frisco should read FRISO.

In the Claims

Column 84, Line 33: Type should read wild type.
       Line 36: SE O should read SEQ.

Signed and Sealed this
Seventh Day of July, 2020

Andrei Iancu
*Director of the United States Patent and Trademark Office*